US010103341B2

(12) United States Patent
Inoue et al.

(10) Patent No.: US 10,103,341 B2
(45) Date of Patent: *Oct. 16, 2018

(54) ORGANOMETALLIC COMPLEX AND LIGHT EMITTING ELEMENT, LIGHT EMITTING DEVICE, AND ELECTRONIC DEVICE USING THE ORGANOMETALLIC COMPLEX

(71) Applicant: Semiconductor Energy Laboratory Co., Ltd., Kanagawa-ken (JP)

(72) Inventors: Hideko Inoue, Kanagawa (JP); Satoshi Seo, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 371 days.

This patent is subject to a terminal disclaimer.

(21) Appl. No.: 14/678,467

(22) Filed: Apr. 3, 2015

(65) Prior Publication Data

US 2015/0214484 A1   Jul. 30, 2015

Related U.S. Application Data

(63) Continuation of application No. 11/725,971, filed on Mar. 20, 2007, now Pat. No. 8,999,520.

(30) Foreign Application Priority Data

Mar. 21, 2006   (JP) .................................. 2006-077899

(51) Int. Cl.
  *H01L 51/00* (2006.01)
  *C07F 15/00* (2006.01)
  (Continued)

(52) U.S. Cl.
  CPC ........ *H01L 51/009* (2013.01); *C07F 15/0033* (2013.01); *H01L 51/0085* (2013.01);
  (Continued)

(58) Field of Classification Search
  None
  See application file for complete search history.

(56) References Cited

U.S. PATENT DOCUMENTS 5,484,922 A   1/1996   Moore et al.
6,780,528 B2  8/2004   Tsuboyama et al.
(Continued)

FOREIGN PATENT DOCUMENTS

CN   001478372 A   2/2004
CN   001678617 A   10/2005
(Continued)

OTHER PUBLICATIONS

Duan, J.-P. et al., "New Iridium Complexes as Highly Efficient Orange-Red Emitters in Organic Light-Emitting Diodes," Advanced Materials, Feb. 5, 2003, vol. 15, No. 3, pp. 224-228.
(Continued)

*Primary Examiner* — Jay Yang
(74) *Attorney, Agent, or Firm* — Husch Blackwell LLP

(57) ABSTRACT

An organometallic complex having a structure represented by the following general formula (G1) is provided.
(Continued)

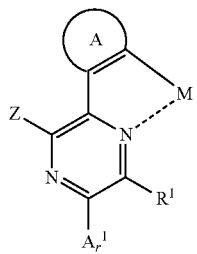

(G1)

(In the formula, A represents an aromatic hydrocarbon group having 6 to 25 carbon atoms. Further, Z represents any one of hydrogen, an alkyl group having 1 to 4 carbon atoms, an alkoxy group having 1 to 4 carbon atoms, or an aryl group having 6 to 25 carbon atoms. In addition, $A_r^1$ represents an aryl group having 6 to 25 carbon atoms. $R^1$ represents any one of hydrogen, an alkyl group having 1 to 4 carbon atoms, or an alkoxy group having 1 to 4 carbon atoms. Further, M is a central metal and represents an element belonging to Group 9 or Group 10.)

20 Claims, 33 Drawing Sheets

(51) Int. Cl.
*H01L 27/32* (2006.01)
*H01L 51/50* (2006.01)

(52) U.S. Cl.
CPC ...... *H01L 51/0087* (2013.01); *H01L 27/3209* (2013.01); *H01L 51/5012* (2013.01); *H01L 51/5016* (2013.01); *H01L 51/5036* (2013.01); *H01L 51/5088* (2013.01)

(56) References Cited

U.S. PATENT DOCUMENTS

| | | | |
|---|---|---|---|
| 6,821,646 B2 | 11/2004 | Tsuboyama et al. | |
| 6,830,828 B2 | 12/2004 | Thompson et al. | |
| 6,953,628 B2 | 10/2005 | Kamatani et al. | |
| 6,991,857 B2 | 1/2006 | Tsuboyama et al. | |
| 7,094,477 B2 | 8/2006 | Kamatani et al. | |
| 7,147,935 B2 | 12/2006 | Kamatani et al. | |
| 7,205,054 B2 | 4/2007 | Tsuboyama et al. | |
| 7,220,495 B2 | 5/2007 | Tsuboyama et al. | |
| 7,521,130 B2 | 4/2009 | Lee et al. | |
| 7,527,879 B2 | 5/2009 | Kamatani et al. | |
| 7,544,426 B2 | 6/2009 | Kamatani et al. | |
| 7,569,692 B2 | 8/2009 | Nii et al. | |
| 7,589,203 B2 | 9/2009 | Stossel et al. | |
| 7,687,155 B2 | 3/2010 | Kamatani et al. | |
| 7,709,100 B2 | 5/2010 | Kwong et al. | |
| 7,811,677 B2 | 10/2010 | Ohsawa et al. | |
| 7,883,785 B2 | 2/2011 | Stossel et al. | |
| 7,951,471 B2 | 5/2011 | Inoue et al. | |
| 7,960,038 B2 | 6/2011 | Ohsawa et al. | |
| 8,084,145 B2 | 12/2011 | Inoue et al. | |
| 8,227,600 B2 | 7/2012 | Inoue et al. | |
| 8,227,975 B2 | 7/2012 | Inoue et al. | |
| 8,247,086 B2 | 8/2012 | Inoue et al. | |
| 8,598,785 B2 | 12/2013 | Inoue et al. | |
| 8,637,167 B2 | 1/2014 | Ohsawa et al. | |
| 8,735,581 B2 | 5/2014 | Inoue et al. | |
| 8,999,520 B2* | 4/2015 | Inoue | C07F 15/0033 428/690 |
| 2001/0019782 A1 | 9/2001 | Igarashi et al. | |
| 2002/0121638 A1 | 9/2002 | Grushin et al. | |
| 2003/0054198 A1 | 3/2003 | Tsuboyama et al. | |
| 2005/0221123 A1* | 10/2005 | Inoue | C07F 15/0033 428/690 |
| 2005/0253135 A1 | 11/2005 | Stossel et al. | |
| 2006/0127696 A1 | 6/2006 | Stossel et al. | |
| 2006/0131562 A1* | 6/2006 | Li | H01L 51/002 257/40 |
| 2006/0188745 A1* | 8/2006 | Liao | H01L 51/5278 428/690 |
| 2006/0228583 A1 | 10/2006 | Kamatani et al. | |
| 2006/0240278 A1 | 10/2006 | Hatwar et al. | |
| 2007/0129545 A1 | 6/2007 | Inoue et al. | |
| 2007/0154733 A1 | 7/2007 | Fukuoka et al. | |
| 2007/0170843 A1 | 7/2007 | Kawamura et al. | |
| 2007/0244320 A1 | 10/2007 | Inoue et al. | |
| 2009/0015143 A1 | 1/2009 | Inoue et al. | |
| 2009/0184634 A1 | 7/2009 | Kamatani et al. | |
| 2009/0195153 A1 | 8/2009 | Lee et al. | |
| 2010/0145044 A1 | 6/2010 | Inoue et al. | |

FOREIGN PATENT DOCUMENTS

| | | |
|---|---|---|
| CN | 001695173 A | 11/2005 |
| DE | 102 38 903 A1 | 3/2004 |
| EP | 1 191 612 A2 | 3/2002 |
| EP | 1 211 257 A2 | 6/2002 |
| EP | 1 348 711 A1 | 10/2003 |
| EP | 1 349 435 A1 | 10/2003 |
| EP | 1 535 981 A2 | 6/2005 |
| EP | 1 873 163 A1 | 1/2008 |
| EP | 1 881 050 A2 | 1/2008 |
| EP | 1 889 891 A2 | 2/2008 |
| EP | 2 062 907 A2 | 5/2009 |
| EP | 2 254 173 A1 | 11/2010 |
| JP | 2002-105055 A | 4/2002 |
| JP | 2003-081988 A | 3/2003 |
| JP | 2003-081989 A | 3/2003 |
| JP | 2004-107441 A | 4/2004 |
| JP | 2005-158668 A | 6/2005 |
| JP | 2005-314414 A | 11/2005 |
| JP | 2005-536565 | 12/2005 |
| JP | 2006-073992 A | 3/2006 |
| JP | 2006-507279 | 3/2006 |
| JP | 2006-151887 A | 6/2006 |
| JP | 2006-188491 A | 7/2006 |
| JP | 2007-161859 A | 6/2007 |
| JP | 2007-161860 A | 6/2007 |
| KR | 10-1743998 | 6/2017 |
| TW | I423981 | 1/2014 |
| TW | I423982 | 1/2014 |
| WO | WO 2002/045466 A1 | 6/2002 |
| WO | WO 2004/037836 A1 | 5/2004 |
| WO | WO 2005/115061 A1 | 12/2005 |
| WO | WO 2006/062144 A1 | 6/2006 |

OTHER PUBLICATIONS

O'Brien, D.F. et al., "Improved Energy Transfer in Electrophosphorescent Devices," Applied Physics Letters, Jan. 18, 1999, vol. 74, No. 3, pp. 442-444.

Zhang, G.-L. et al., "Synthesis and Luminescence Property of a New Yellow Phosphorescent Iridium(III) Pyrazine Complex," Chemical Journal of Chinese Universities, Mar. 1, 2004, vol. 25, No. 3, pp. 397-400.

Tsutsui, T. et al., "High Quantum Efficiency in Organic Light-Emitting Devices With Iridium-Complex as a Triplet Emissive Center," Japanese Journal of Applied Physics, Dec. 15, 1999, vol. 38, No. 128, pp. L1502-L1504.

Baldo, M. et al., "High-Efficiency Fluorescent Organic Light-Emitting Devices Using a Phosphorescent Sensitizer," Nature, Feb. 17, 2000, vol. 403, pp. 750-753.

Thompson, M.E. et al., "Phosphorescent Materials and Devices," Proceedings of the 10th International Workshop on Inorganic and Organic Electroluminescence (EL'00), Dec. 4, 2000, pp. 35-38.

Zhang, G.-L. et al., "Synthesis and Phosphorescence of a New Iridium(III) Pyrazine Complex," Wuli Huaxue Xuebao (Acta Physico-Chimica Sinica), Oct. 19, 2003, vol. 19, No. 10, pp. 889-891.

(56) References Cited

OTHER PUBLICATIONS

Slater, J.W. et al., "Cyclometallated Nitrogen Heterocycles," Journal of Organometallic Chemistry, Aug. 29, 2003, vol. 688, pp. 112-120.
European Search Report re Application No. EP 07005200.6, dated Jul. 23, 2007.
Usyatinsky, A.Y. et al., "Microwave-Assisted Synthesis of Substituted Imidazoles on a Solid Support Under Solvent-Free Conditions," Tetrahedron Letters, 2000, vol. 41, No. 26, pp. 5031-5034.
Kidwai.M et al., "Microwave Assisted Synthesis of Novel 1,2,4-Triazines in "Dry Media"," Synthetic Communications, 2001, vol. 31, No. 11, pp. 1639-1645.
Konnno, H. et al., "Selective One-Pot Synthesis of Facial Tris-Ortho-Metalated Iridium(III) Complexes Using Microwave Irradiation," Chemistry Letters, 2003, vol. 32, No. 3, pp. 252-253, The Chemical Society of Japan.
Tsutsui, T., "Mechanism of Organic EL Element and Luminous Efficiency," Textbook of the 3rd Seminar at Division of Organic Molecular Electronics and Bioelectronics, 1993, pp. 31-37, Division of Molecular Electronics and Bioelectronics the Japan Society of Applied Physics.
Inoue, H. et al., "A Reaction of Singlet Oxygen With an Unsaturated Organic Molecule, 6.1.4, Quencher and Photosensitizer," Basic Chemistry Course Photochemistry I, Sep. 30, 1999, pp. 106-110, Maruzen.
Steel, P. et al., "Cyclometallated Compounds V. Double Cyclopalladation of Diphenyl Pyrazines and Related Ligands," Journal of Organometallic Chemistry, Oct. 2, 1990, vol. 395, No. 3, pp. 359-373.
International Search Report re Application No. PCT/JP2006/323882, dated Jan. 16, 2007.
Written Opinion re Application No. PCT/JP2006/323882, dated Jan. 16, 2007.
International Search Report re Application No. PCT/JP2006/305474, dated Apr. 11, 2006.
Written Opinion re Application No. PCT/JP2006/305474, dated Apr. 11, 2006.
Shavaleev, N.M. et al., "Sensitized Near-Infrared Emission From Complexes of YBIII, NDIII, and ERIII by Energy-Transfer From Covalently Attached PTII-Based Antena Units," Chemistry A European Journal, 2003, vol. 9, No. 21, pp. 5283-5291.
European Search Report re Application No. EP 06715702.4, dated Jul. 23, 2010.
Office Action re U.S. Appl. No. 11/092,816, dated May 20, 2010.
Declaration submitted in U.S. Appl. No. 11/092,816, dated Mar. 29, 2005.
Office Action re U.S. Appl. No. 11/607,649, dated Feb. 3, 2010.
Declaration submitted in U.S. Appl. No. 11/607,649, dated Jun. 1, 2010.
Office Action re U.S. Appl. No. 11/607,649, dated Aug. 18, 2010.
Chinese Office Action re Application No. CN 200710087859.0, dated Mar. 2, 2011.
Chinese Office Action re Application No. CN 200680045339.7, dated Feb. 24, 2011.
Izumi, T. et al., "Synthesis and Carbonylation Reaction of 2,5-Diphenylpyrazine Palladium Complex," Yamagata Daigaku Kiyo, Kogaku, Feb. 20, 1979, vol. 15, No. 2, pp. 213-218.
Xu, M.-L. et al., "Optical and Electroluminescent Properties of a New Ir(III) Complex—fac-tris[2,5-di(4-methoxyphenyl) pyridinato-C,N]iridium(III)," Thin Solid Films, Feb. 21, 2006, vol. 497, pp. 239-242.
Xu, M. et al., "Synthesis and Characterization of Phosphorescent Cyclometalated Iridium Complexes Containing 2,5-diphenylpyridine Based Ligands," Applied Organometallic Chemistry, Dec. 1, 2005, vol. 19, No. 12, pp. 1225-1231.
Yersin, H. et al., "Triplet Emitters for Organic Light-Emitting Diodes: Basic Properties," Highly Efficient OLEDs with Phosphorescent Materials, 2008, pp. 1-18.
European Office Action re Application No. EP 06715702.4, dated Jun. 24, 2011.
Taiwanese Office Action re Application No. TW 101148740, dated Apr. 8, 2013.
Taiwanese Office Action re Application No. TW 102141392, dated Jun. 5, 2014.
Chinese Office Actio re Application No. CN 201510419102.1, dated Apr. 5, 2017.
Korean Office Action re Application No. KR 2017-0067388, dated Jul. 19, 2017.

\* cited by examiner

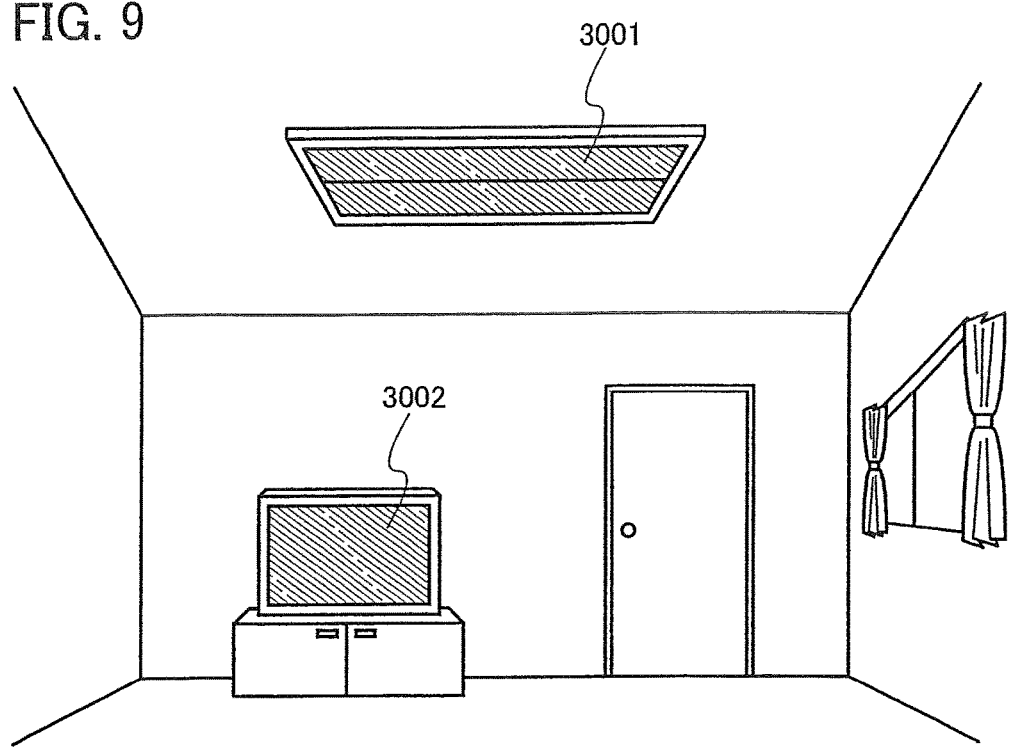

ORGANOMETALLIC COMPLEX AND LIGHT EMITTING ELEMENT, LIGHT EMITTING DEVICE, AND ELECTRONIC DEVICE USING THE ORGANOMETALLIC COMPLEX

This application is a continuation of copending U.S. application Ser. No. 11/725,971, filed on Mar. 20, 2007 which is incorporated herein by reference.

BACKGROUND OF THE INVENTION

1. Field of the Invention

The present invention relates to an organometallic complex. In particular, the present invention relates to an organometallic complex that is capable of converting a triplet excited state into luminescence. In addition, the present invention relates to a light emitting element, a light emitting device and an electronic device which use the organometallic complex.

2. Description of the Related Art

Organic compounds are brought into an excited state by absorbing light. Through this excited state, various reactions (such as photochemical reactions) are caused in some cases, or luminescence is generated in some cases. Therefore, various applications of the organic compounds have been made.

As one example of the photochemical reactions, a reaction (oxygen addition) of singlet oxygen with an unsaturated organic molecule is known (refer to Reference 1: Haruo INOUE, et al., Basic Chemistry Course PHOTOCHEMISTRY I (Maruzen Co., Ltd.), pp. 106-110, for example). Since the ground state of an oxygen molecule is a triplet state, oxygen in a singlet state (singlet oxygen) is not generated by a direct photoexcitation. However, in the presence of another triplet excited molecule, singlet oxygen is generated, which can lead to an oxygen addition reaction. In this case, a compound that can become the triplet excited molecule is referred to as a photo sensitizer.

As described above, in order to generate singlet oxygen, a photosensitizer that can become a triplet excited molecule by photoexcitation is necessary. However, since the ground state of an ordinary organic compound is a singlet state, photoexcitation to a triplet excited state is a forbidden transition, and a triplet excited molecule is not easily generated. Therefore, as such a photosensitizer, a compound in which intersystem crossing from the singlet excited state to the triplet excited state easily occurs (or a compound which allows the forbidden transition of photoexcitation directly to the triplet excited state) is required. In other words, such a compound can be used as a photosensitizer and is useful.

Also, such a compound often emits phosphorescence. The phosphorescence is luminescence generated by transition between different energies in multiplicity and, in the case of an ordinary organic compound, the phosphorescence indicates luminescence generated in returning from the triplet excited state to the singlet ground state (in contrast, luminescence in returning from a singlet excited state to the singlet ground state is referred to as fluorescence). Application fields of a compound capable of emitting phosphorescence, that is, a compound capable of converting a triplet excited state into luminescence (hereinafter, referred to as a phosphorescent compound), include a light emitting element using an organic compound as a light emitting substance.

This light emitting element has a simple structure in which a light emitting layer including an organic compound that is a light emitting substance is provided between electrodes. This light emitting element is a device attracting attention as a next-generation flat panel display element in terms of characteristics such as being thin and light in weight, high speed response, and direct current low voltage driving. In addition, a display device using this light emitting element is superior in contrast, image quality, and wide viewing angle.

The emission mechanism of a light emitting element in which an organic compound is used as a light emitting substance is a carrier injection type. Namely, by applying voltage with a light emitting layer interposed between electrodes, electrons and holes injected from the electrodes are recombined to make the light emitting substance excited, and light is emitted in returning from the excited state to the ground state. As the type of the excited state, as in the case of photoexcitation described above, a singlet excited state (S*) and a triplet excited state (T*) are possible. Further, the statistical generation ratio thereof in a light emitting element is considered to be $S^*:T^*=1:3$.

As for a compound capable of converting a singlet excited state to luminescence (hereinafter, referred to as a fluorescent compound), luminescence from a triplet excited state (phosphorescence) is not observed but only luminescence from a singlet excited state (fluorescence) is observed at a room temperature. Accordingly, the internal quantum efficiency (the ratio of generated photons to injected carriers) in a light emitting element using a fluorescent compound is assumed to have a theoretical limit of 25% based on $S^*:T^*=1:3$.

On the other hand, when the phosphorescent compound described above is used, the internal quantum efficiency can be improved to 75 to 100% in theory. Namely, a light emission efficiency that is 3 to 4 times as much as that of the fluorescence compound can be achieved. For these reasons, in order to achieve a highly-efficient light emitting element, a light emitting element using a phosphorescent compound has been developed actively (for example, refer to Reference 2: Zhang, Guo-Lin, et al., Gaodeng Xuexiao Huaxue Xuebao (2004), vol. 25, No. 3, pp. 397-400). In particular, as the phosphorescent compound, an organometallic complex using iridium or the like as a central metal has been attracting attention, owing to its high phosphorescence quantum yield.

SUMMARY OF THE INVENTION

The organometallic complex disclosed in Reference 2 can be expected to be used as a photosensitizer, since it easily causes intersystem crossing. In addition, since the organometallic complex easily generates luminescence (phosphorescence) from a triplet excited state, a highly efficient light emitting element is expected by using the organometallic complex for the light emitting element. However, in the present state, the number of types of such organometallic complexes is small.

The organometallic complex disclosed in Reference 2 emits orange-color light. When the organometallic complex is used for a full-color display, color purity as a red color is poor, which is a disadvantage in terms of color reproductivity. In contrast, in the case where the light emission color is in a dark red region; in other words, where the emission wavelength is extremely long, the organometallic complex is advantageous in terms of color reproductivity; however, the luminous efficiency (cd/A) decreases.

In consideration of the above-described problems, it is an object of the present invention to provide an organometallic complex by which red-color light emission can be obtained.

It is another object of the present invention to provide an organometallic complex with high light emission efficiency. Further, it is still another object of the present invention to provide an organometallic complex by which red-color light emission with high luminous efficiency (cd/A) can be obtained.

Furthermore, the present invention aims to provide a light emitting element with high light emission efficiency. In addition, the present invention aims to provide a light emitting element by which red-color light emission with high luminous efficiency can be obtained. Further, the present invention aims to provide a light emitting device and an electronic device with reduced power consumption.

The present inventors have made researches earnestly. As a result, the present inventors have found that a pyrazine derivative represented by the following general formula (G0) is ortho-metalated with a metal ion of Group 9 or Group 10, thereby obtaining an organometallic complex. In addition, the present inventors have also found that the organometallic complex easily causes intersystem crossing and can emit phosphorescence efficiently. Further, they have also found that the light emission color of the organometallic complex is favorable red color.

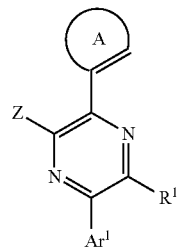

(G0)

(In the formula, A represents an aromatic hydrocarbon group having 6 to 25 carbon atoms. Further, Z represents any one of hydrogen, an alkyl group having 1 to 4 carbon atoms, an alkoxy group having 1 to 4 carbon atoms, or an aryl group having 6 to 25 carbon atoms. In addition, $A_r^1$ represents an aryl group having 6 to 25 carbon atoms. 1e represents any one of hydrogen, an alkyl group having 1 to 4 carbon atoms, or an alkoxy group having 1 to 4 carbon atoms.)

Accordingly, the structure of the present invention is an organometallic complex having a structure represented by the following general formula (G1).

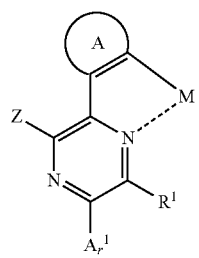

(G1)

(In the formula, A represents an aromatic hydrocarbon group having 6 to 25 carbon atoms. Further, Z represents any one of hydrogen, an alkyl group having 1 to 4 carbon atoms, an alkoxy group having 1 to 4 carbon atoms, or an aryl group having 6 to 25 carbon atoms. In addition, $A_r^1$ represents an aryl group having 6 to 25 carbon atoms. $R^1$ represents any one of hydrogen, an alkyl group having 1 to 4 carbon atoms, or an alkoxy group having 1 to 4 carbon atoms. Further, M is a central metal and represents an element belonging to Group 9 or Group 10.)

In the case where Z in the above general formula (G0) is an aryl group, the organometallic complex of the present invention has a structure represented by the following general formula (G2). Accordingly, another structure of the present invention is an organometallic complex having the structure represented by the following general formula (G2).

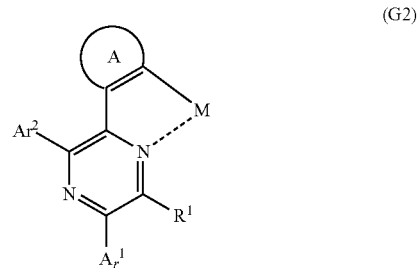

(G2)

(In the formula, A represents an aromatic hydrocarbon group having 6 to 25 carbon atoms. Further, each of $A_r^1$ and $A_r^2$ represents an aryl group having 6 to 25 carbon atoms. $R^1$ represents any one of hydrogen, an alkyl group having 1 to 4 carbon atoms, or an alkoxy group having 1 to 4 carbon atoms. Further, M is a central metal and represents an element belonging to Group 9 or Group 10.)

When the organometallic complex of the present invention is evaporated for the purpose of sublimation, purification, or the like, it is preferable to use a substituted or unsubstituted 1,2-phenylene group as the aromatic hydrocarbon group A in the above general formula (G2), since the use of the substituted or unsubstitued 1,2-phenylene group can suppress the increase of the evaporation temperature due to the increase of molecular weight. In this case, a substituted or unsubstituted phenyl group is preferably used as $A_r^2$ for ease of synthesis. Accordingly, a preferable structure of the present invention is an organometallic complex having a structure represented by the following general formula (G3).

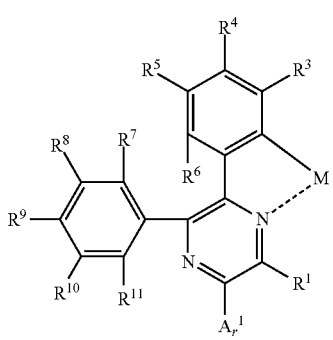

(G3)

(In the formula, $A_r^1$ represents an aryl group having 6 to 25 carbon atoms. $R^1$ represents any one of hydrogen, an alkyl group having 1 to 4 carbon atoms, or an alkoxy group having 1 to 4 carbon atoms. Further, each of $R^3$ to $R^{11}$ represents any one of hydrogen, an alkyl group having 1 to 4 carbon atoms, an alkoxy group having 1 to 4 carbon atoms, an aryl group having 6 to 12 carbon atoms, a halogen group, or a trifluoromethyl group. Further, M is a central metal and represents an element belonging to Group 9 or Group 10.)

Further, a favorable structure of the above general formula (G2) can be obtained when the aromatic hydrocarbon group A is an unsubstituted phenylen group. In this case, an unsubstituted phenyl group is preferably used for $A_r^2$ for ease of synthesis. Accordingly, a more preferable structure of the present invention is an organometallic complex having a structure represented by the following general formula (G4).

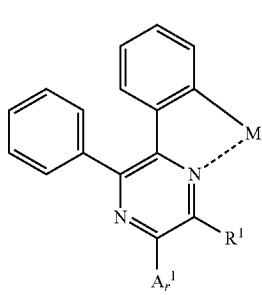

(G4)

(In the formula, $A_r^1$ represents an aryl group having 6 to 25 carbon atoms. $R^1$ represents any one of hydrogen, an alkyl group having 1 to 4 carbon atoms, or an alkoxy group having 1 to 4 carbon atoms. Further, M is a central metal and represents an element belonging to Group 9 or Group 10.)

Further, when $A_r^1$ is a substituted or unsubstituted phenyl group in the general formula (G4), red-color light emission with excellent color purity and high luminous efficiency (cd/A) can be obtained. Accordingly, a further preferable structure of the present invention is an organometallic complex having a structure represented by the following general formula (G5).

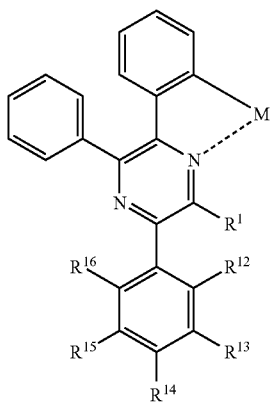

(G5)

(In the formula, $R^1$ represents any one of hydrogen, an alkyl group having 1 to 4 carbon atoms, or an alkoxy group having 1 to 4 carbon atoms. Further, each of $R^{12}$ to $R^{16}$ represents any one of hydrogen, an alkyl group having 1 to 4 carbon atoms, an alkoxy group having 1 to 4 carbon atoms, an aryl group having 6 to 12 carbon atoms, a halogen group, or a trifluoromethyl group. Further, M is a central metal and represents an element belonging to Group 9 or Group 10.)

In the general formula (G5), hydrogen, a fluoro group, or a trifluoromethyl group is preferable as each of $R^{12}$ to $R^{16}$.

By taking such a structure, red-color light emission having a chromaticity near the red-color chromaticity set by NTSC (National Television Standards Committee) (i.e., (x, y)= (0.67, 0.33)) can be obtained.

Next, in the case where Z in the above general formula (G0) is hydrogen, an alkyl group, or an alkoxy group, the organometallic complex of the present invention has a structure represented by the following general formula (G6). Accordingly, another structure of the present invention is an organometallic complex having the structure represented by the following general formula (G6).

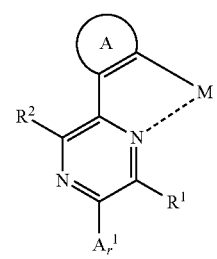

(G6)

(In the formula, A represents an aromatic hydrocarbon group having 6 to 25 carbon atoms. $A_r^1$ represents an aryl group having 6 to 25 carbon atoms. Each of $R^1$ and $R^2$ represents any one of hydrogen, an alkyl group having 1 to 4 carbon atoms, or an alkoxy group having 1 to 4 carbon atoms. Further, M is a central metal and represents an element belonging to Group 9 or Group 10.)

When the organometallic complex of the present invention is evaporated for the purpose of sublimation, purification, or the like, it is preferable to use a substituted or unsubstituted 1,2-phenylene group as the aromatic hydrocarbon group A in the above general formula (G6), since the use of the substituted or unsubstitued 1,2-phenylene group can suppress the increase of the evaporation temperature due to the increase of molecular weight. Accordingly, a preferable structure of the present invention is an organometallic complex having a structure represented by the following general formula (G7).

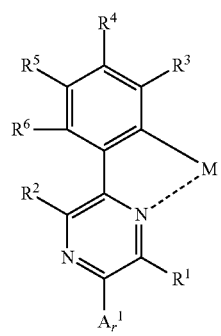

(G7)

(In the formula, $A_r^1$ represents an aryl group having 6 to 25 carbon atoms. Each of $R^1$ and $R^2$ represents any one of hydrogen, an alkyl group having 1 to 4 carbon atoms, or an alkoxy group having 1 to 4 carbon atoms. Further, each of $R^3$ to $R^6$ represents any one of hydrogen, an alkyl group having 1 to 4 carbon atoms, an alkoxy group having 1 to 4 carbon atoms, an aryl group having 6 to 12 carbon atoms, a halogen group, or a trifluoromethyl group. Further, M is a central metal and represents an element belonging to Group 9 or Group 10.)

Further, a favorable structure of the above general formula (G6) can be obtained when the aromatic hydrocarbon group A is an unsubstituted phenylen group. Accordingly, a more preferable structure of the present invention is an organometallic complex having a structure represented by the following general formula (G8).

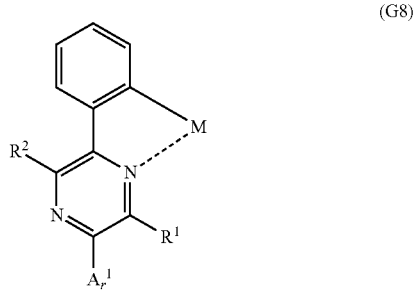

(G8)

(In the formula, $A_r^1$ represents an aryl group having 6 to 25 carbon atoms. Each of $R^1$ and $R^2$ represents any one of hydrogen, an alkyl group having 1 to 4 carbon atoms, or an alkoxy group having 1 to 4 carbon atoms. Further, M is a central metal and represents an element belonging to Group 9 or Group 10.)

Further, when $A_r^1$ is a substituted or unsubstituted phenyl group in the general formula (G8), red-color light emission with excellent color purity and high luminous efficiency (cd/A) can be obtained. Accordingly, a further preferable structure of the present invention is an organometallic complex having a structure represented by the following general formula (G9).

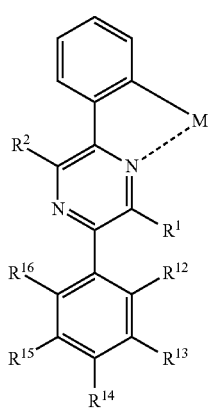

(G9)

(In the formula, each of $R^1$ and $R^2$ represents any one of hydrogen, an alkyl group having 1 to 4 carbon atoms, or an alkoxy group having 1 to 4 carbon atoms. Further, each of $R^{12}$ to $R^{16}$ represents any one of hydrogen, an alkyl group having 1 to 4 carbon atoms, an alkoxy group having 1 to 4 carbon atoms, an aryl group having 6 to 12 carbon atoms, a halogen group, or a trifluoromethyl group. Further, M is a central metal and represents an element belonging to Group 9 or Group 10.)

In the general formula (G9), hydrogen, a fluoro group, or a trifluoromethyl group is preferable as each of $R^{12}$ to $R^{16}$.

By taking such a structure, red-color light emission having a chromaticity near the red-color chromaticity set by NTSC (National Television Standards Committee) (i.e., (x, y)= (0.67, 0.33)) can be obtained.

When hydrogen or a methyl group is used as $R^1$ in the pyrazine derivative represented by the above general formula (G0), steric hindrance of the pyrazine derivative is reduced and the pyrazine derivative is easily ortho-metalated with a metal ion, which is preferable in terms of a synthesis yield. Accordingly, a preferable structure of the present invention is an organometallic complex having a structure represented by any of the general formulae (G1) to (G9), in which $R^1$ is hydrogen or a methyl group.

Here, as the organometallic complex having the structure represented by the above general formula (G1), an organometallic complex represented by the following general formula (G10) is more specifically preferable because it can be easily synthesized.

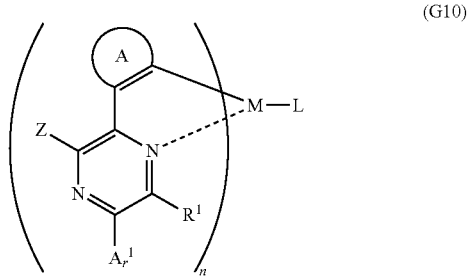

(G10)

(In the formula, A represents an aromatic hydrocarbon group having 6 to 25 carbon atoms. Further, Z represents any one of hydrogen, an alkyl group having 1 to 4 carbon atoms, an alkoxy group having 1 to 4 carbon atoms, or an aryl group having 6 to 25 carbon atoms. In addition, $A_r^1$ represents an aryl group having 6 to 25 carbon atoms. $R^1$ represents any one of hydrogen, an alkyl group having 1 to 4 carbon atoms, or an alkoxy group having 1 to 4 carbon atoms. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

As the organometallic complex having the structure represented by the above general formula (G2), an organometallic complex represented by the following general formula (G11) is preferable because it can be easily synthesized.

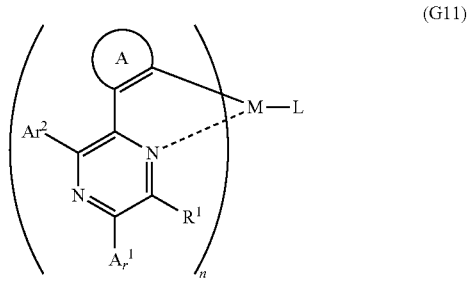

(G11)

(In the formula, A represents an aromatic hydrocarbon group having 6 to 25 carbon atoms. Further, each of $A_r^1$ and $A_r^2$ represents an aryl group having 6 to 25 carbon atoms. $R^1$ represents any one of hydrogen, an alkyl group having 1 to 4 carbon atoms, or an alkoxy group having 1 to 4 carbon atoms. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

As the organometallic complex having the structure represented by the above general formula (G3), an organometallic complex represented by the following general formula (G12) is preferable because it can be easily synthesized.

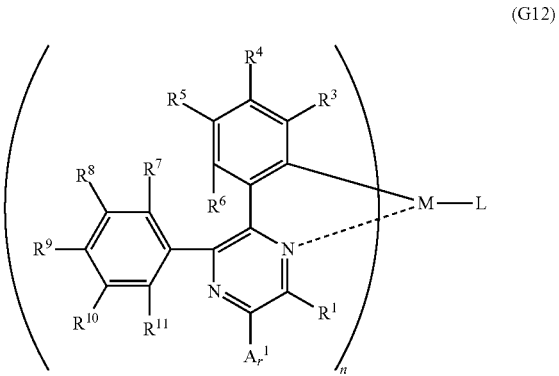

(G12)

(In the formula, $A_r^1$ represents an aryl group having 6 to 25 carbon atoms. $R^1$ represents any one of hydrogen, an alkyl group having 1 to 4 carbon atoms, or an alkoxy group having 1 to 4 carbon atoms. Further, each of $R^3$ to $R^{11}$ represents any one of hydrogen, an alkyl group having 1 to 4 carbon atoms, an alkoxy group having 1 to 4 carbon atoms, an aryl group having 6 to 12 carbon atoms, a halogen group, or a trifluoromethyl group. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

As the organometallic complex having the structure represented by the above general formula (G4), an organometallic complex represented by the following general formula (G13) is specifically preferable because it can be easily synthesized.

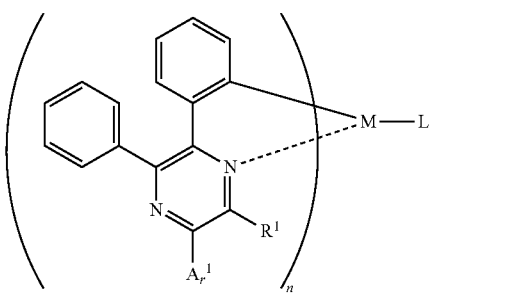

(G13)

(In the formula, $A_r^1$ represents an aryl group having 6 to 25 carbon atoms. $R^1$ represents any one of hydrogen, an alkyl group having 1 to 4 carbon atoms, or an alkoxy group having 1 to 4 carbon atoms. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

As the organometallic complex having the structure represented by the above general formula (G5), an organometallic complex represented by the following general formula (G14) is specifically preferable because it can be easily synthesized.

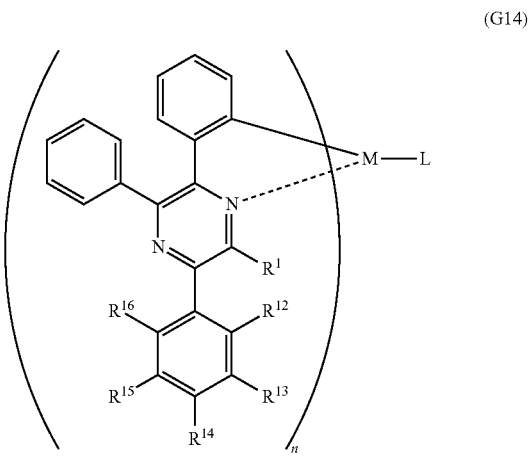

(G14)

(In the formula, $R^1$ represents any one of hydrogen, an alkyl group having 1 to 4 carbon atoms, or an alkoxy group having 1 to 4 carbon atoms. Further, each of $R^{12}$ to $R^{16}$ represents any one of hydrogen, an alkyl group having 1 to 4 carbon atoms, an alkoxy group having 1 to 4 carbon atoms, an aryl group having 6 to 12 carbon atoms, a halogen group, or a trifluoromethyl group. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

In the general formula (G14), hydrogen, a fluoro group, or a trifluoromethyl group is preferable as each of $R^{12}$ to $R^{16}$. By taking such a structure, red-color light emission having a chromaticity near the red-color chromaticity set by NTSC (National Television Standards Committee) (i.e., (x, y)= (0.67, 0.33)) can be obtained.

As the organometallic complex having the structure represented by the above general formula (G6), an organometallic complex represented by the following general formula (G15) is specifically preferable because it can be easily synthesized.

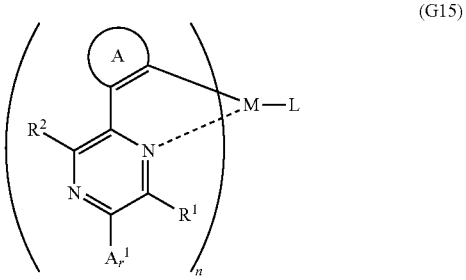

(G15)

(In the formula, A represents an aromatic hydrocarbon group having 6 to 25 carbon atoms. $A_r^1$ represents an aryl group having 6 to 25 carbon atoms. Each of $R^1$ and $R^2$ represents any one of hydrogen, an alkyl group having 1 to 4 carbon atoms, or an alkoxy group having 1 to 4 carbon atoms. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

As the organometallic complex having the structure represented by the above general formula (G7), an organometallic complex represented by the following general formula (G16) is specifically preferable because it can be easily synthesized.

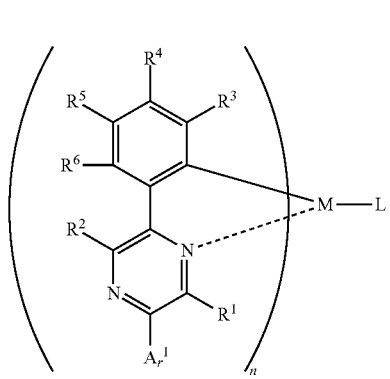

(G16)

(In the formula, $A_r^1$ represents an aryl group having 6 to 25 carbon atoms. Each of $R^1$ and $R^2$ represents any one of hydrogen, an alkyl group having 1 to 4 carbon atoms, or an alkoxy group having 1 to 4 carbon atoms. Further, each of $R^3$ to $R^6$ represents any one of hydrogen, an alkyl group having 1 to 4 carbon atoms, an alkoxy group having 1 to 4 carbon atoms, an aryl group having 6 to 12 carbon atoms, a halogen group, or a trifluoromethyl group. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

As the organometallic complex having the structure represented by the above general formula (G8), an organometallic complex represented by the following general formula (G17) is specifically preferable because it can be easily synthesized.

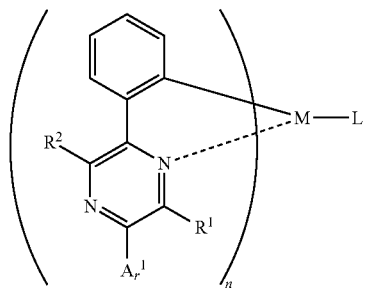

(G17)

(In the formula, $A_r^1$ represents an aryl group having 6 to 25 carbon atoms. Each of $R^1$ and $R^2$ represents any one of hydrogen, an alkyl group having 1 to 4 carbon atoms, or an alkoxy group having 1 to 4 carbon atoms. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

As the organometallic complex having the structure represented by the above general formula (G9), an organometallic complex represented by the following general formula (G18) is specifically preferable because it can be easily synthesized.

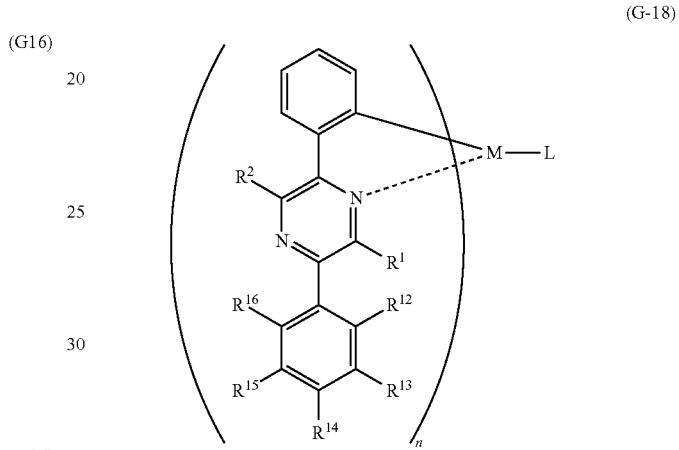

(G-18)

(In the formula, each of $R^1$ and $R^2$ represents any one of hydrogen, an alkyl group having 1 to 4 carbon atoms, or an alkoxy group having 1 to 4 carbon atoms. Further, each of $R^{12}$ to $R^{16}$ represents any one of hydrogen, an alkyl group having 1 to 4 carbon atoms, an alkoxy group having 1 to 4 carbon atoms, an aryl group having 6 to 12 carbon atoms, a halogen group, or a trifluoromethyl group. Further, M is a central metal and represents an element belonging to Group 9 or Group 10. L represents a monoanionic ligand. In addition, n is 2 when the central metal is an element belonging to Group 9, and n is 1 when the central metal is an element belonging to Group 10.)

In the general formula (G18), hydrogen, a fluoro group, or a trifluoromethyl group is preferable as each of $R^{12}$ to $R^{16}$. By taking such a structure, red-color light emission having a chromaticity near the red-color chromaticity set by NTSC (National Television Standards Committee) (i.e., (x, y)= (0.67, 0.33)) can be obtained.

When hydrogen or a methyl group is used as $R^1$ in the pyrazine derivative represented by the above general formula (G0), steric hindrance of the pyrazine derivative is reduced and the pyrazine derivative is easily ortho-metalated with a metal ion, which is preferable in terms of a synthesis yield. Accordingly, a preferable structure of the present invention is an organometallic complex represented by any of the above general formulae (G10) to (G18), in which $R^1$ is hydrogen or a methyl group.

The above-mentioned monoanionic ligand L is preferably either a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen, because these ligands have high coordinating ability. More preferably, the monoanionic ligand L is a monoanionic ligand represented by the following structural formulae (L1) to (L8). Since these ligands have high coordinating ability and can be obtained at low price, they are useful.

(L1)
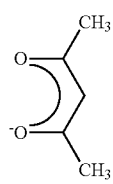

(L2)
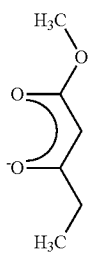

(L3)
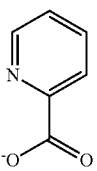

(L4)
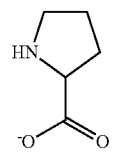

(L5)
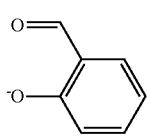

(L6)
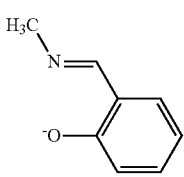

(L7)
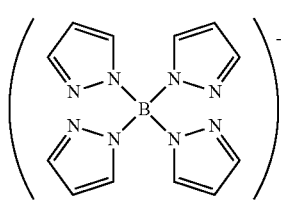

-continued (L8)
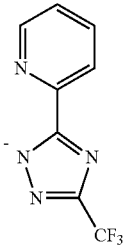

In order to emit phosphorescence more efficiently, a heavy metal is preferable as a central metal in terms of heavy atom effect. Therefore, one feature of the present invention is that iridium or platinum is employed as the central metal M in each of the above organometallic complexes of the present invention. Particularly when the central metal M is iridium, heat resistance of the organometallic complex is improved. Therefore, iridium is particularly preferable as the central metal M.

In the organometallic complex having the structure represented by any of the above general formulae (G1) to (G9) (in other words, including the organometallic complexes represented by the above general formulae (G10) to (G18)), the coordinate structure in which the pyrazine derivative represented by the general formula (G0) is ortho-metalated with a metal ion, contributes emission of phosphorescence greatly. Therefore, another structure of the present invention is a light emitting material including an organometallic complex as described above.

In addition, the organometallic complex of the present invention is very effective. Because the organometallic complex of the present invention can emit phosphorescence; in other words, a triplet excitation energy can be converted into light, high efficiency can be obtained by applying the organometallic complex to a light emitting element. Therefore, the present invention includes a light emitting element using the organometallic complex of the present invention.

At this time, the organometallic complex of the present invention is effective when it is used for a light emitting substance in terms of light emission efficiency. Therefore, one feature of the present invention is a light emitting element using the organometallic complex of the present invention as a light emitting substance. A light emitting element having a structure in which a light emitting layer is provided between a pair of electrodes and an organometallic complex of the present invention is dispersed in a metal complex is preferable. Further, the metal complex is preferably a zinc complex.

The thus obtained light emitting element of the present invention can realize high light emission efficiency, and thus, a light emitting device (such as an image display device or a light emitting device) using this light emitting element can realize low power consumption. Accordingly, the present invention includes a light emitting device and an electronic device using the light emitting element of the present invention.

One feature of the light emitting device of the present invention is to include a layer containing a light emitting substance between a pair of electrodes, in which the layer containing the light emitting substance includes a light emitting element containing the above-described organometallic complex and a control means which controls light emission of the light emitting element. In this specification, the term "light emitting device" refers to an image display device or a light emitting device including a light emitting element. Further, the category of the light emitting device includes a module including a light emitting element attached with a connector such as a module attached with an anisotropic conductive film, TAB (Tape Automated Bonding) tape, or a TCP (Tape Carrier Package); a module in which an end of the TAB tape or the TCP is provided with a printed wiring board; or a module in which an IC (Integrated Circuit) is directly mounted on a light emitting element by COG (Chip On Glass); and the like. Further, the category includes a light emitting device used for lighting equipment and the like.

One feature of an electronic device of the present invention is to include a display portion, and the display portion includes the above-described light emitting element and the control means which controls light emission of the light emitting element.

With the use of an organometallic complex of the present invention, red-color light emission can be obtained. Further, the organometallic complex of the present invention is an organometallic complex with high light emission efficiency. In addition, red-color light emission with high luminous efficiency (cd/A) can be obtained.

Further, when a light emitting element is manufactured with the use of the organometallic complex of the present invention, the light emitting element can have high light emission efficiency. Further, red-color light emission with high luminous efficiency can be obtained.

Further, the usage of the organometallic complex of the present invention enables a light emitting device and an electronic device with reduced power consumption to be provided.

BRIEF DESCRIPTION OF DRAWINGS

In the accompanying drawings:

FIG. 9 shows a lighting device of the present invention;

DETAILED DESCRIPTION OF THE INVENTION

Figure 1:
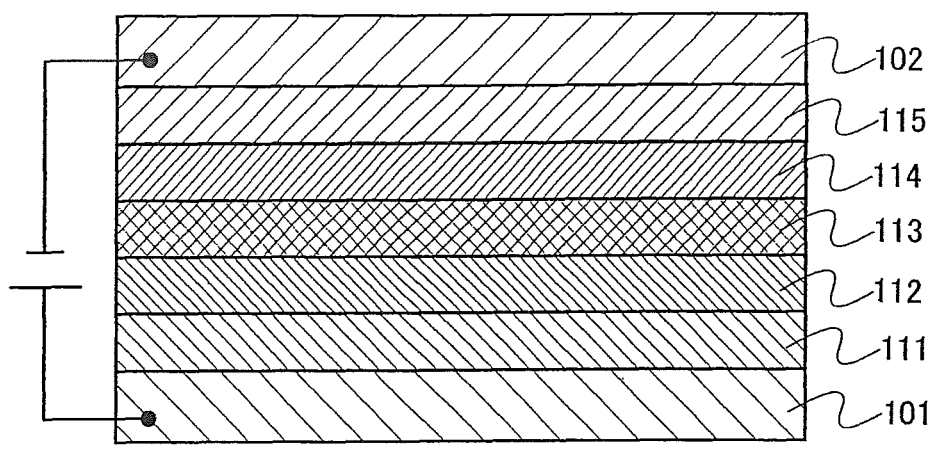
FIG. 1 shows a light emitting element of the present invention.

Hereinafter, embodiment modes and examples of the present invention will be described with reference to the drawings. Note that the present invention can be carried out in many various modes. It is easily understood by those skilled in the art that various changes may be made in forms and details without departing from the spirit and the scope of the present invention. Therefore, the present invention should not be limited to the description of the embodiment modes and examples below.

Embodiment Mode 1

Embodiment Mode 1 will describe an organometallic complex of the present invention.

<Synthetic Method of a Pyrazine Derivative Represented by the General Formula (G0)>

An organometallic complex of the present invention is formed by ortho metalation of a pyrazine derivative represented by the following general formula (G0) with a metal ion belonging to Group 9 or Group 10.

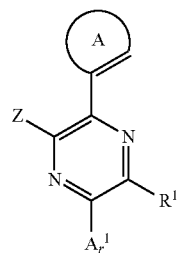

(G0)

(In the formula, A represents an aromatic hydrocarbon group having 6 to 25 carbon atoms. Further, Z represents any one of hydrogen, an alkyl group having 1 to 4 carbon atoms, an alkoxy group having 1 to 4 carbon atoms, or an aryl group having 6 to 25 carbon atoms. In addition, $A_r^1$ represents an aryl group having 6 to 25 carbon atoms. $R^1$ represents any one of hydrogen, an alkyl group having 1 to 4 carbon atoms, or an alkoxy group having 1 to 4 carbon atoms.)

Hereinafter, synthetic methods of the pyrazine derivative represented by the general formula (G0) in each of the cases where Z in the general formula (G0) is an aryl group (the following general formula (G0-1)) and where Z is hydrogen, an alkyl group, or an alkoxy group (the following general formula (G0-2)) will be described.

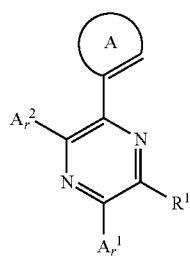

(G0-1)

(In the formula, A represents an aromatic hydrocarbon group having 6 to 25 carbon atoms. Further, each of $A_r^1$ and $A_r^2$ represents an aryl group having 6 to 25 carbon atoms. $R^1$ represents any one of hydrogen, an alkyl group having 1 to 4 carbon atoms, or an alkoxy group having 1 to 4 carbon atoms.)

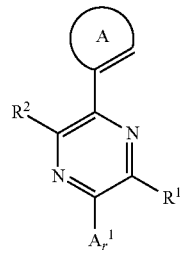

(G0-2)

(In the formula, A represents an aromatic hydrocarbon group having 6 to 25 carbon atoms. Further, $A_r^1$ represents an aryl group having 6 to 25 carbon atoms. Each of $R^1$ and $R^2$ represents any one of hydrogen, an alkyl group having 1 to 4 carbon atoms, or an alkoxy group having 1 to 4 carbon atoms.)

First, the pyrazine derivative represented by the general formula (G0-1) can be synthesized by the following simple synthetic scheme. For example, the pyrazine derivative can be obtained by reacting a pyrazine derivative (A1) with aryllithium compound or arylmagnesium bromide compound (A2) as shown in the following scheme (a). Alternatively, the pyrazine derivative can be obtained by reacting a pyrazine derivative (A1') with aryllithium compound or arylmagnesium bromide compound (A2') as shown in the following scheme (a').

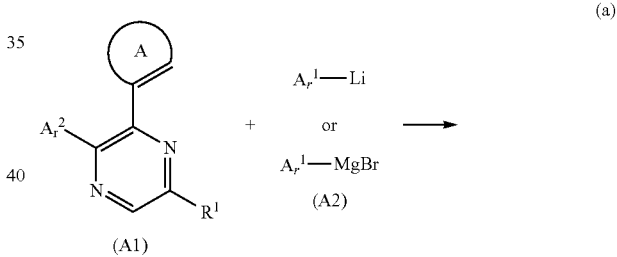

(a)

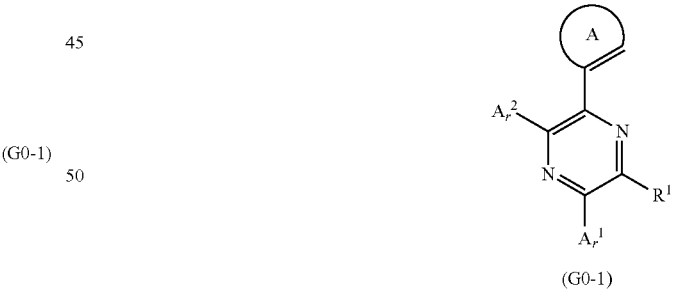

(G0-1)

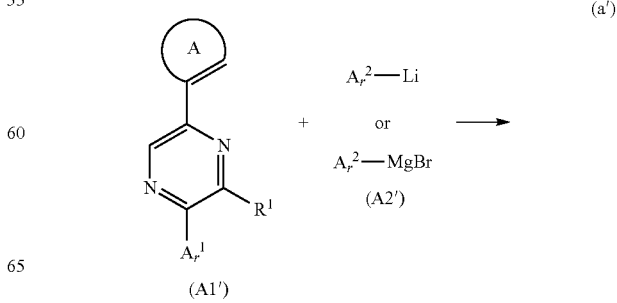

(a')

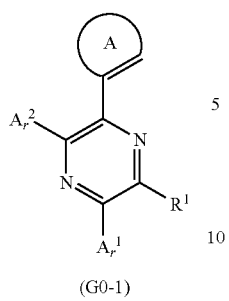

(G0-1)

On the other hand, the pyrazine derivative represented by the general formula (G0-2) can be synthesized by the following simple synthetic scheme. For example, the pyrazine derivative can be obtained by reacting a pyrazine derivative (A1″) with aryllithium compound or arylmagnesium bromide compound (A2″) as shown in the following scheme (a″). Alternatively, in the case where A=$A_r^1$ and $R^1$=$R^2$=H, the pyrazine derivative can be obtained by treating α-haloketone (the following structural formula (A3)) of arene with the use of $NH_3$ and through self-condensation of α-aminoketone of arene. Note that X in the structural formula (A3) represents a halogen element.

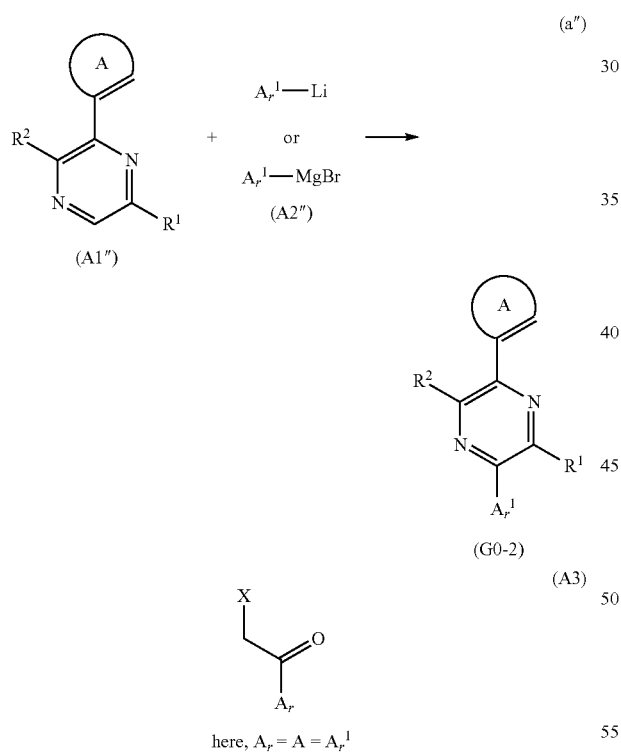

Since various kinds of the above-described compounds (A1), (A2), (A1'), (A2'), (A1″), (A2″), and (A3) are available commercially or can be synthesized, many kinds of the pyrazine derivative represented by the above-described general formula (G0) can be synthesized.

<Synthetic Method of an Organometallic Complex of the Present Invention Having a Structure Represented by the General Formula (G1)>

Next, an organometallic complex of the present invention which is formed by ortho metalation of the pyrazine derivative represented by the general formula (G0), i.e., the organometallic complex having the structure represented by the following general formula (G1) will be described.

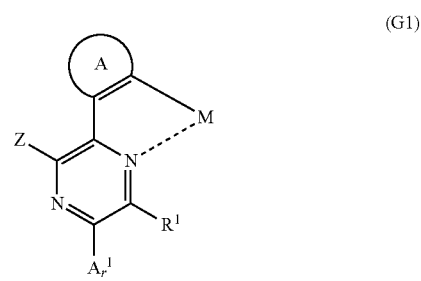

(G1)

(In the formula, A represents an aromatic hydrocarbon group having 6 to 25 carbon atoms. Further, Z represents any one of hydrogen, an alkyl group having 1 to 4 carbon atoms, an alkoxy group having 1 to 4 carbon atoms, or an aryl group having 6 to 25 carbon atoms. $A_r^1$ represents an aryl group having 6 to 25 carbon atoms. In addition, $R^1$ represents any one of hydrogen, an alkyl group having 1 to 4 carbon atoms, or an alkoxy group having 1 to 4 carbon atoms. M is a central metal and represents an element belonging to Group 9 or Group 10.)

First, as shown in the following synthetic scheme (b), the pyrazine derivative represented by the general formula (G0) and a compound of a metal belonging to Group 9 or Group 10 and including halogen (such as a metal halide or metal complex) are heated in an appropriate solvent, thereby obtaining a dinuclear complex (B) which is a kind of organometallic complex of the present invention having the structure represented by the general formula (G1). As a compound of a metal belonging to Group 9 or Group 10 and including halogen, there are rhodium chloride hydrate, palladium chloride, iridium chloride hydrate, iridium chloride hydrate hydrochloride, potassium tetrachloroplatinate(II), and the like; however, the present invention is not limited to these examples. In the scheme (b), M denotes an element belonging to Group 9 or Group 10, and X denotes a halogen element. In addition, n is 2 when M is an element belonging to Group 9, and n is 1 when M is an element belonging to Group 10.

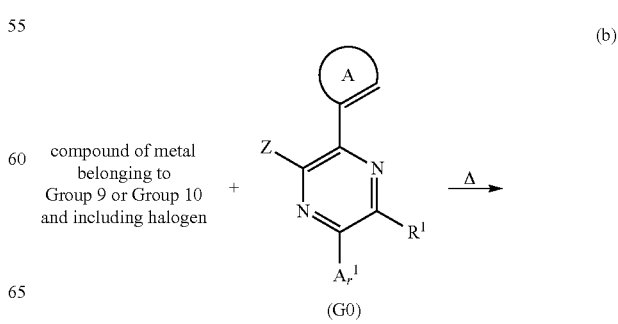

(b)

-continued

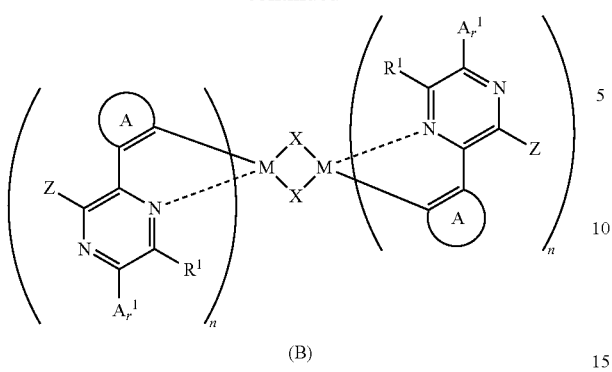

(B)

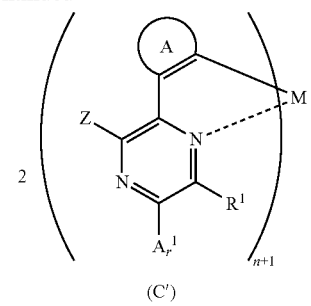

(C')

Further, as shown in the following synthetic scheme (c'), the dinuclear complex (B) and the pyrazine derivative represented by the general formula (G0) are heated at a high temperature of about 200° C. in a high boiling solvent of glycerol or the like, and thus, one type (C') of organometallic complex of the present invention having the structure represented by the general formula (G1) can be obtained. As shown in the following synthetic scheme (c"), a dinuclear complex (B) and a compound which can be ortho-metalated, such as phenylpyridine (more generally, a compound which can be cyclo-metalated) are heated at a high temperature of about 200° C. in a high boiling solvent of glycerol or the like, and thus, one type (C") of organometallic complex of the present invention having the structure represented by the general formula (G1) can be obtained. In the schemes (c') and (c"), M denotes an element belonging to Group 9 or Group 10, and X denotes a halogen element. In addition, n is 2 when M is an element belonging to Group 9, and n is 1 when M is an element belonging to Group 10.

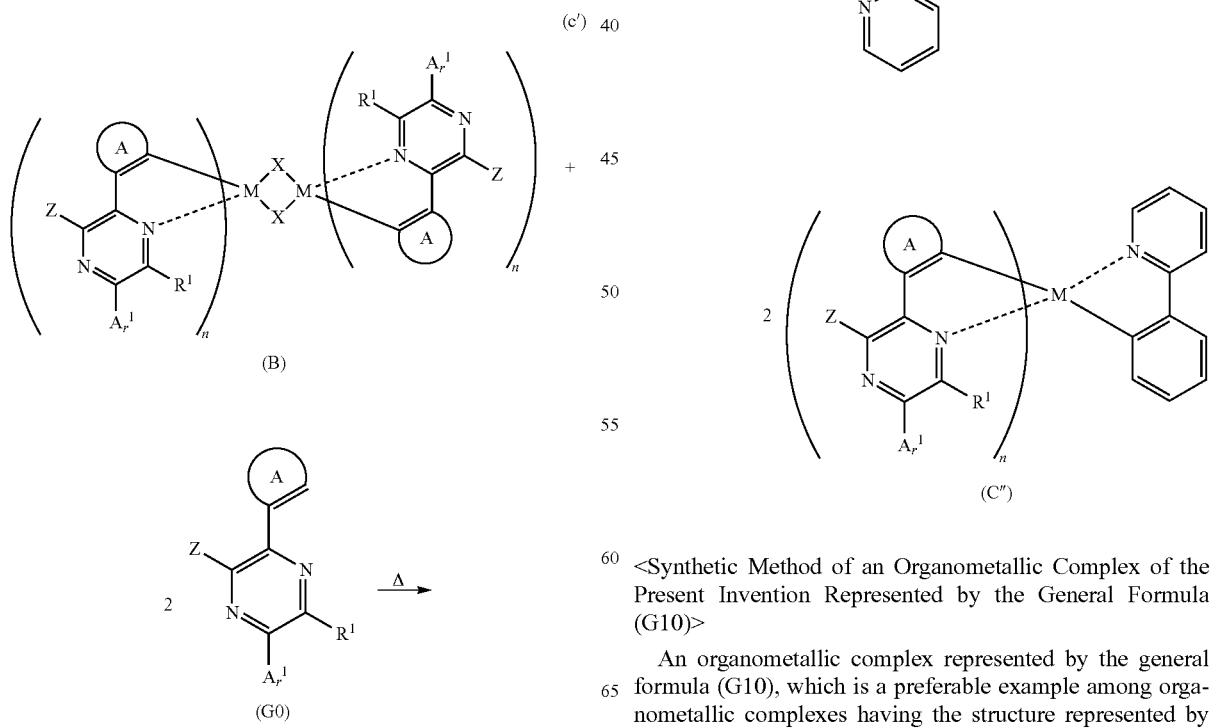

<Synthetic Method of an Organometallic Complex of the Present Invention Represented by the General Formula (G10)>

An organometallic complex represented by the general formula (G10), which is a preferable example among organometallic complexes having the structure represented by the above general formula (G1), will be described.

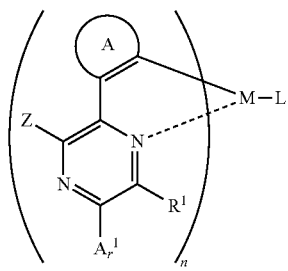

(G10)

(In the formula, A represents an aromatic hydrocarbon group having 6 to 25 carbon atoms. Further, Z represents any one of hydrogen, an alkyl group having 1 to 4 carbon atoms, an alkoxy group having 1 to 4 carbon atoms, or an aryl group having 6 to 25 carbon atoms. $A_r^1$ represents an aryl group having 6 to 25 carbon atoms. Further, $R^1$ represent any one of hydrogen, an alkyl group having 1 to 4 carbon atoms, or an alkoxy group having 1 to 4 carbon atoms. M is a central metal, and denotes an element belonging to Group 9 or Group 10. L represents a monoanionic ligand. In addition, n is 2 when M is an element belonging to Group 9, and n is 1 when M is an element belonging to Group 10.)

The organometallic complex of the present invention represented by the above general formula (G10) can be synthesized by the following scheme (c). In other words, the dinuclear complex (B) obtained by the above scheme (b) is reacted with HL which is a material of a monoanionic ligand L, and a proton of HL is separated and coordinated to the central metal M. In this manner, the organometallic complex of the present invention represented by the general formula (G10) can be obtained. In the scheme (c), M denotes an element belonging to Group 9 or Group 10, and X denotes a halogen element. In addition, n is 2 when M is an element belonging to Group 9, and n is 1 when M is an element belonging to Group 10.

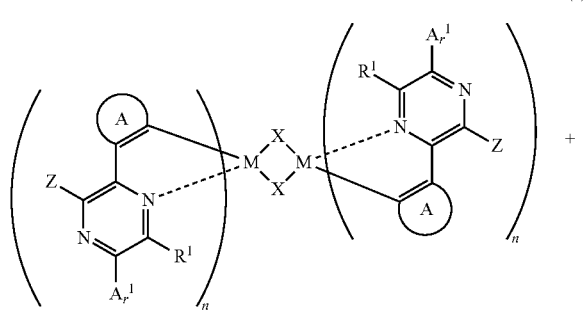

(c)

(B)

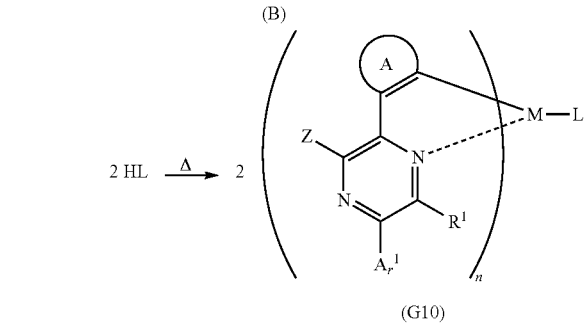

(G10)

<Specific Structural Formulae of the Organometallic Complex of the Present Invention Having the Structure Represented by the General Formula (G1) and the Organometallic Complex of the Present Invention Represented by the General Formula (G10)>

Next, specific structural formulae of the organometallic complex of the present invention having the structure represented by the general formula (G1) and the organometallic complex of the present invention represented by the general formula (G10) will be described.

The central metal M is selected from elements belonging to Group 9 or Group 10; however, iridium(III) or platinum (II) is preferable in terms of light emission efficiency. In particular, iridium(III) is preferably used since it is thermally stable.

Then, a ligand portion P surrounded by the broken line in the following general formula (G1) and (G10) will be described. As described above, M denotes an element belonging to Group 9 or Group 10. L represents a monoanionic ligand (specific examples are described below). In addition, n is 2 when M is an element belonging to Group 9, and n is 1 when M is an element belonging to Group 10.

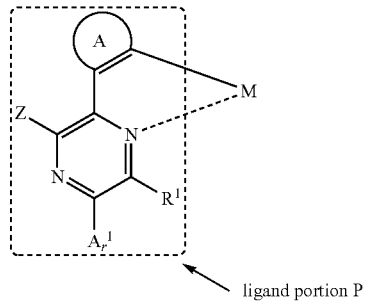

ligand portion P

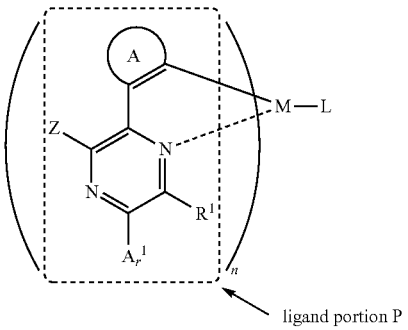

ligand portion P

As specific examples of the aromatic hydrocarbon group A, there are substituted or unsubstituted 1,2-phenylene group, 1,2-naphthylene group, 2-3-naphthylene group, spirofluorene-2,3-diyl group, 9,9-dialkylfluorene-2,3-diyl group such as a 9,9-dimethylfluorene-2,3-diyl group, and the like. In particular, when the organometallic complex of the present invention is evaporated for the purpose of sublimation, purification, or the like, it is effective to use a substituted or unsubstituted 1,2-phenylene group as the aromatic hydrocarbon group A, since the use of the substituted or unsubstitued 1,2-phenylene group can suppress the increase of the evaporation temperature due to the increase of molecular weight. In the case where the 1,2-phenylene group has a substituent, the substituent is specifically an alkyl group such as a methyl group, an ethyl group, an isopropyl group, or a tert-butyl group; an alkoxy group such as a methoxy group, an ethoxy group, an isopropoxy group, or a tert-butoxy group; an aryl group such as a phenyl group or a 4-biphenylyl group; a halogen group such as a fluoro group; or a trifluoromethyl group. Note that the unsubstituted 1,2-phenylene group is particularly preferable among the examples as the aromatic hydrocarbon group A.

As specific examples of the substituent Z, there are various aryl groups such as substituted or unsubstituted phenyl group, 1-naphthyl group, 2-naphthyl group, spiro-fluorene-2-yl group, and 9,9-dialkylfluorene-2-yl group such as 9,9-dimethylfluorene-2-yl group. In particular, when the organometallic complex of the present invention is evaporated for the purpose of sublimation, purification, or the like, it is effective to use a substituted or unsubstituted phenyl group as the substituent Z, since the use of the substituted or unsubstitued phenyl group can suppress the increase of the evaporation temperature due to the increase of molecular weight. In the case where the phenyl group has a substituent, the substituent is specifically an alkyl group such as a methyl group, an ethyl group, an isopropyl group, or a tert-butyl group; an alkoxy group such as a methoxy group, an ethoxy group, an isopropoxy group, or a tert-butoxy group; an aryl group such as a phenyl group or a 4-biphenylyl group; a halogen group such as a fluoro group; or a trifluoromethyl group. In the case where an aryl group is used as the substituent Z, an unsubsituted phenyl group is particularly preferable among the specific examples. The substituent Z may also be an alkyl group such as a methyl group, an ethyl group, an isopropyl group, a tert-butyl group; or an alkoxy group such as a methoxy group, an ethoxy group, an isopropoxy group, or a tert-butoxy group. Further, the substituent Z may also be hydrogen.

As specific examples of the aryl group $A_r^1$, there are substituted or unsubstituted a phenyl group, a 1-naphthyl group, a 2-naphthyl group, a spirofluorene-2-yl group, a 9,9-dialkylfluorene-2-yl group such as a 9,9-dimethylfluorene-2-yl group, and the like. Particularly when a substituted or unsubstituted phenyl group is used as the aryl group $A_r^1$, red-color light emission with excellent color purity and high luminous efficiency (cd/A) can be obtained. In the case where the phenyl group has a substituent, the substituent may be specifically an alkyl group such as a methyl group, an ethyl group, an isopropyl group, a tert-butyl group; an alkoxy group such as a methoxy group, an ethoxy group, an isopropoxy group, or a tert-butoxy group; an aryl group such as a phenyl group or a 4-biphenylyl group; a halogen group such as a fluoro group; or a trifluoromethyl group.

In the case where the aromatic hydrocarbon group A is an unsubtituted 1,2-phenylene group, an unsubstituted phenyl group, a phenyl group substituted by a fluoro group, or a phenyl group substituted by a trifluoromethyl group is preferably used as the aryl group $A_r^1$, because red-color light emission with a chromaticity near the red chromaticity defined by NTSC (National Television Standards Comittee) (i.e., (x, y)=(0.67, 0.33)) can be obtained.

As specific examples of the substituent $R^1$, an alkyl groups such as a methyl group, an ethyl group, an isopropyl group, or a tert-butyl group; or an alkoxy group such as a methoxy group, an ethoxy group, an isopropoxy group, or a tert-butoxy group are given. Note that when hydrogen or a methyl group is used as R', steric hindrance of the ligand portion P is reduced and the organometallic complex is easily ortho-metalated with a metal ion, which is preferable in terms of a synthesis yield.

As the structure of the ligand portion P in the above general formulae (G0) and (G10), more specifically, any structure of ligand groups 1 to 9 below can be applied. However, the present invention is not limited to these ligand groups. In the drawings, α denotes a position of carbon which is bound to the central metal M. β denotes a position of nitrogen which is coordinated to the central metal M.

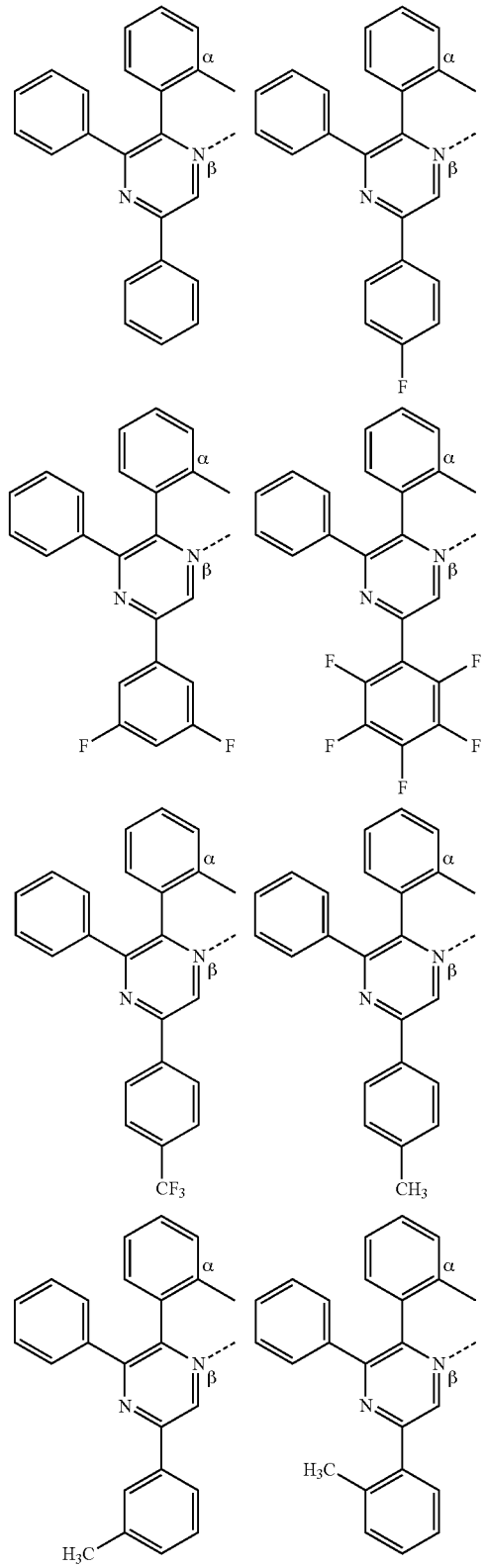

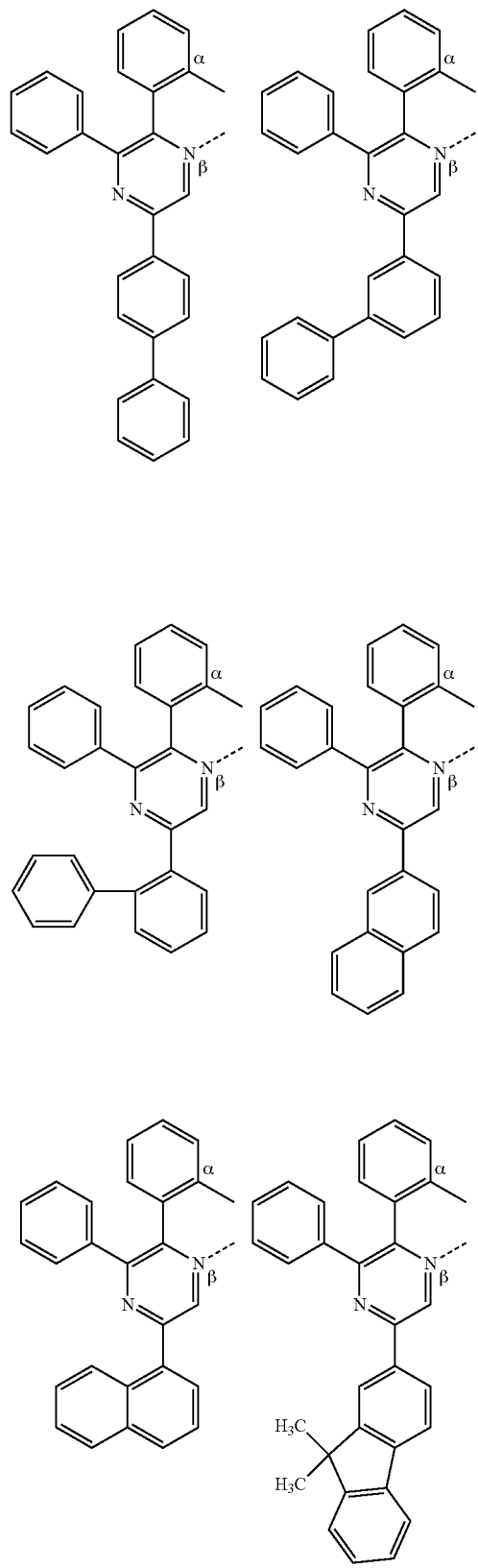
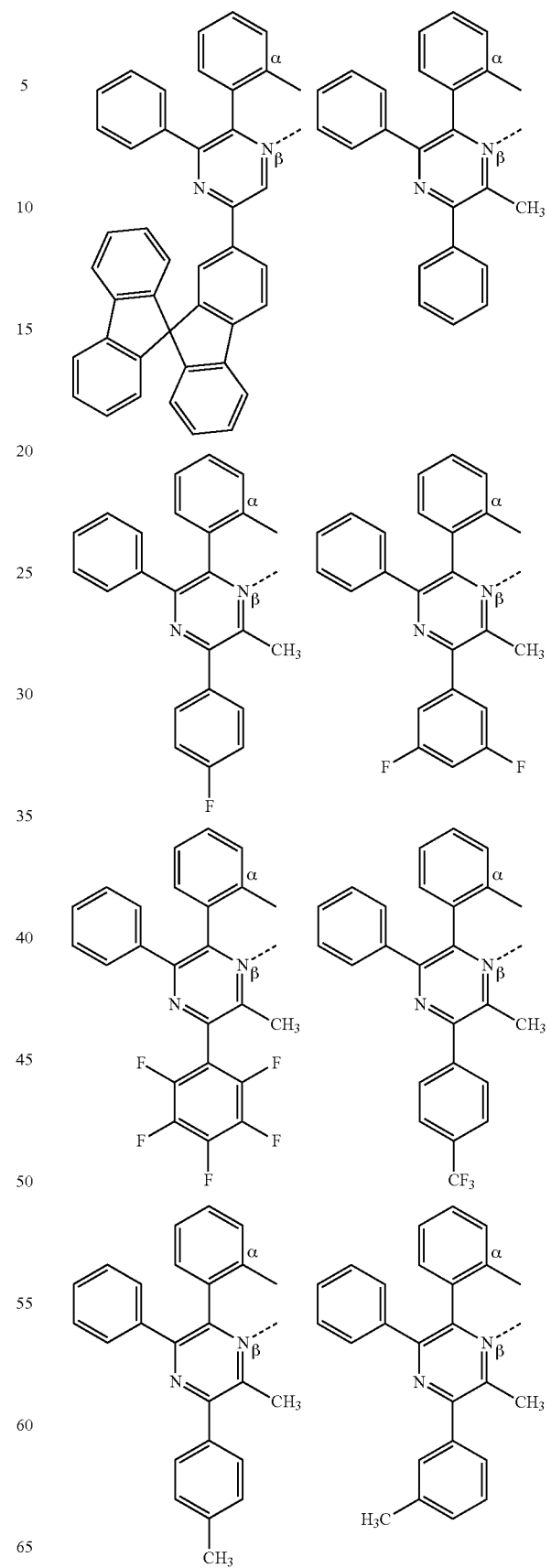

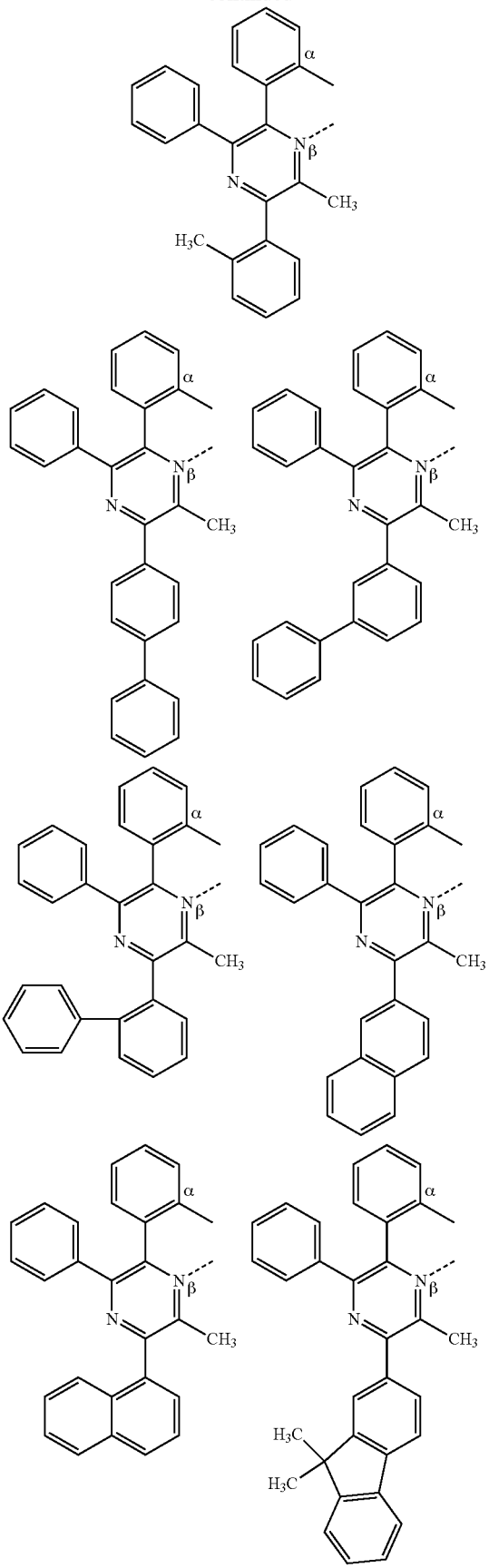
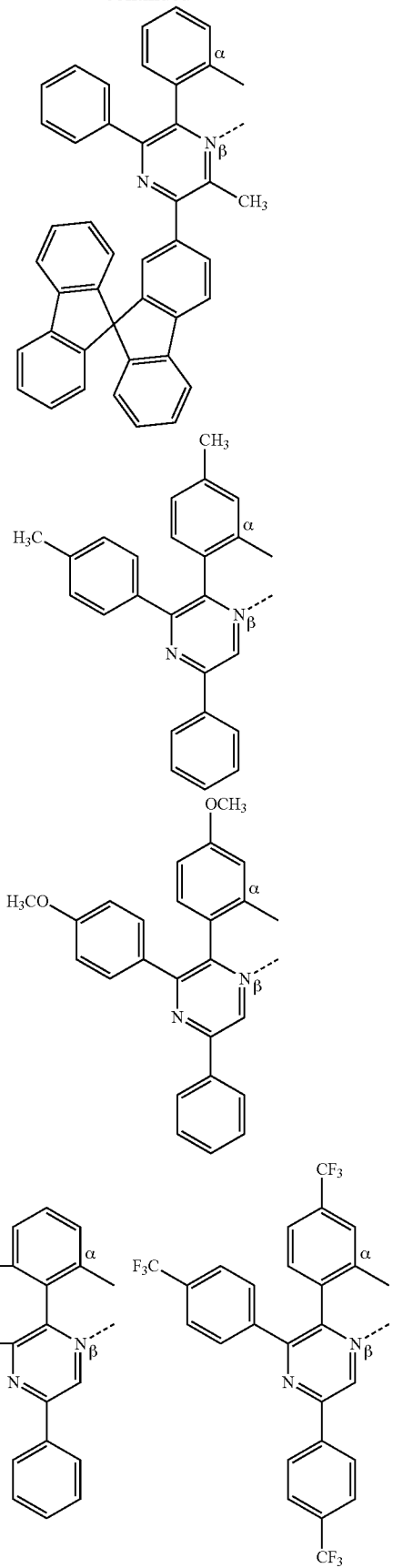

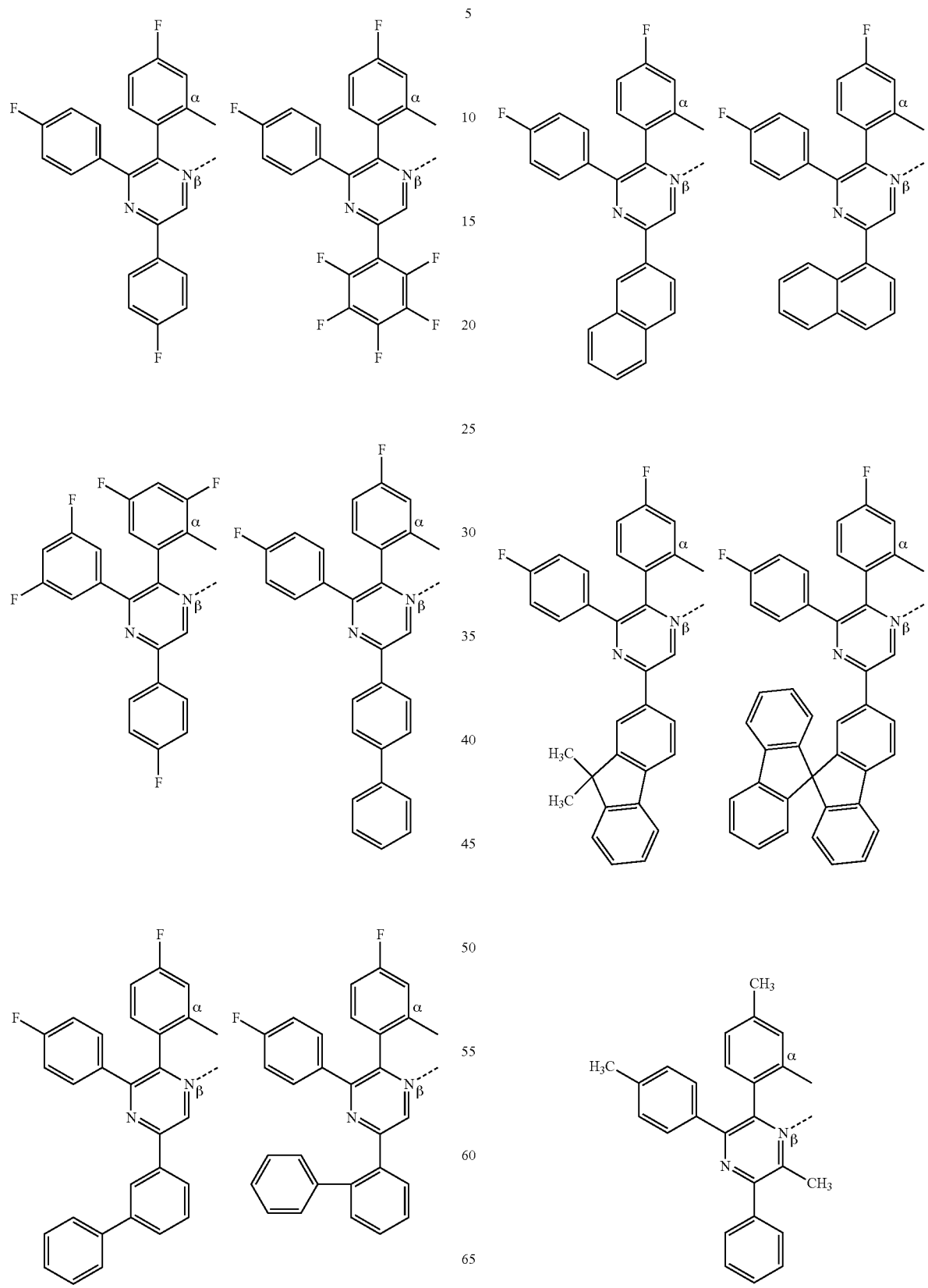

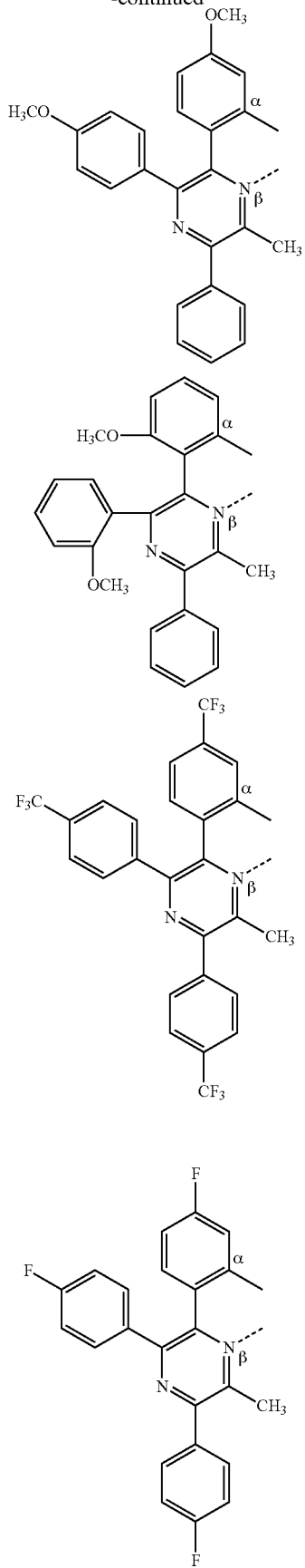
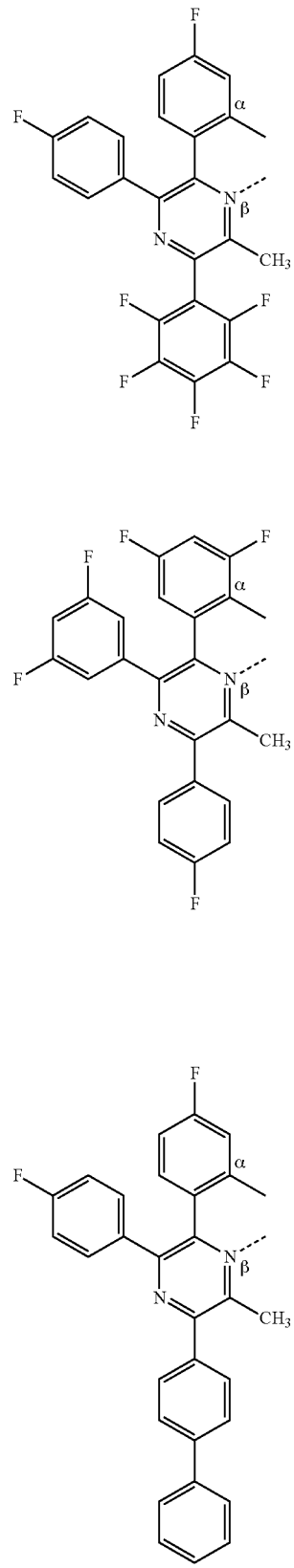

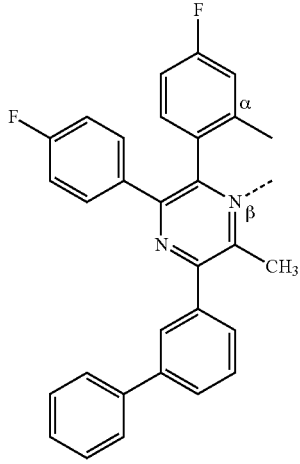
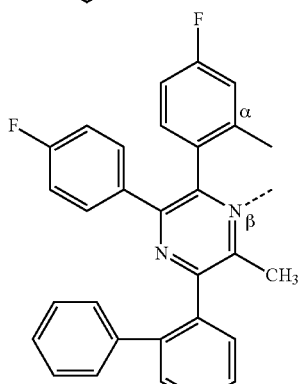
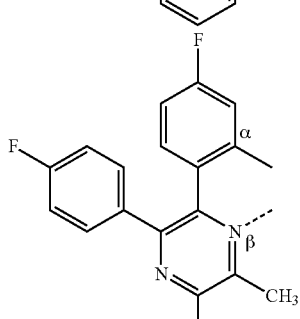
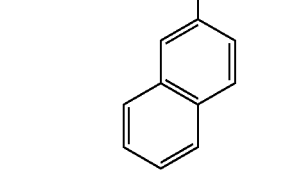
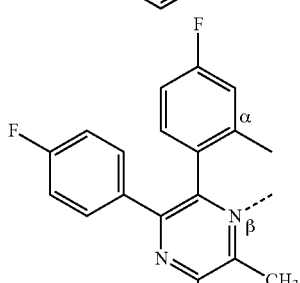
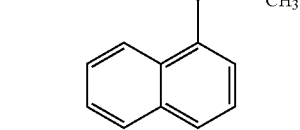
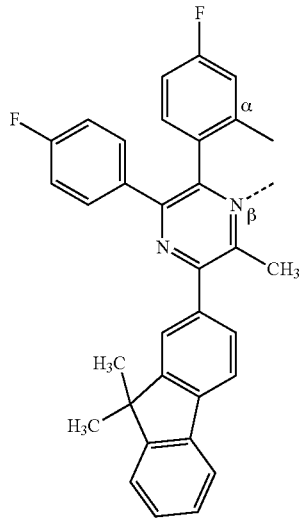
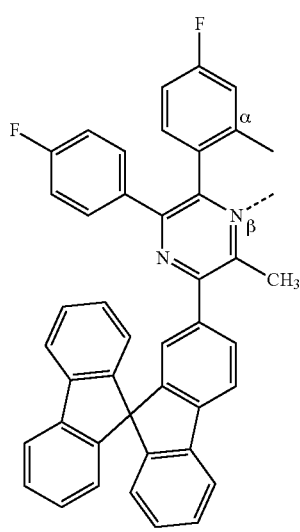
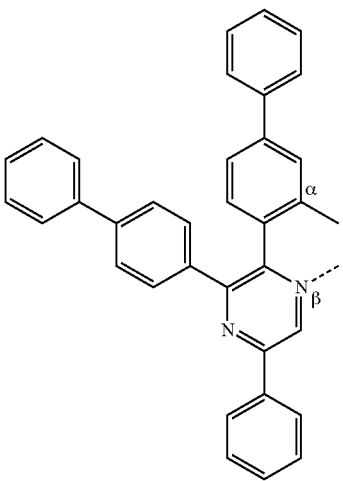

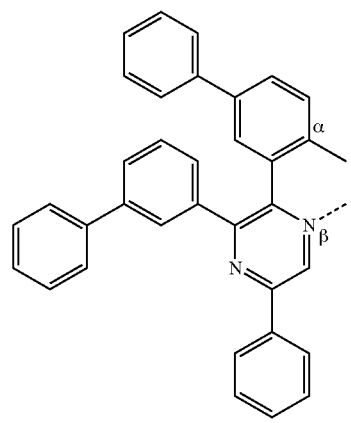
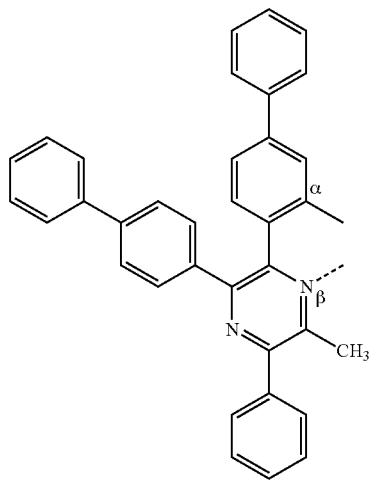
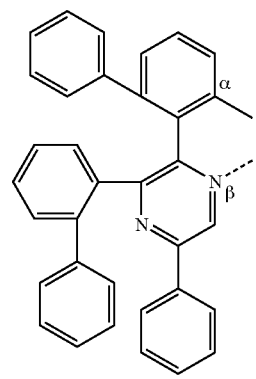
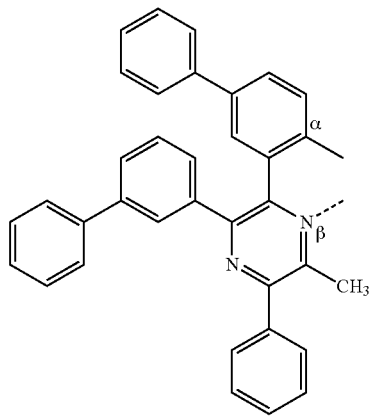
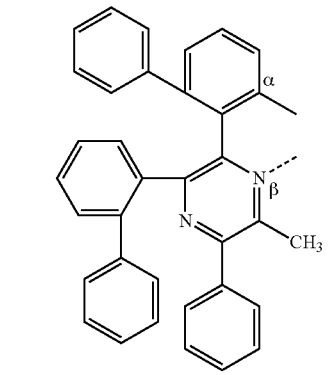
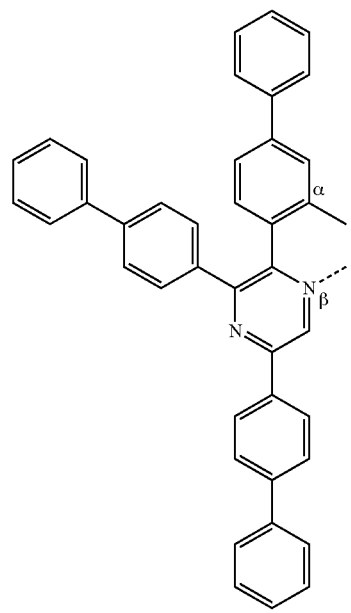
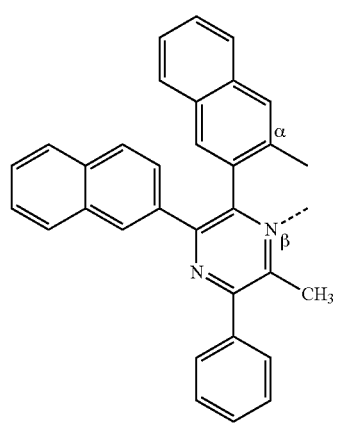

-continued
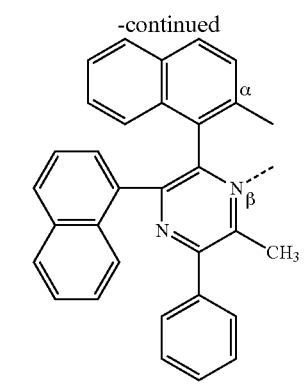
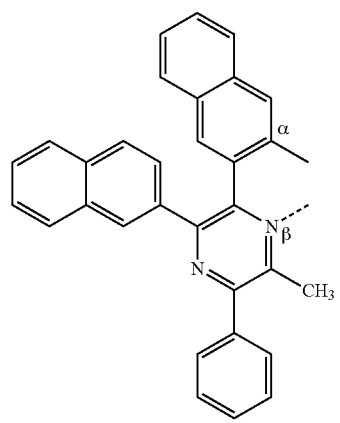
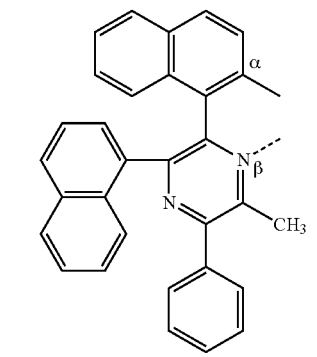
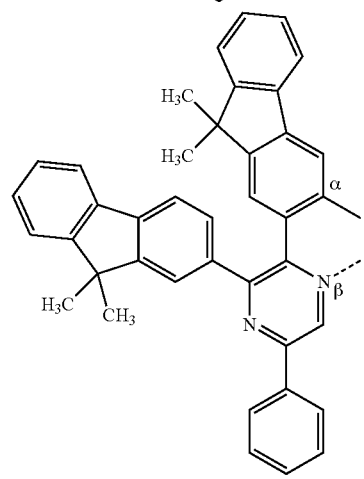
-continued
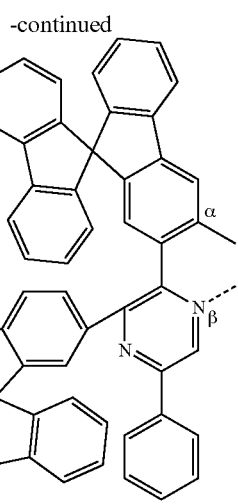
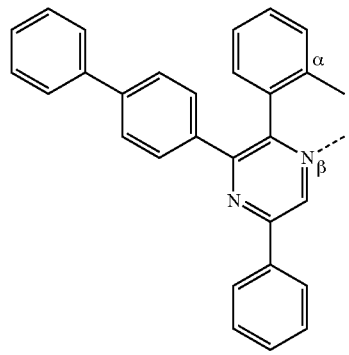
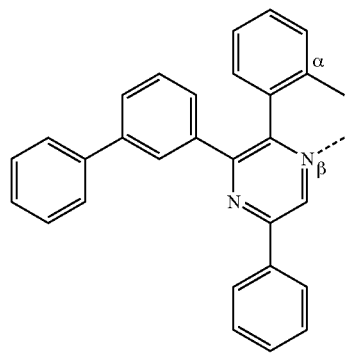
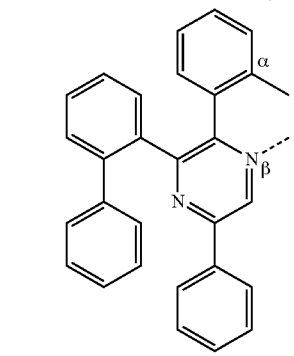

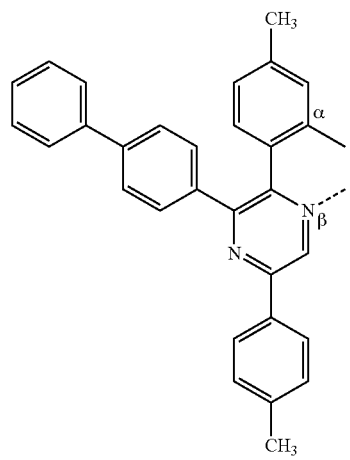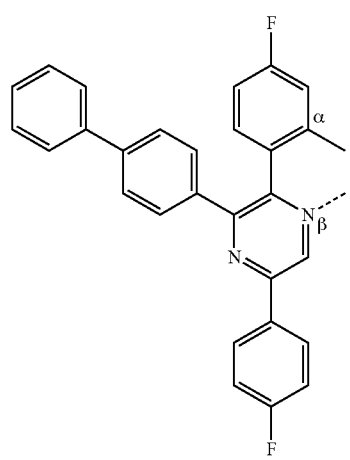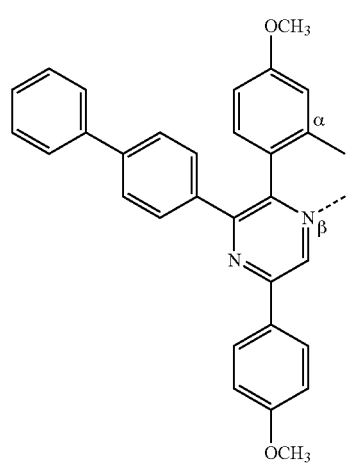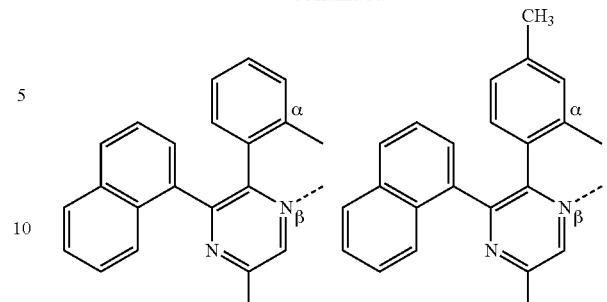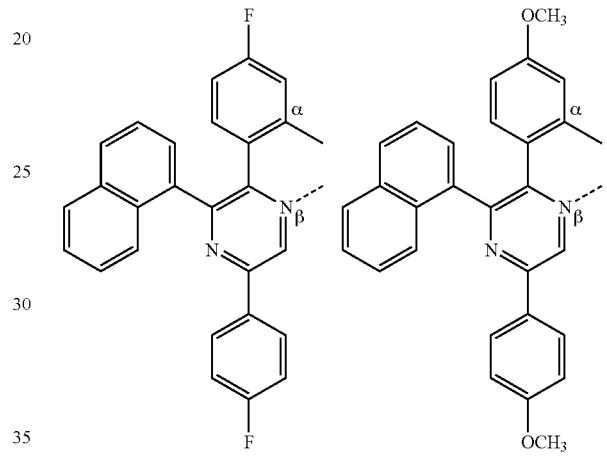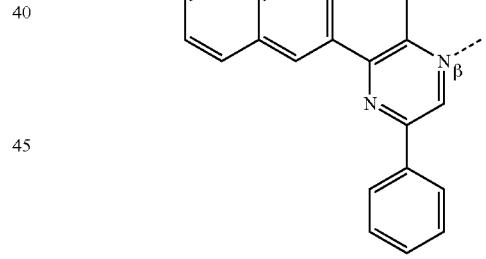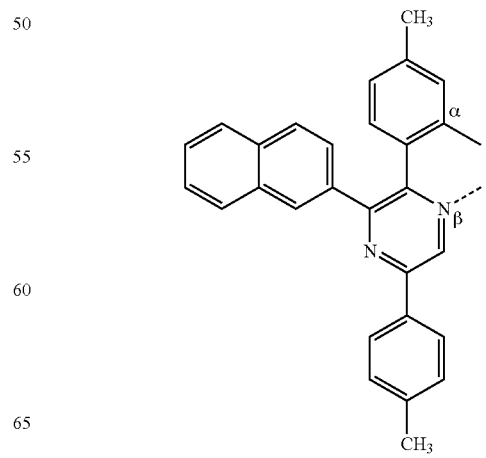

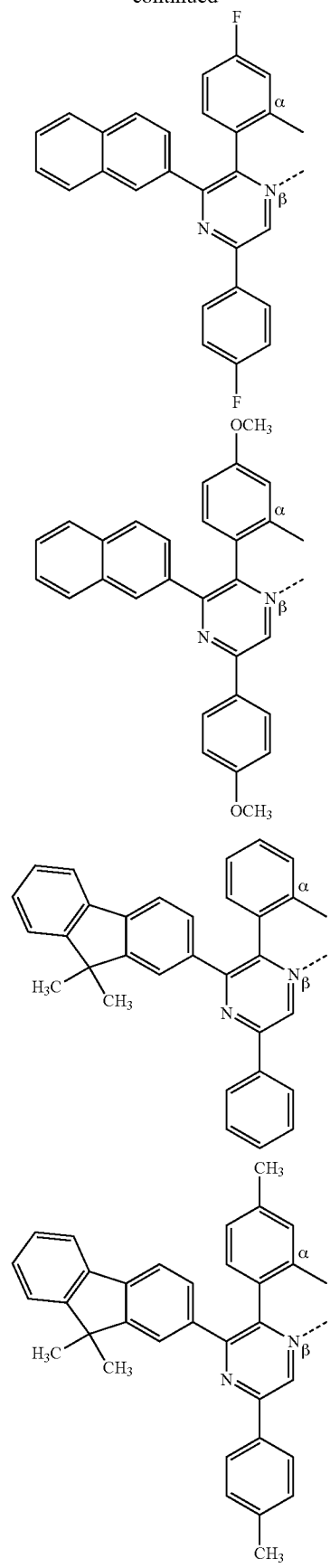
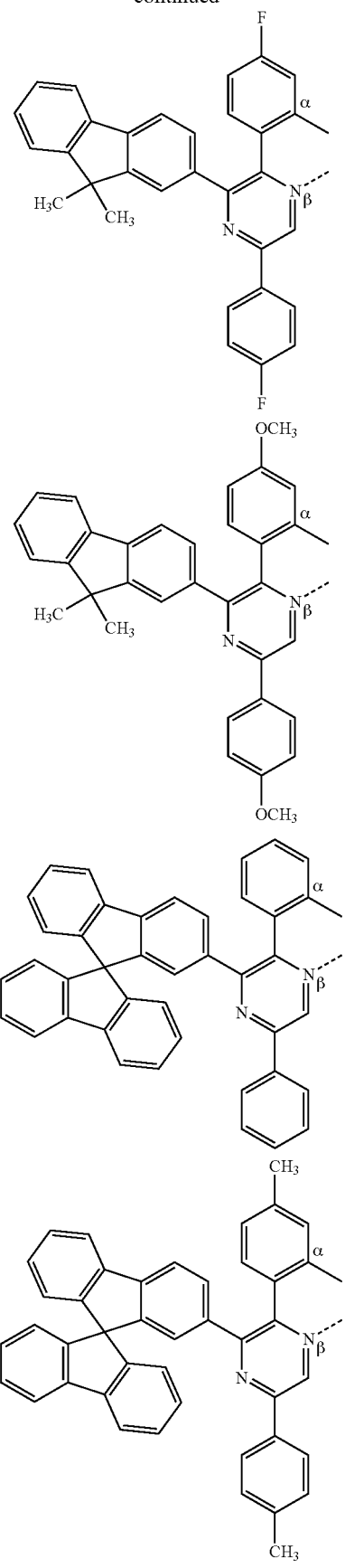

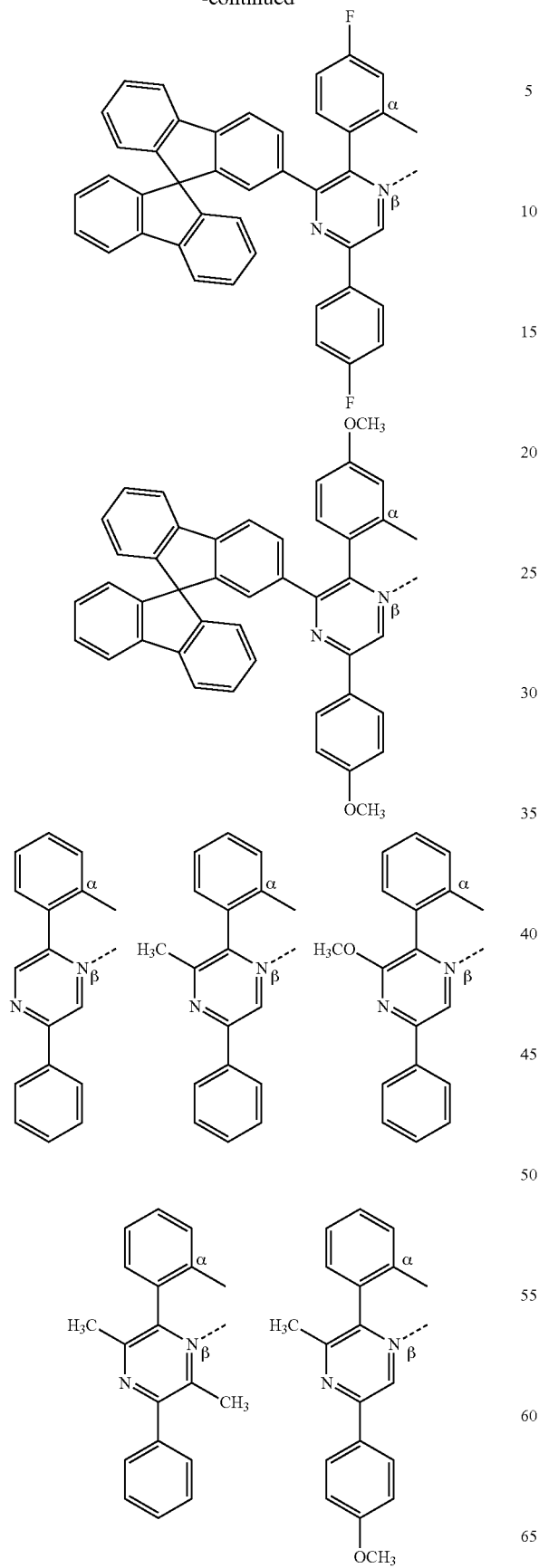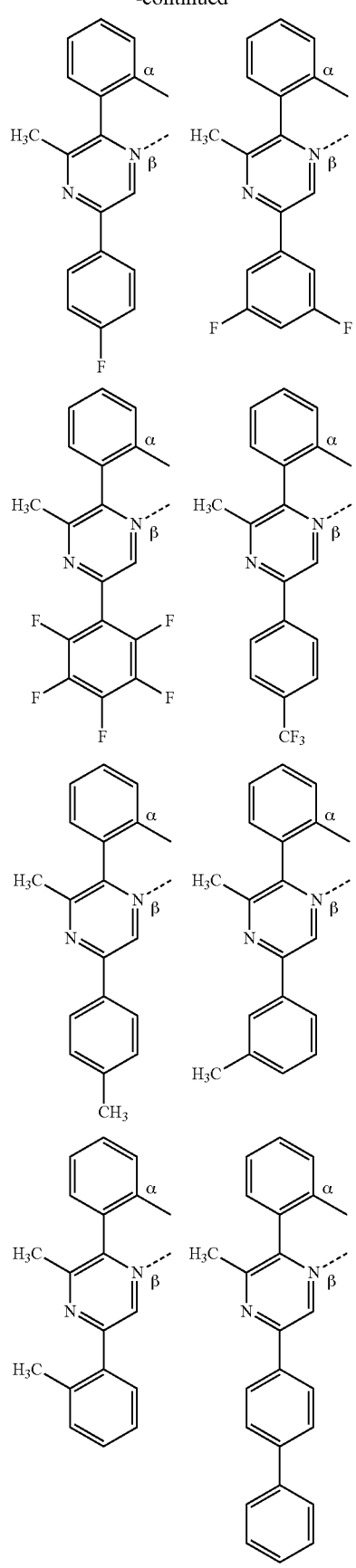

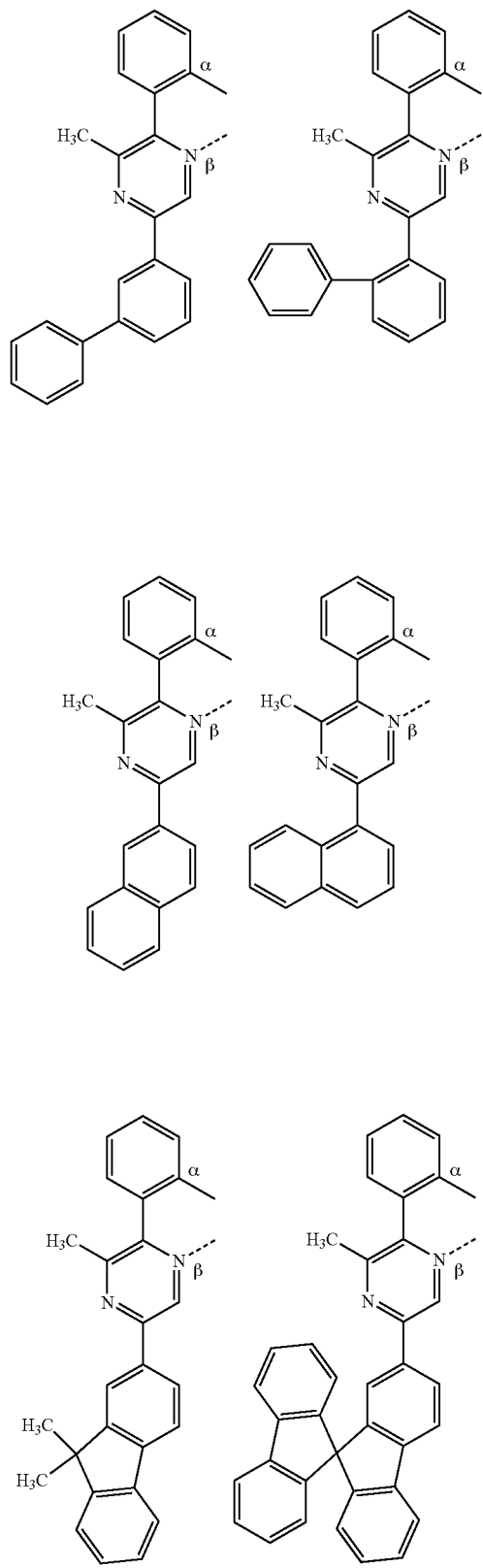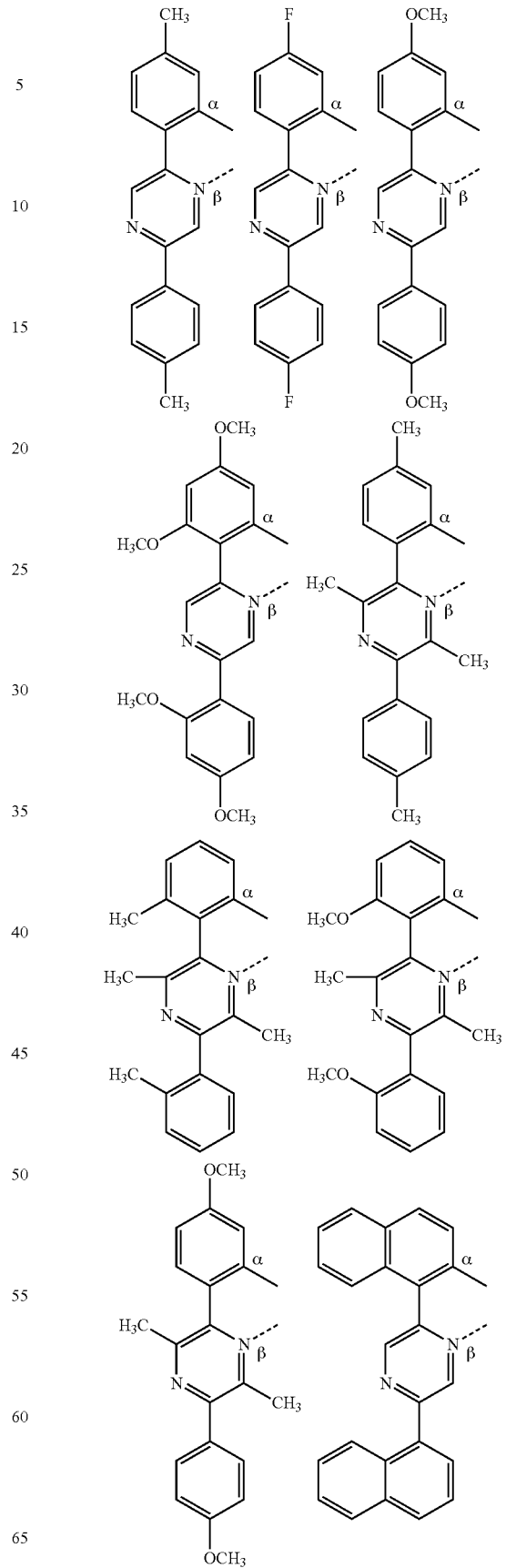

-continued

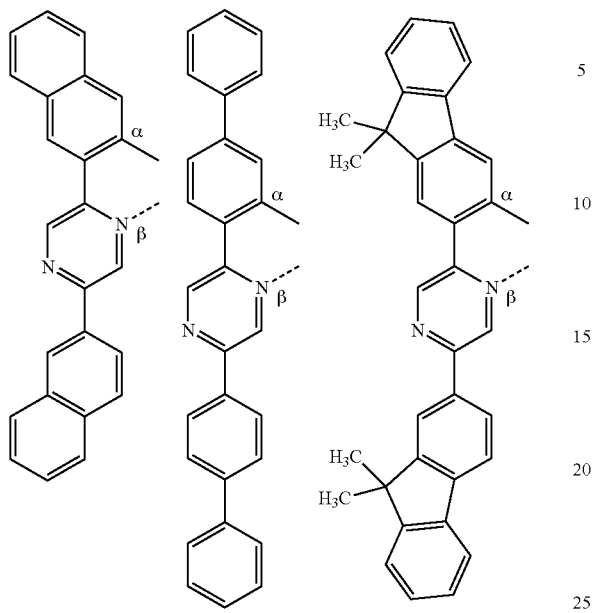

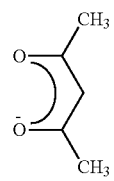
(L1)

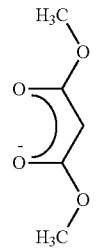
(L2)

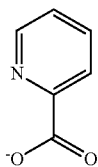
(L3)

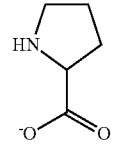
(L4)

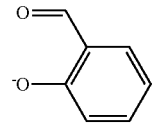
(L5)

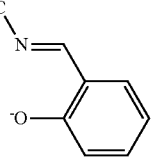
(L6)

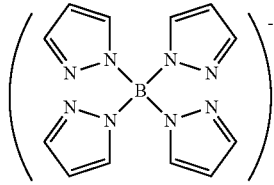
(L7)

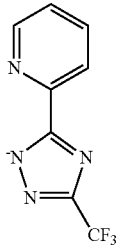
(L8)

Next, the monoanionic ligand L in the above general formula (G10) is described. The monoanionic ligand L is preferably either a monoanionic bidentate chelate ligand having a (β-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen. This is because these ligands have high coordinating ability. More specifically, monoanionic ligands represented by the following structural formulae (L1) to (L8) are given; however, the present invention is not limited to these.

By using the central metal M, the ligand groups 1 to 9, the monoanionic ligand L as described above in combination as appropriate, an organometallic complex of the present invention is constituted. Specific structural formulae (1) to (44) of organometallic complexes of the present invention are given below. However, the present invention is not limited to these.
(1)
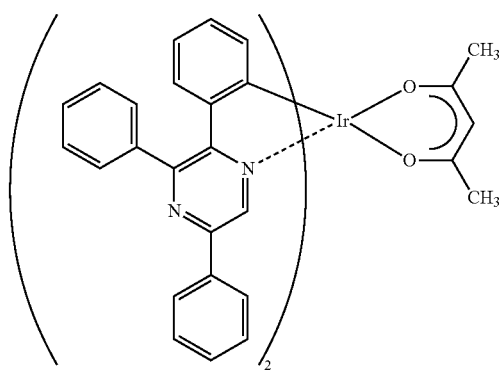
(2)
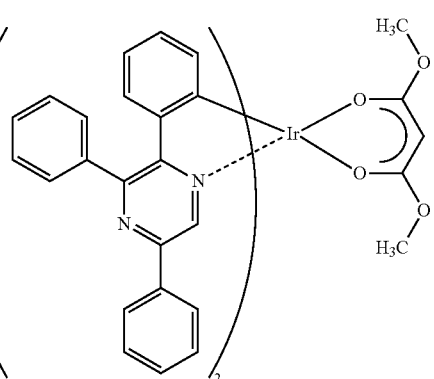
(3)
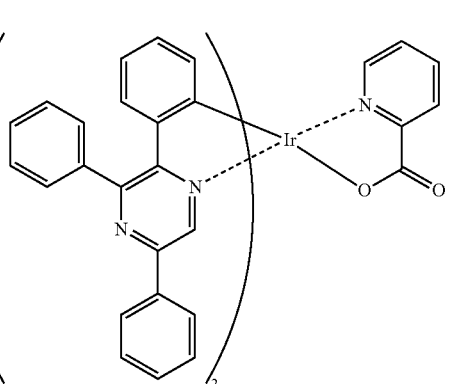
(4)
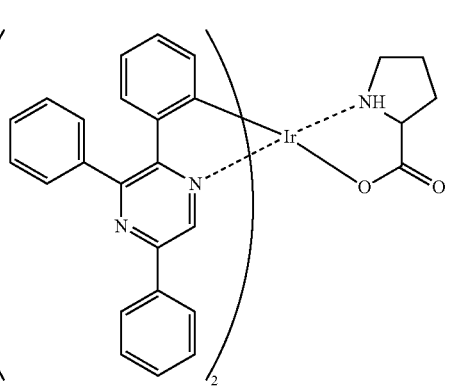
-continued
(5)
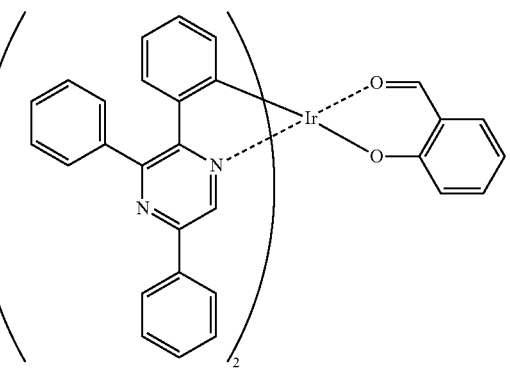
(6)
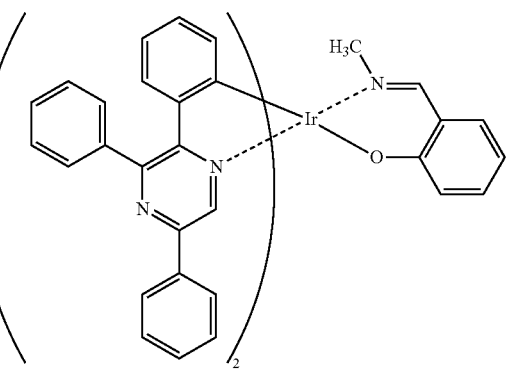
(7)
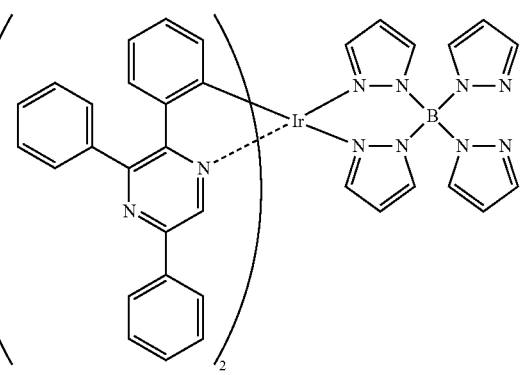
(8)
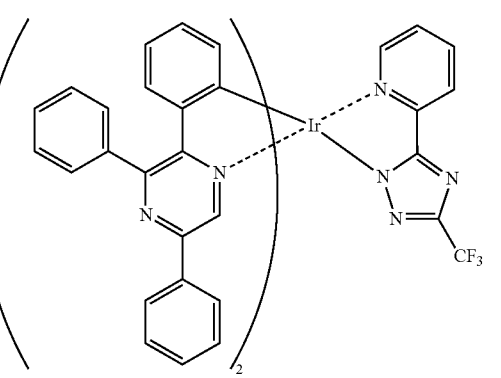

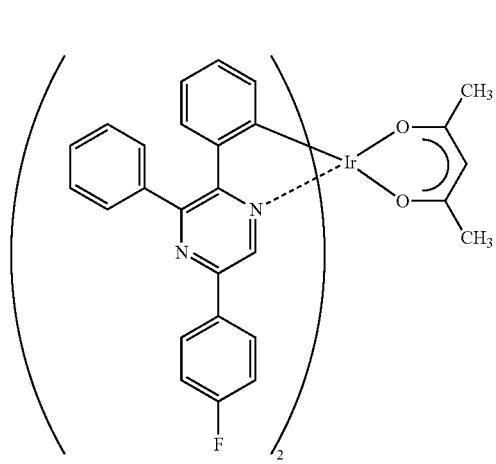
(9)
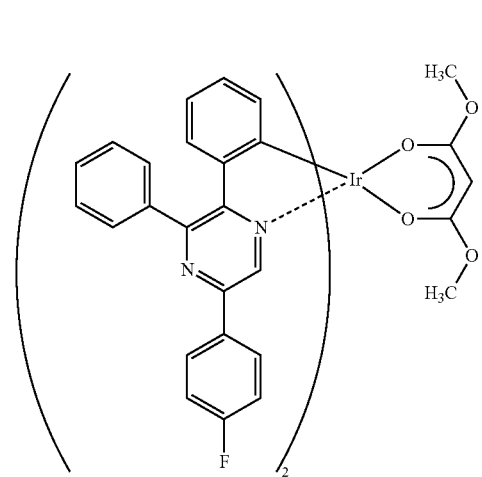
(10)
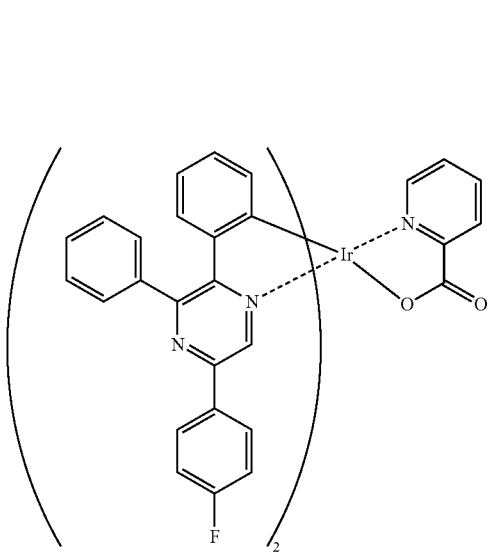
(11)
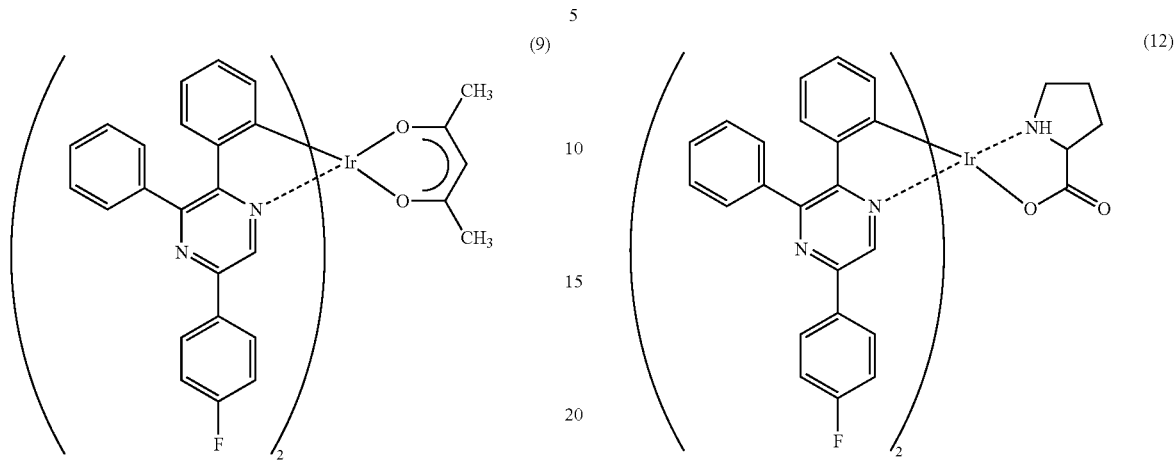
(12)
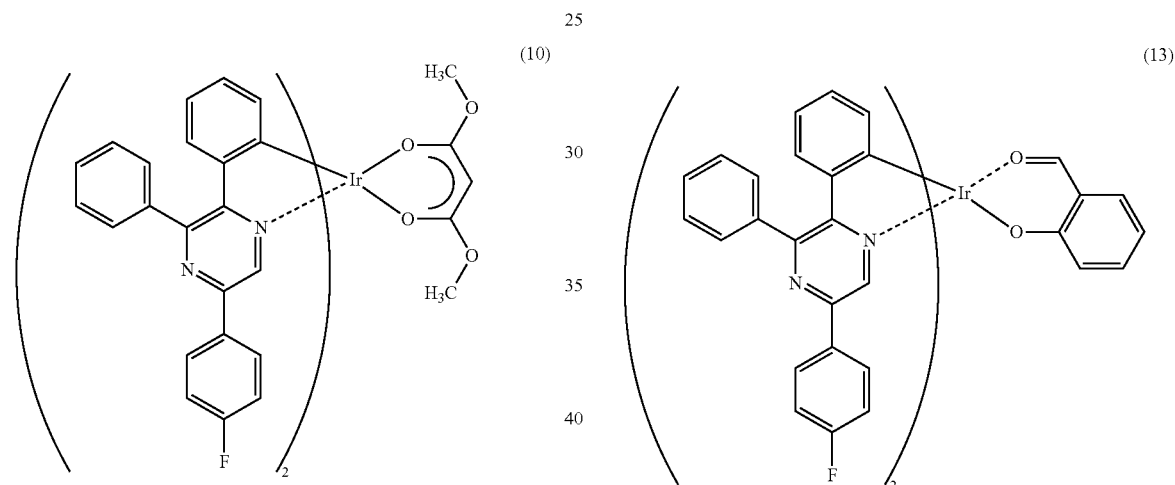
(13)
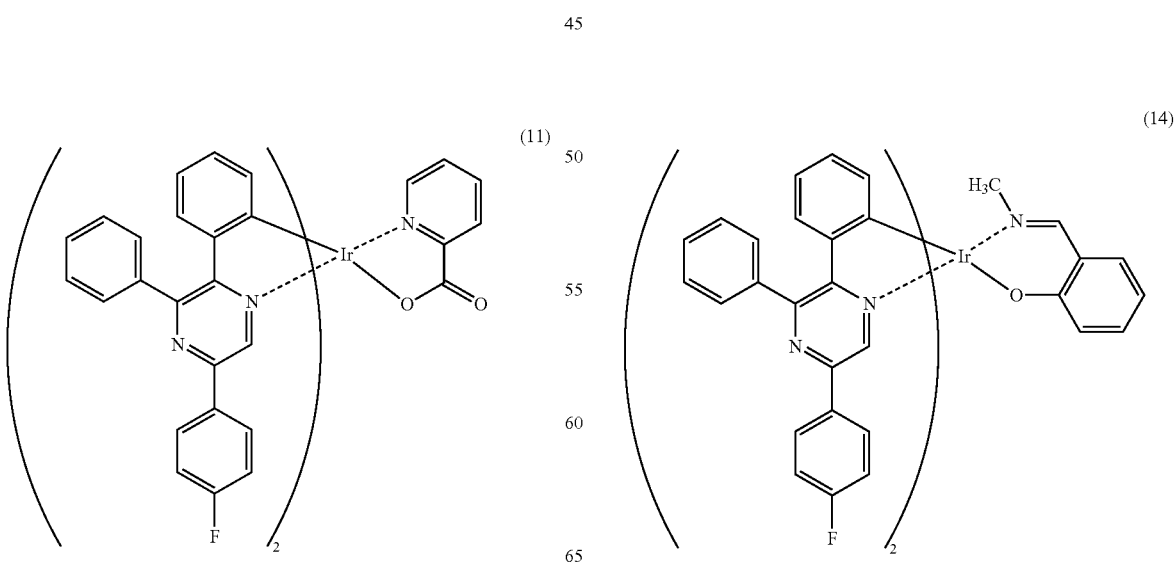
(14)

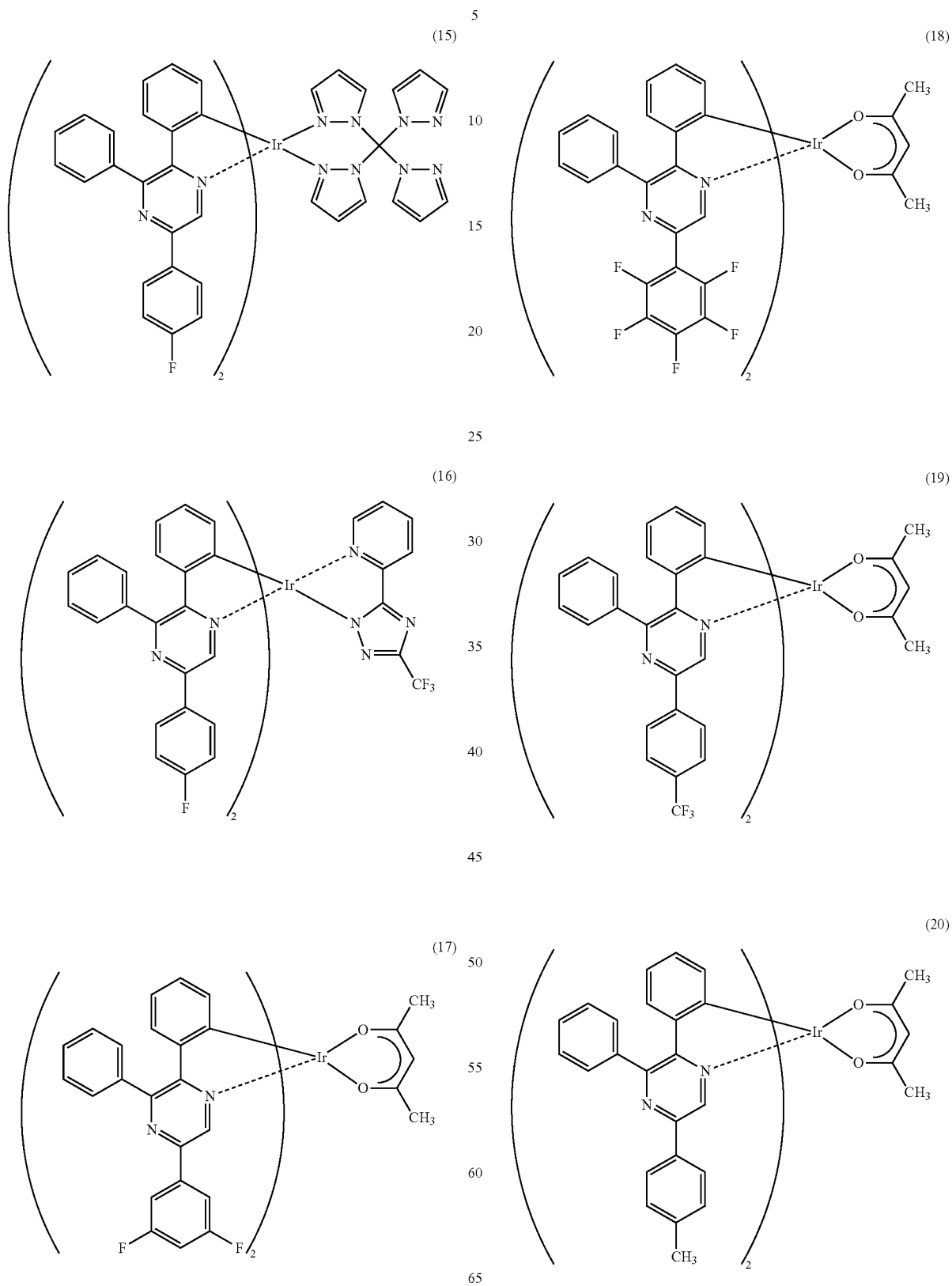

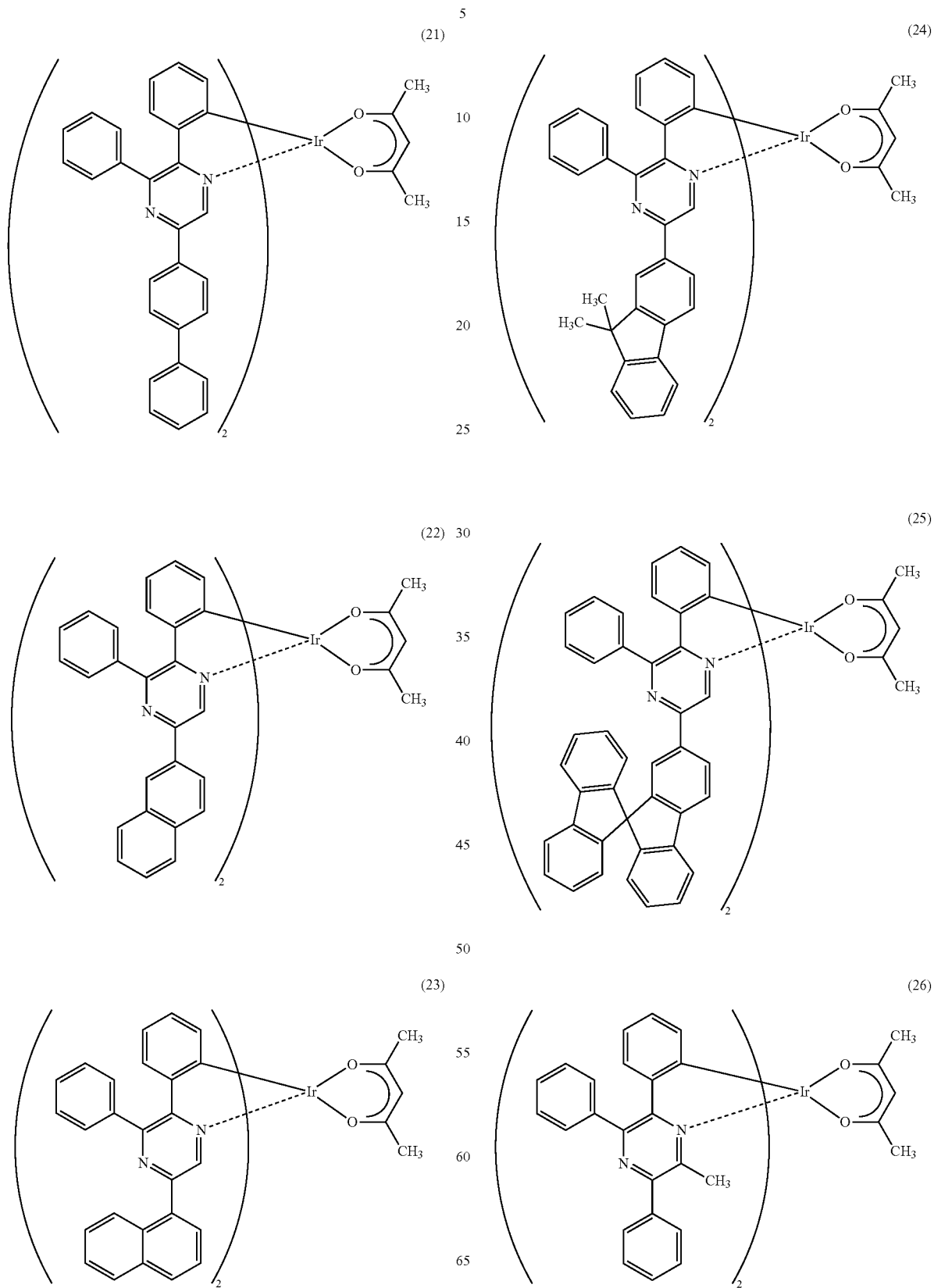

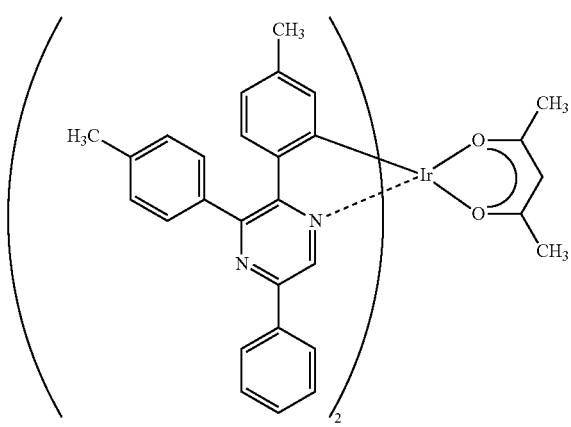
(27)
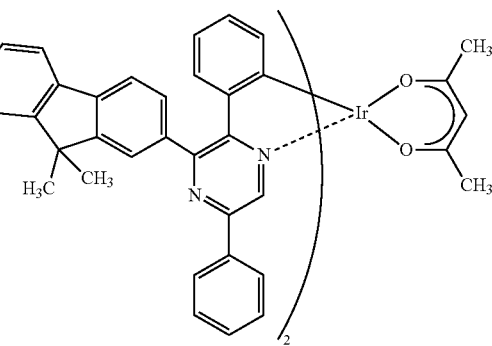
(31)
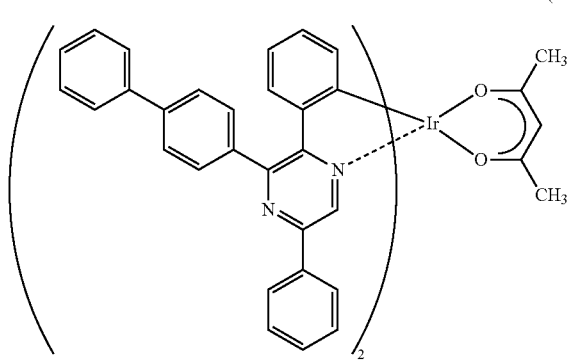
(28)
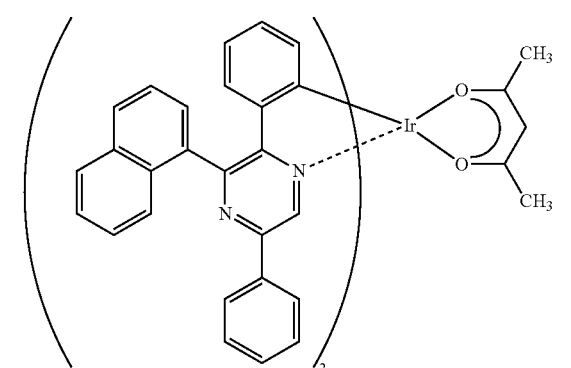
(29)
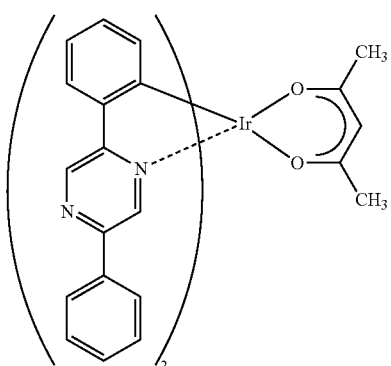
(32)
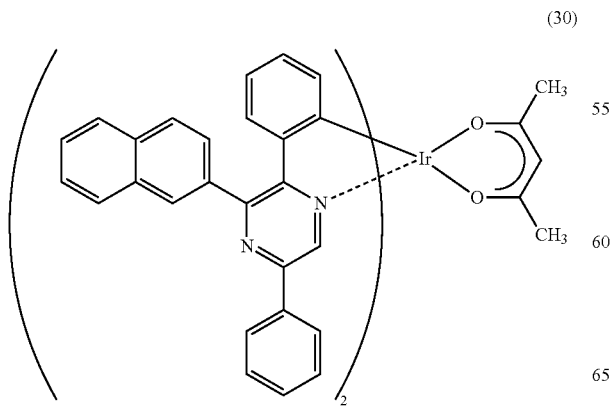
(30)
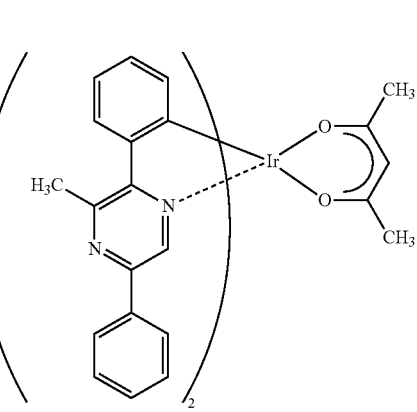
(33)
(34)

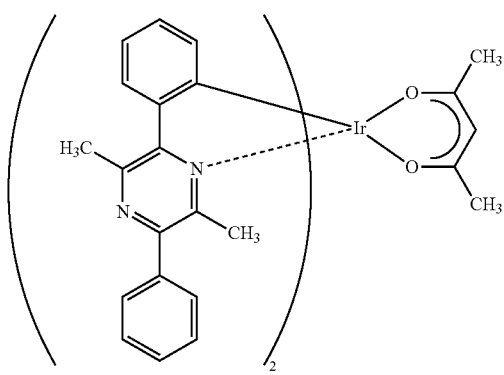
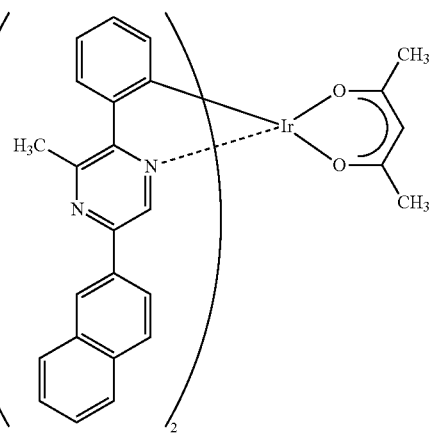
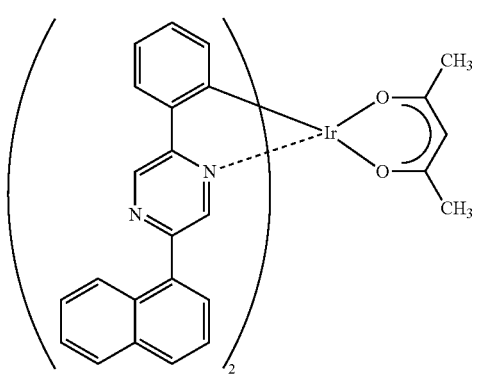
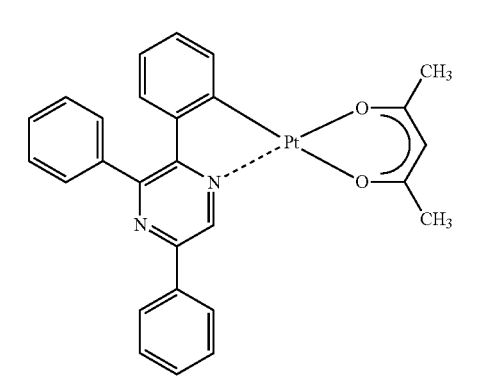
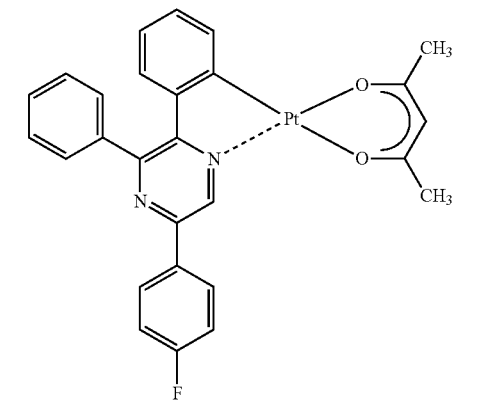

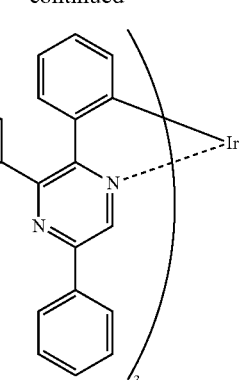

(43)

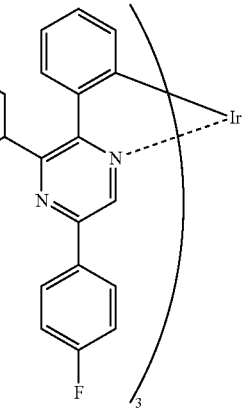

(44)

In the organometallic complexes represented by the above structural formulae (1) to (44), there can be a geometrical isomer and a stereoisomer depending on the type of ligands. The organometallic complexes of the present invention include such isomers.

In addition, there are two geometrical isomers of a facial isomer and a meridional isomer in each of the organometallic complexes represented by the structural formulae (43) and (44). The organometallic complexes of the present invention include both isomers, too.

The foregoing organometallic complexes of the present invention can be used as photosensitizers owing to capability of intersystem crossing. Further, it can emit phosphorescence. Thus, the organometallic complexes of the present invention can be used as a light emitting material or a light emitting substance for a light emitting element.

Embodiment Mode 2

Embodiment Mode 2 will describe a mode of a light emitting element which has the organometallic complex of the present invention described in Embodiment Mode 1, as a light emitting substance with reference to FIG. 1.

FIG. 1 shows a light emitting element having a light emitting layer 113 between a first electrode 101 and a second electrode 102. The light emitting layer 113 includes the organometallic complex of the present invention as described in Embodiment Mode 1.

By applying voltage to such a light emitting element, holes injected from the first electrode 101 side and electrons injected from the second electrode 102 side recombine with each other in the light emitting layer 113 to bring the organometallic complex of the present invention to an excited state. When the organometallic complex in the excited state returns to the ground state, it emits light. As thus described, the organometallic complex of the present invention functions as a light emitting substance of the light emitting element. In the light emitting element of Embodiment Mode 2, the first electrode 101 functions as an anode and the second electrode 102 functions as a cathode.

Here, the light emitting layer 113 includes an organometallic complex of the present invention. The light emitting layer 113 is preferably a layer including a substance which has a larger triplet excitation energy than that of the organometallic complex of the present invention as a host and also including the organometallic complex of the present invention which is dispersedly contained as a guest. Thus, quenching of light emitted from the organometallic complex of the present invention caused depending on the concentration can be prevented. It is to be noted that the triplet excitation energy indicates an energy gap between a ground state and a triplet excited state.

There are no particular limitations on the substance (i.e., a host) used for dispersing the organometallic complex of the present invention. In addition to a compound having an arylamine skeleton such as 2,3-bis(4-diphenylaminophenyl)quinoxaline (abbreviation: TPAQn) or 4,4'-bis[N-(1-naphthyl)-N-phenylamino]biphenyl (abbreviation: NPB), a carbazole derivative such as 4,4'-di(N-carbazolyl)biphenyl (abbreviation: CBP) or 4,4',4''-tris(N-carbazolyl)triphenylamine (abbreviation: TCTA), or a metal complex such as bis[2-(2-hydroxyphenyl)pyridinato]zinc (abbreviation: $Znpp_2$), bis[2-(2-hydroxyphenyl)benzoxazolato]zinc (abbreviation: ZnBOX), bis(2-methyl-8-quinolinolato)(4-phenylphenolato)aluminum (abbreviation: BAlq) or tris(8-quinolinolato)aluminum (abbreviation: $Alq_a$) is preferably used. Moreover, a high molecular compound such as poly(N-vinylcarbazole) (abbreviation: PVK) can also be used. In particular when using a metal complex such as bis[2-(2-hydroxyphenyl)pyridinato]zinc (abbreviation: $Znpp_2$), bis[2-(2-hydroxyphenyl)benzoxazolato]zinc (abbreviation: ZnBOX), or bis(2-methyl-8-quinolinolato)(4-phenylphenolato)aluminum (abbreviation: BAlq), the organometallic complex of the present invention can emit light efficiently. It is further preferable to use a zinc oxide.

Since the organometallic complex of the present invention can emit red light, a light emitting element which emits red light can be provided. Since the organometallic complex of the present invention has high light emission efficiency, a light emitting element with high light emission efficiency can be provided. Furthermore, a light emitting element which emits red light with high luminous efficiency (cd/A) can be provided.

Since the light emitting element of the present invention has high light emission efficiency, power consumption can be reduced.

Although there are no particular limitations on the first electrode 101, the first electrode 101 is preferably formed of a substance which has a high work function when the first electrode 101 functions as an anode as in Embodiment Mode 2. Specifically, in addition to indium tin oxide (ITO), indium tin oxide containing silicon oxide (ITSO), and indium oxide containing zinc oxide at 2 to 20 wt % (IZO), gold (Au), platinum (Pt), nickel (Ni), tungsten (W), chromium (Cr), molybdenum (Mo), iron (Fe), cobalt (Co), copper (Cu), palladium (Pd), or the like can be used. The first electrode 101 can be formed by, for example, a sputtering method, an evaporation method, or the like.

Further, although there are not particular limitations on the second electrode 102, the second electrode 102 is preferably formed of a substance which has a low work function when the second electrode 102 functions as a cathode as in Embodiment Mode 2. Specifically, in addition to aluminum (Al) or indium (In), an alkali metal such as lithium (Li) or cesium (Cs); an alkaline-earth metal such as magnesium (Mg) or calcium (Ca); a rare-earth metal such as erbium (Er) or ytterbium (Yb) can be used. In addition, an alloy such as aluminum-lithium alloy (AlLi) or magnesium-silver alloy (MgAg) can also be used. The second electrode 102 can be formed by, for example, a sputtering method, an evaporation method, or the like.

In order to extract emitted light to the outside, one or both of the first electrode 101 and the second electrode 102 is/are preferably an electrode formed of a conductive film of indium tin oxide (ITO) or the like which can transmit visible light or an electrode with a thickness of several to several tens of nm so as to transmit visible light.

In addition, a hole transporting layer 112 may be provided between the first electrode 101 and the light emitting layer 113 as shown in FIG. 1. Here, the hole transporting layer is a layer which has a function of transporting holes injected from the first electrode 101 to the light emitting layer 113. The hole transporting layer 112 is provided to keep the first electrode 101 away from the light emitting layer 113 in this way; thus, quenching of light due to a metal can be prevented. However, the hole transporting layer 112 is not necessarily provided.

There are no particular limitations on a substance forming the hole transporting layer 112, and typically, an aromatic amine compound such as 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4'-bis[N-(9,9-dimetylfluoren-2-yl)-N-phenylamino]biphenyl (abbreviation: DFLDPBi), 4,4',4''-tris (N,N-diphenylamino)triphenylamine (abbreviation: TDATA), or 4,4',4''-tris[N-(3-methylphenyl)-N-phenylamino]triphenylamine (abbreviation: m-MTDATA) can be used. Moreover, a high molecular compound such as poly(4-vinyl triphenylamine) (abbreviation: PVTPA) can also be used.

In addition, the hole transporting layer 112 may have a multilayer structure in which two or more layers are stacked, or may be formed of a mixture of two or more substances.

Further, an electron transporting layer 114 may be provided between the second electrode 102 and the light emitting layer 113 as shown in FIG. 1. Here, the electron transporting layer is a layer which has a function of transporting electrons injected from the second electrode 102 to the light emitting layer 113. The electron transporting layer 114 is provided to keep the second electrode 102 away from the light emitting layer 113 in this way; thus, quenching of light due to a metal can be prevented. Note that the electron transporting layer 114 is not necessarily provided.

There are no particular limitations on a substance forming the electron transporting layer 114. Typically, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolato)(4-phenylphenolato)aluminum (abbreviation: BAlq), bis[2-(2-hydroxyphenyl)benzoxazolato]zinc (abbreviation: ZnBOX), or bis[2-(2-hydroxyphenyl)benzothiazolato]zinc (abbreviation: Zn(BTZ)$_2$) may be used.

Further, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), or 4,4'-bis(5-methylbenzoxazol-2s-yl)stilbene (abbreviation: BzOs) can also be used. In addition, a high molecular compound such as poly(2,5-pyridine-diyl) (abbreviation: PPy) can also be used.

In addition, the electron transporting layer 114 may have a multilayer structure in which two or more layers are stacked, or may be formed of a mixture of two or more substances.

Further, a hole injecting layer 111 may be provided between the first electrode 101 and the hole transporting layer 112 as shown in FIG. 1. Here, the hole injecting layer is a layer that has a function of assisting injection of holes from an electrode functioning as an anode to the hole transporting layer 112. Note that the hole injecting layer 111 is not necessarily provided.

There are no particular limitations on a substance forming the hole injecting layer 111. For forming the hole injecting layer 111, a metal oxide such as vanadium oxide (VO$_x$), niobium oxide (NbO$_x$), tantalum oxide (TaO$_x$), chromium oxide (CrO$_x$), molybdenum oxide (MoO$_x$), tungsten oxide (WOO, manganese oxide (MnO$_x$), rhenium oxide (ReO$_x$), or ruthenium oxide (RuO$_x$) can be used. In addition, a phtalocyanine based compound such as phthalocyanine (abbreviation: H$_2$Pc) or copper phthalocyanine (abbreviation: CuPc) can also be used. In addition, the substances for forming the hole transporting layer 112 as described above can also be used. Further, a high molecular compound such as a mixture of poly(ethylenedioxythiophene) and poly (styrene sulfonate) (abbreviation: (PEDOT/PSS)) can also be used.

A composite material which is formed by combining an organic compound and an electron acceptor may be used for the hole injecting layer 111. The composite material is superior in a hole injecting property and a hole transporting property, since holes are generated in the organic compound by the electron acceptor. In this case, the organic compound is preferably a material excellent in transporting the generated holes. Specifically, the foregoing substances for forming the hole transporting layer 112 (such as aromatic amine compound) can be used for example. In addition, as the electron acceptor, a substance showing an electron accepting property to an organic compound may be used, and specifically, a transition metal oxide is preferable. For example, vanadium oxide (VO$_x$), niobium oxide (NbO$_x$), tantalum oxide (TaO$_x$), chromium oxide (CrO$_x$), molybdenum oxide (MoO$_x$), tungsten oxide (WO$_x$), manganese oxide (MnO$_x$), rhenium oxide (ReO$_x$), ruthenium oxide (RuO$_x$) and the like are given. Lewis acid such as iron chloride(III) or aluminum chloride(III) can also be used. In addition, an organic compound such as 7,7,8,8-tetracyano-2,3,5,6-tetrafluoroquinodimethane (abbreviation: F4-TCNQ) can also be used.

The hole injecting layer 111 may have a multilayer structure in which two or more layers are stacked, or may be formed of a mixture of two or more substances.

Further, an electron injecting layer 115 may be provided between the second electrode 102 and the electron transporting layer 114 as shown in FIG. 1. Here, the electron injecting layer is a layer which has a function of assisting injection of electrons from the electrode functioning as a cathode to the electron transporting layer 114. It is to be noted that the electron injecting layer 115 is not necessarily provided.

There are no particular limitations on a substance forming the electron injecting layer 115. A compound of an alkali metal or an alkaline-earth metal such as lithium fluoride (LiF), cesium fluoride (CsF), calcium fluoride (CaF$_2$), lithium oxide (LiO$_x$) can be used. In addition, a rare-earth metal compound such as erbium fluoride (ErF$_3$) can also be used. The above-mentioned substances for forming the electron transporting layer 114 can also be used.

A composite material which is formed by combining an organic compound and an electron donor may be used for the electron injecting layer 115. The composite material is superior in an electron injecting property and an electron transporting property, since electrons are generated in the organic compound by the electron donor. In this case, the organic compound is preferably a material excellent in transporting the generated electrons. Specifically, the foregoing materials for forming the electron transporting layer 114 (such as a metal complex, a heteroaromatic compound or the like) can be used for example. As the electron donor, a substance showing an electron donating property to the organic compound may be used, and specifically an alkali metal, an alkaline-earth metal or a rare-earth metal, for example, lithium, cesium, magnesium, calcium, erbium, or ytterbium, is preferable. Further, an alkali metal oxide, or an alkaline-earth metal oxide is preferable, and for example, lithium oxide (LiO$_x$), calcium oxide (CaO$_x$), barium oxide (BaO$_x$) or the like can be given. Lewis acid such as magnesium oxide can also be used. In addition, an organic compound such as tetrathiafulvalene (abbreviation: TFT) can also be used.

In the foregoing light emitting element of the present invention, each of the hole injecting layer 111, the hole transporting layer 112, the light emitting layer 113, the electron transporting layer 114, and the electron injecting layer 115 may be formed by any method, for example, an evaporation method, an inkjet method, an application method, or the like. In addition, the first electrode 101 or the second electrode 102 may also be formed by any method, for example, a sputtering method, an evaporation method, an inkjet method, an application method, or the like.

Embodiment Mode 3

The light emitting element of the present invention may have a plurality of light emitting layers. A plurality of light emitting layers are provided and lights emitted from each of the light emitting layers are mixed, thereby obtaining light which is the combination of the plurality of light. Accordingly, white-color light can be obtained for example. In Embodiment Mode 3, a light emitting element having a plurality of light emitting layers is described with reference to FIG. 2.

Figure 2:
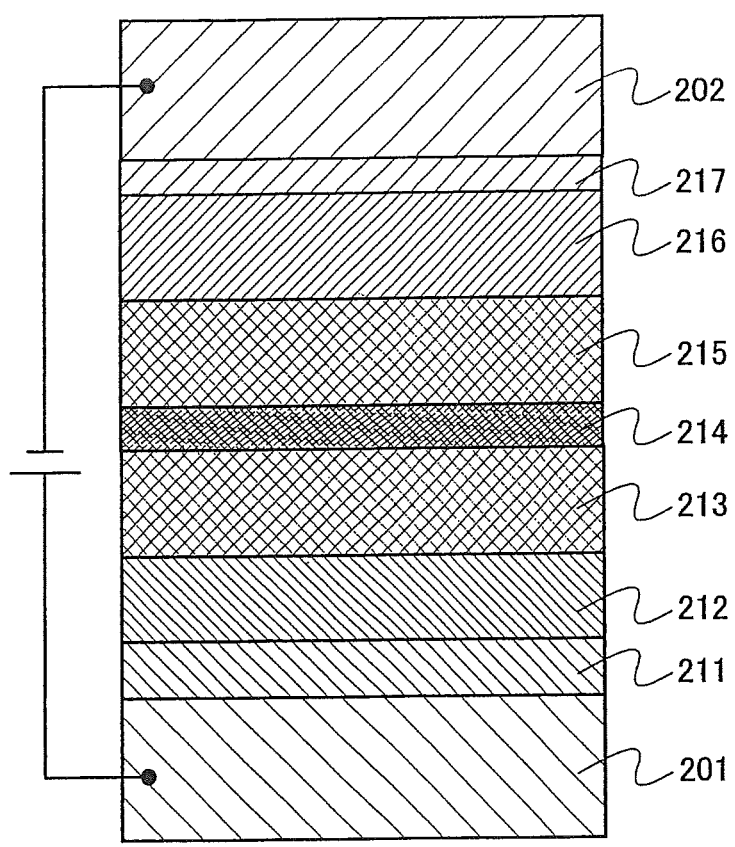
FIG. 2 shows a light emitting element of the present invention.

In FIG. 2, a first light emitting layer 213 and a second light emitting layer 215 are provided between a first electrode 201 and a second electrode 202. Light in which light emitted from the first light emitting layer 213 and light emitted from the second light emitting layer 215 are mixed can be obtained. A separation layer 214 is preferably formed between the first light emitting layer 213 and the second light emitting layer 215.

When voltage is applied so that the potential of the first electrode 201 is higher than the potential of the second electrode 202, current flows between the first electrode 201 and the second electrode 202, and holes and electrons are recombined in the first light emitting layer 213, the second light emitting layer 215, or the separation layer 214. Generated excitation energy is distributed to the first light emitting layer 213 and the second light emitting layer 215 to bring each of a first light emitting substance contained in the first light emitting layer 213 and a second light emitting substance contained in the second light emitting layer 215 to an excited state. Then, the first and second light emitting substances in the excited state emit light when returning to the ground state.

The first light emitting layer 213 contains the first light emitting substance typified by a fluorescent compound such as perylene, 2,5,8,11-tetra(tert-butyl)perylene (abbreviation: TBP), 4,4'-bis(2,2-diphenylvinyl)biphenyl (abbreviation: DPVBi), 4,4'-bis[2-(N-ethylcarbazol-3-yl)vinyl]biphenyl (abbreviation BCzVBi), bis(2-methyl-8-quinolinolato)(4-phenylphenolato)aluminum (abbreviation: BAlq), or bis(2-methyl-8-quinolinolato)galliumchloride (abbreviation: Gamq$_2$Cl); or a phosphorescent compound such as bis{2-[3,5-bis(trifluoromethyl)phenyl]pyridinato-N,C$^{2'}$} iridium (III)picolinate (abbreviation Ir(CF$_3$ppy)$_2$(pic)), bis[2-(4,6-difluorophenyl)pyridinato-N,C$^{2'}$]iridium(III) eacetylacetonate (abbreviation: FIr(acac)), bis[2-(4,6-difluorophenyl)pyridinato-N, C$^{2'}$]iridium(III)picolinate (abbreviation FIrpic), or bis[2-(4,6-difuluorophenyl) pyridinato-N,C$^{2'}$]iridium(III)tetra(1-pyrazolyl)borate (abbreviation: FIr6), from which light emission with a peak at 450 to 510 nm in an emission spectrum (i.e., blue light to blue green light) can be obtained. In addition, when the first light emitting substance is a fluorescent compound, the first light emitting layer 213 may preferably have a structure in which a substance having a larger singlet excitation energy than the first light emitting substance is used as a first host and the first light emitting substance is dispersedly contained as a guest. Further, when the first light emitting substance is a phosphorescent compound, the light emitting layer 213 preferably has a structure in which a substance having a larger triplet excitation energy than the first light emitting substance is used as a first host and the first light emitting substance is dispersedly contained as a guest. As the first host, 9,10-di(2-naphthyl)anthracene (abbreviation: DNA), 2-tert-butyl-9,10-di(2-naphthyl)anthracene (abbreviation: t-BuDNA) or the like can be used as well as NPB, CBP, TCTA, or the like. It is noted that the singlet excitation energy is an energy difference between a ground state. In addition, a singlet excited state. and the triplet excitation energy is an energy difference between a ground state and a triplet excited state.

On the other hand, the second light emitting layer 215 includes an organometallic complex of the present invention and can exhibit light emission of red color. Further, since the organometallic complex of the present invention has high light emission efficiency, a light emitting element with high luminous efficiency can be obtained. In addition, a light emitting element with reduced power consumption can be obtained.

The second light emitting layer 215 may have a similar structure to the light emitting layer 113 described in Embodiment Mode 2.

In addition, the separation layer 214 can be specifically formed of TPAQn, NPB, CBP, TCTA, Znpp$_2$, ZnBOX or the like described above. In this way, by providing the separation layer 214, a defect that emission intensity of one of the first light emitting layer 213 and the second light emitting layer 215 is stronger than the other can be prevented. Note that the separation layer 214 is not necessarily provided, and it may be provided as appropriate such that the ratio in emission intensity of the first light emitting layer 213 and the second light emitting layer 215 can be adjusted.

In Embodiment Mode 3, an organometallic complex of the present invention is used for the second light emitting layer 215, and another light emitting substance is used for the first light emitting layer 213; however, the organometallic complex of the present invention may be used for the first light emitting layer 213, and another light emitting substance may be used for the second light emitting layer 215.

In Embodiment Mode 3, a light emitting element including two light emitting layers is described as shown in FIG. 2; however, the number of the light emitting layers is not limited to two, and may be three, for example. Light emission from each light emitting layer may be mixed. As a result, white-color emission can be obtained, for example.

In addition, the first electrode 201 may have a similar structure to the first electrode 101 described in Embodiment Mode 2. In addition, the second electrode 202 may have a similar structure to the second electrode 102 described in Embodiment Mode 2.

In Embodiment Mode 3, as shown in FIG. 2, the hole injecting layer 211, the hole transporting layer 212, the electron transporting layer 216, and the electron injecting layer 217 are provided. As to structures of these layers, the structures of the respective layers described in Embodiment Mode 2 may be applied. However, these layers are not necessarily provided and may be provided depending on the element characteristics.

Embodiment Mode 4

Embodiment Mode 4 exemplifies a light emitting element which includes a plurality of light emitting layers, which has a different element structure from that in Embodiment Mode 3, and in which light is emitted from each light emitting layer.

Therefore, also in Embodiment Mode 4, light which is the combination of a plurality of light can be obtained. In other words, white-color light can be obtained, for example. Hereinafter, description is made with reference to FIG. 3.

Figure 3:
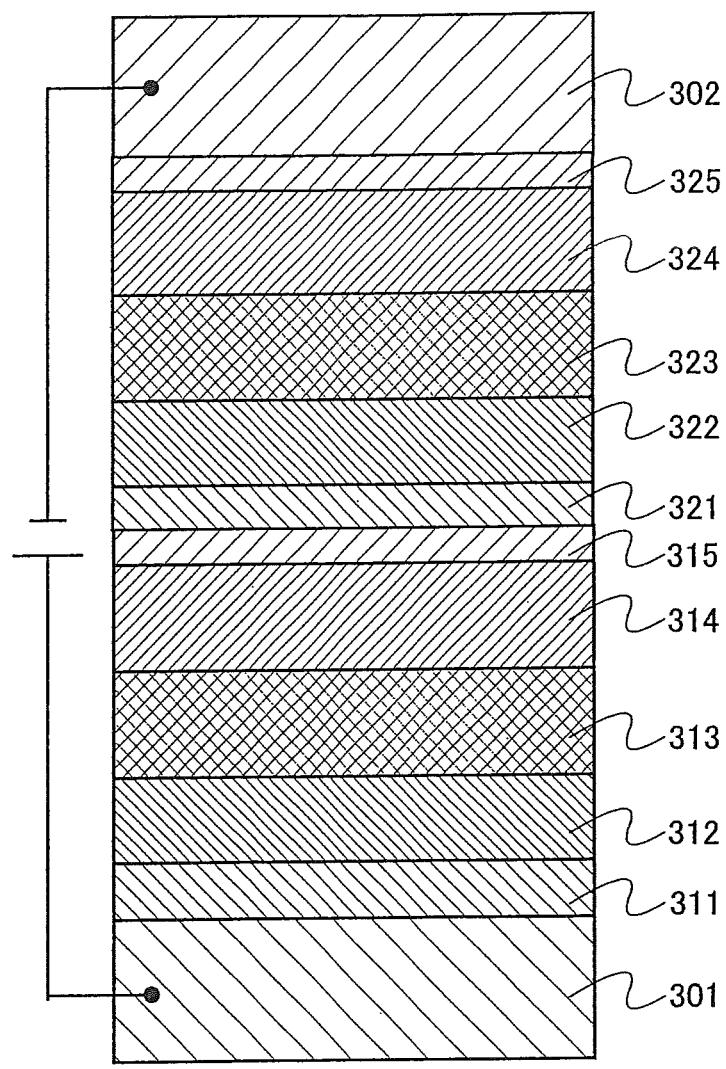
FIG. 3 shows a light emitting element of the present invention.

In the light emitting element of FIG. 3, a first light emitting layer 313 and a second light emitting layer 323 are provided between a first electrode 301 and a second electrode 302. An N layer 315 and a P layer 321 as charge generating layers are provided between the first light emitting layer 313 and the second light emitting layer 323.

The N layer 315 is a layer for generating electrons, and the P layer 321 is a layer for generating holes. When voltage is applied such that the potential of the first electrode 301 is higher than that of the second electrode 302, holes injected from the first electrode 301 and electrons injected from the N layer 315 are recombined in the first light emitting layer 313, and thus, a first light emitting substance included in the first light emitting layer 313 emits light. Further, electrons injected from the second electrode 302 and holes injected from the P layer 321 are recombined in the second light emitting layer 323, and thus, a second light emitting substance included in the second light emitting layer 323 emits light.

The first light emitting layer 313 may have a similar structure to the first light emitting layer 213 of Embodiment Mode 3, and light with a peak of emission spectrum in 450 mn to 510 nm (i.e., blue light to blue green light) can be emitted. The second light emitting layer 323 may have a similar structure to the second light emitting layer 215 of Embodiment Mode 3, and includes an organometallic complex of the present invention, and red light can be obtained. Since the organometallic complex of the present invention has high luminous efficiency, a light emitting element with high light emission efficiency can be obtained. Further, a light emitting element with reduced power consumption can be obtained.

Since the N layer 315 is a layer for generating electrons, it may be formed using a composite material in which the organic compound and the electron donor described in Embodiment Mode 2 are combined. By employing such a structure, electrons can be injected to the first light emitting layer 313 side.

Since the P layer 321 is a layer for generating holes, it may be formed using a composite material in which the organic compound and the electron donor described in Embodiment Mode 2 are combined. By employing such a structure, holes can be injected to the second light emitting layer 323 side. For the P layer 321, a metal oxide having an excellent hole injecting property, such as $MoO_x$, $VO_x$, ITO, or ITSO can be used.

Here, Embodiment Mode 4 describes a light emitting element in which the two light emitting layers are provided as shown in FIG. 3; however, the number of light emitting layers is not limited to two. For example, the number may be three as long as light from each light emitting layer are mixed. Consequently, white-color light can be obtained for example.

The first electrode 301 may have a similar structure to the first electrode 101 of Embodiment Mode 2. In addition, the second electrode 302 may have a similar structure to the second electrode 102 described in Embodiment Mode 2.

In Embodiment Mode 4, as shown in FIG. 3, a hole injecting layer 311, hole transporting layers 312 and 322, electron transporting layers 314 and 324, and an electron injecting layer 325 are provided. As to these layer structures, the structures of the respective layers described in Embodiment Mode 2 may also be applied. Note that these layers may be provided as appropriate depending on the element characteristics, since these layers are not necessarily provided.

Embodiment Mode 5

A mode of a light emitting element using the organometallic complex of the present invention as a sensitizer will be described with reference to FIG. 1.

FIG. 1 shows the light emitting element having the light emitting layer 113 between the first electrode 101 and the second electrode 102. The light emitting layer 113 contains the organometallic complex of the present invention described in Embodiment Mode 1, and a fluorescent compound which can emit light with a longer wavelength than the organometallic complex of the present invention.

In the light emitting element like this, holes injected from the first electrode 101 and electrons injected from the second electrode 102 are recombined in the light emitting layer 113 to bring the fluorescent compound to an excited state. Then, light is emitted when the fluorescent compound in the excited state returns to the ground state. In this case, the organometallic complex of the present invention acts as a sensitizer for the fluorescent compound to make more molecules of the fluorescent compound be in the singlet excited state. In this manner, a light emitting element with excellent light emission efficiency can be obtained by using the organometallic complex of the present invention as a sensitizer. It is to be noted that the first electrode 101 functions as an anode and the second electrode 102 functions as a cathode in the light emitting element of Embodiment Mode 5.

Here, the light emitting layer 113 includes an organometallic complex of the present invention, and a fluorescent compound which can emit light with a longer wavelength than the organometallic complex of the present invention. The light emitting layer 113 may preferably have a structure in which a substance having a larger singlet excitation energy than the fluorescent compound as well as a substance having a larger triplet excitation energy than the organometallic complex of the present invention is used as a host, and the organometallic complex of the present invention and the fluorescent compound are dispersedly contained as a guest.

There are no particular limitations on a substance (i.e., host) used for dispersing the organometallic complex of the present invention and the fluorescent compound, and a substance which is used as a host in Embodiment Mode 2, or the like can be used.

In addition, there are also no particular limitations on the fluorescent compound; however, a compound which can exhibit emission of red light to infrared light, such as 4-dicyanomethylene-2-isopropyl-6-[2-(1,1,7,7-tetramethyl-julolidin-9-yl)ethenyl]-4H-py ran (abbreviation: DCJTI), magnesium phthalocyanine, magnesium porphyrin, phthalocyanine or the like, is preferable.

Note that the first electrode 101 and the second electrode 102 may both have similar structures to the first electrode and the second electrode of Embodiment Mode 2, respectively.

In Embodiment Mode 5, as shown in FIG. 1, the hole injecting layer 111, the hole transporting layer 112, the electron transporting layer 114, and the electron injecting layer 115 are provided. As to these layers also, the structures of the respective layers described in Embodiment Mode 2 may be applied. Note that these layers may be provided as appropriate depending on the element characteristics, since these layers are not necessarily provided.

The foregoing light emitting element can emit light highly efficiently by using the organometallic complex of the present invention as a sensitizer.

Embodiment Mode 6

In Embodiment Mode 6, a light emitting device manufactured using an organometallic complex of the present invention will be described.

Figure 4A:
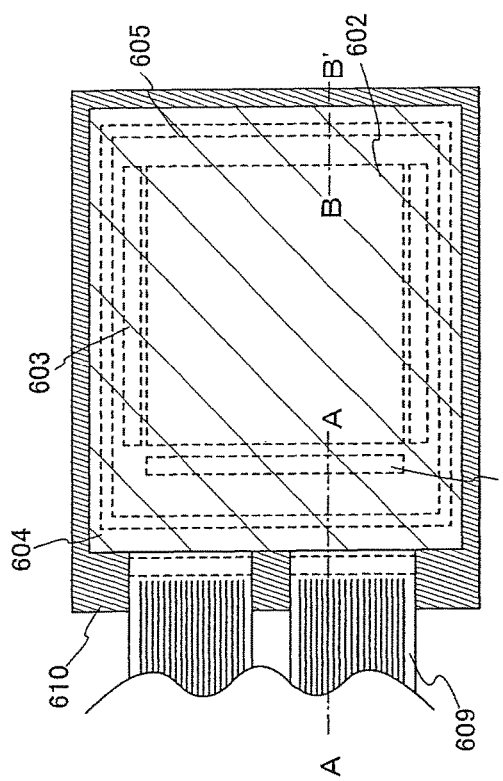
FIGS. 4A and 4B show a light emitting device of the present invention.
Figure 4B:
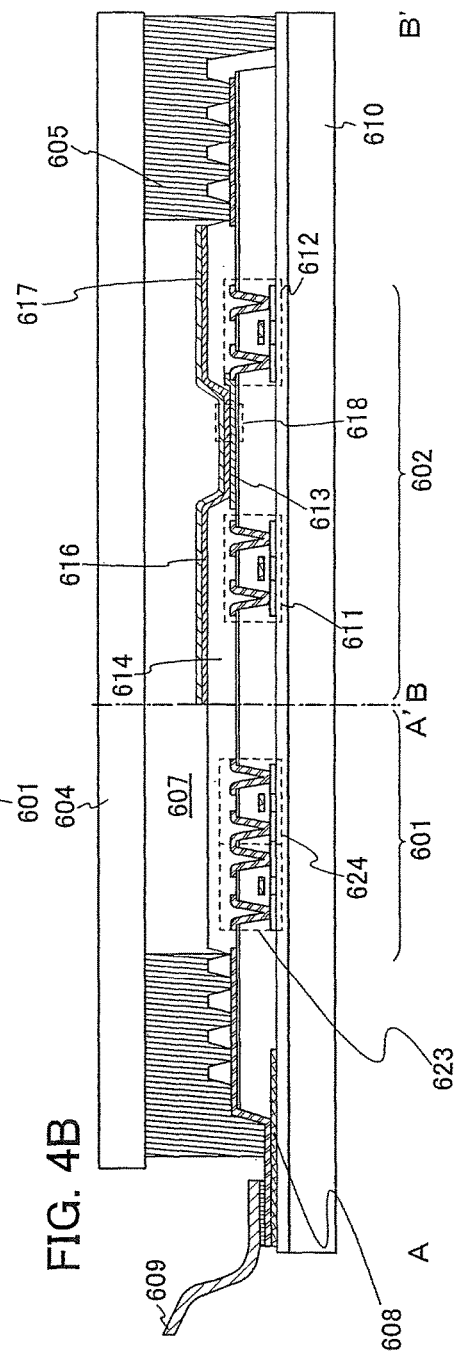

In this embodiment mode, a light emitting device manufactured using an organometallic complex of the present invention will be described with reference to FIGS. 4A and 4B. It is to be noted that FIG. 4A is a top view of a light emitting device and FIG. 4B is a cross sectional view of FIG. 4A taken along lines A-A' and B-B'. Reference numeral 601 denotes a driver circuit portion (source side driver circuit); 602 denotes a pixel portion; and 603 denotes a driver circuit portion (gate side driver circuit), which are indicated by dotted lines. Reference numeral 604 denotes a sealing substrate; 605 denotes a sealing material; and a portion surrounded by the sealing material 605 is a space 607.

In addition, a lead wiring 608 is a wiring for transmitting a signal to be inputted to the source side driver circuit 601 and the gate side driver circuit 603 and receives a video signal, a clock signal, a start signal, a reset signal, and the like from an FPC (flexible printed circuit) 609, which is an external input terminal. Note that only the FPC is shown here; however, the FPC may be provided with a printed wiring board (PWB). The light emitting device in this specification includes not only a light emitting device itself but also a light emitting device attached with an FPC or a PWB.

Next, a cross-sectional structure is described with reference to FIG. 4B. Although the driver circuit portion and the pixel portion are formed over an element substrate 610, the source side driver circuit 601 which is the driver circuit portion and one pixel in the pixel portion 602 are shown here.

A CMOS circuit, which has a combination of an n-channel TFT 623 and a p-channel 624, is fowled as the source side driver circuit 601. The driver circuit may be formed using various circuits such as a CMOS circuit, a PMOS circuit, or an NMOS circuit. Although a driver integration type in which a driver circuit is formed over a substrate is described in this embodiment mode, a driver circuit is not necessarily formed over a substrate and can be formed outside a substrate.

Further, the pixel portion 602 has a plurality of pixels, each of which includes a switching TFT 611, a current control TFT 612, and a first electrode 613 which is electrically connected to the drain of the current control TFT 612. Note that an insulator 614 is formed so as to cover an end portion of the first electrode 613. Here, a positive photosensitive acrylic resin film is used for the insulator 614.

The insulator 614 is formed so as to have a curved surface having curvature at an upper end portion or a lower end portion thereof in order to make the coverage favorable. For example, in the case of using a positive photosensitive acrylic resin as a material for the insulator 614, the insulator 614 is preferably formed so as to have a curved surface with a curvature radius (0.2 μm to 3 μm) only at the upper end portion thereof. Either a negative type which becomes insoluble in an etchant by light irradiation or a positive type which becomes soluble in an etchant by light irradiation can be used as the insulator 614.

A layer 616 containing a light emitting substance and a second electrode 617 are formed over the first electrode 613. Here, a material having a high work function is preferably used as a material for the first electrode 613, which serves as an anode. For example, the first electrode 613 can be formed with the used of stacked layers of a titanium nitride film and a film containing aluminum as its main component; a three-layer structure of a titanium nitride film, a film containing aluminum as its main component, and another titanium nitride film; or the like as well as a single-layer film such as an ITO film, an indium tin oxide film containing silicon, an indium oxide film containing zinc oxide of 2 to 20 wt %, a titanium nitride film, a chromium film, a tungsten film, a Zn film, or a Pt film. When the first electrode 613 has a stacked layer structure, it can have low resistance as wiring and form a favorable ohmic contact. Further, the first electrode 613 can function as an anode.

In addition, the layer 616 containing a light emitting substance is formed by various methods such as an evaporation method using an evaporation mask, an ink-jet method, and a spin coating method. The layer 616 containing a light emitting substance has the organometallic complex of the present invention described in Embodiment Mode 1. Further, the layer 616 containing a light emitting substance may include another material such as a low molecular material, a medium molecular material (including an oligomer and a dendrimer), or a high molecular material.

As a material used for the second electrode 617, which is formed over the layer 616 containing a light emitting substance and serves as a cathode, a material having a low work function (Al, Mg, Li, Ca, or an alloy or a compound of them such as MgAg, MgIn, AlLi, LiF, or $CaF_2$) is preferably used. In the case where light generated in the layer 616 containing a light emitting substance is transmitted through the second electrode 617, stacked layers of a metal thin film and a light-transmissive conductive film (of ITO, indium oxide containing zinc oxide of 2 to 20 wt %, indium tin oxide containing silicon, zinc oxide (ZnO), or the like) are preferably used as the second. electrode 617.

By attaching the sealing substrate 604 to the element substrate 610 with the sealing material 605, a light emitting element 618 is provided in the space 607 surrounded by the element substrate 610, the sealing substrate 604, and the sealing material 605. It is to be noted that the space 607 is filled with a filler. There is a case where the space 607 is filled with the sealing material 605 as well as an inert gas (nitrogen, argon, or the like).

It is to be noted that an epoxy-based resin is preferably used as the sealing material 605. The material desirably allows as little moisture and oxygen as possible to penetrate. As the sealing substrate 604, a plastic substrate made of FRP (Fiberglass-Reinforced Plastics), PVF (polyvinyl fluoride), polyester, acrylic, or the like can be used besides a glass substrate or a quartz substrate.

In the above-described manner, a light emitting device manufactured using the oganometallic complex of the present invention can be obtained.

A light emitting device of the present invention can have favorable characteristics since the oganometallic complex described in Embodiment Mode 1 is used for the light emitting device. Specifically, since the light emitting element with high light emission efficiency is included, a light emitting device with reduced power consumption can be obtained. Further, since light emission of red color with high luminous efficiency can be realized, a light emitting device with reduced power consumption and excellent color reproductivity, which is suitable for a full-color display, can be obtained.

Figure 5:
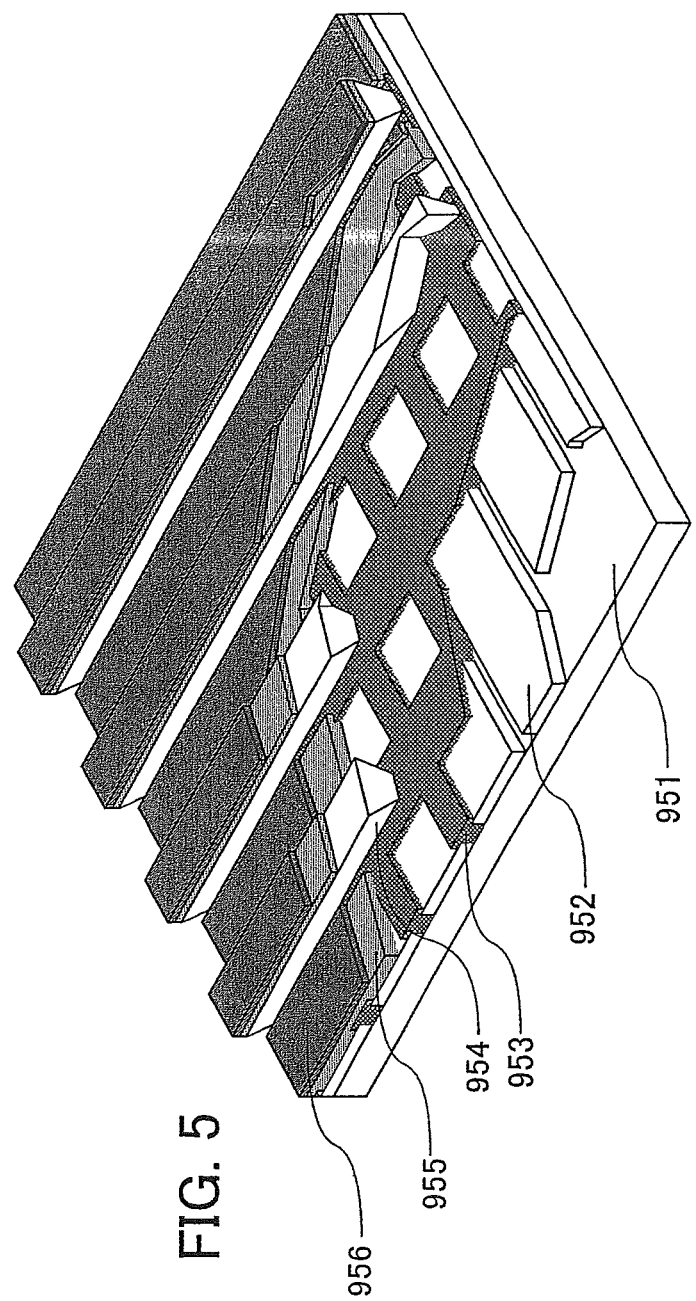
FIG. 5 shows a light emitting device of the present invention.

In this embodiment mode, description is made of an active light emitting device for controlling driving of a light emitting element with a transistor. Alternatively, a passive light emitting device which drives a light emitting element without particularly providing an element for driving such as a transistor may also be used. FIG. 5 shows a perspective view of a passive light emitting device which is manufactured by using the present invention. In FIG. 5, a layer 955 containing a light emitting substance is provided between an electrode 952 and an electrode 956 over a substrate 951. An edge portion of the electrode 952 is covered with an insulating layer 953. Then, a partition layer 954 is provided over the insulating layer 953. Side walls of the partition layer 954 slope so that a distance between one side wall and the other side wall becomes narrower toward a substrate surface. In other words, a cross section of the partition layer 954 in the direction of a short side is trapezoidal, and a base (side which is provided in the same direction as a plane direction of the insulating layer 953 and in contact with the insulating layer 953) is shorter than an upper side (side which is provided in the same direction as the plane direction of the insulating layer 953 and not in contact with the insulating layer 953). By providing the partition layer 954 in this manner, a defect of the light emitting element due to static electricity or the like can be prevented. In addition, the passive light emitting device can also be driven with low power consumption when it includes the light emitting element having high light emission efficiency of the present invention.

Embodiment Mode 7

In Embodiment Mode 7, an electronic device of the present invention including the light emitting device described in Embodiment Mode 6 as a part will be described.

The electronic device of the present invention including the organometallic complex described in Embodiment Mode 1 has a display portion with high light emission efficiency and reduced power consumption. Further, it also includes a display portion with excellent color reproductivity. In the case where the organometallic complex of the present invention is used for a full-color display, various light emitting substances can be used for a light emitting element of a color other than red color and a light emitting element having a similar structure to that described in Embodiment Modes 2 to 5 can be employed.

As an electronic device including a light emitting element manufactured using the organometallic complex of the present invention, a camera such as a video camera or a digital camera, a goggle type display, a navigation system, an audio reproducing device (car audio component stereo, audio component stereo, or the like), a computer, a game machine, a portable information terminal (mobile computer, mobile phone, portable game machine, electronic book, or the like), and an image reproducing device provided with a recording medium (specifically, a device capable of reproducing a recording medium such as a Digital Versatile Disc (DVD) and provided with a display device that can display the image), and the like are given. Specific examples of these electronic device are shown in FIGS. 6A to 6D.

Figure 6A:
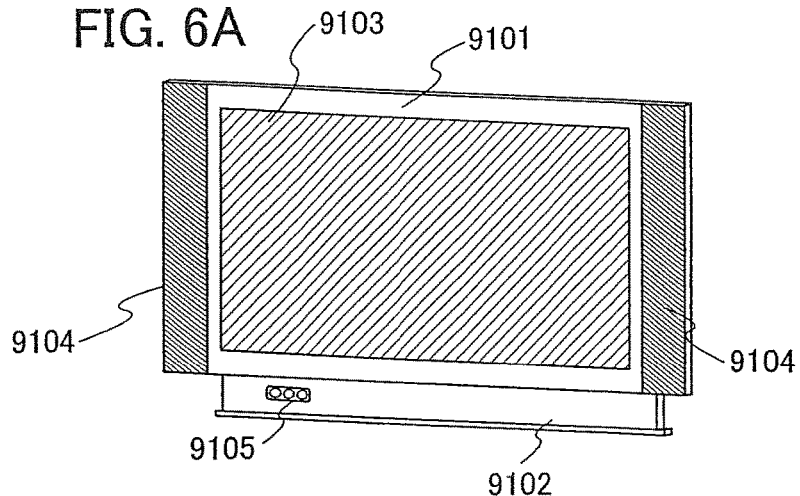
FIGS. 6A to 6D show electronic devices of the present invention.

FIG. 6A shows a television device according to the present invention, which includes a housing 9101, a supporting base 9102, a display portion 9103, a speaker portion 9104, a video input terminal 9105, and the like. In the television device, the display portion 9103 has light emitting elements similar to those described in Embodiment Modes 2 to 5, which are arranged in matrix. One feature of the light emitting element is that high light emission efficiency and low power consumption are possible. In addition, light emission of red color with high luminous efficiency can be realized. The display portion 9103 which includes the light emitting elements has similar features. Therefore, in the television device, image quality is hardly deteriorated and low power consumption is achieved. With such features, deterioration compensation functions and power supply circuits can be significantly reduced or downsized in the television device; therefore, small size and lightweight housing 9101 and supporting base 9102 can be achieved. In the television device according to the present invention, low power consumption, high image quality, and small size and lightweight are achieved; therefore, a product which is suitable for any residential environment can be provided. Further, since the light emitting element capable of emitting red light with high luminous efficiency is included, a television device having a display portion with low power consumption and excellent color reproductivity can be obtained.

Figure 6B:
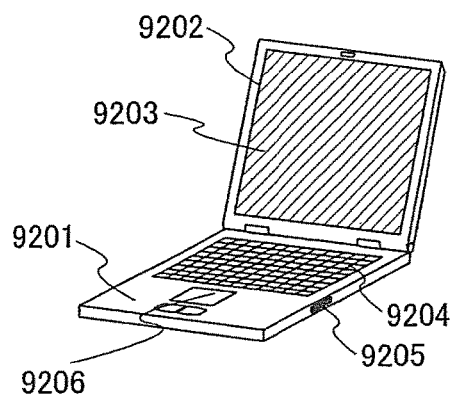

FIG. 6B shows a computer according to the present invention, which includes a main body 9201, a housing 9202, a display portion 9203, a keyboard 9204, an external connection port 9205, a pointing mouse 9206, and the like. In the computer, the display portion 9203 has light emitting elements similar to those described in Embodiment Modes 2 to 5, which are arranged in matrix. One feature of the light emitting element is that high light emission efficiency and low power consumption are possible. In addition, light emission of red color with high luminous efficiency can be realized. The display portion 9203 which includes the light emitting elements has similar features. Therefore, in the computer, image quality is hardly deteriorated and lower power consumption is achieved. With such features, deterioration compensation functions and power supply circuits can be significantly reduced or downsized in the computer; therefore, small size and lightweight main body 9201 and housing 9202 can be achieved. In the computer according to the present invention, low power consumption, high image quality, and small size and lightweight are achieved; therefore, a product which is suitable for any residential environment can be provided. Further, since the light emitting element capable of emitting red light with high luminous efficiency is included, a computer having a display portion with low power consumption and excellent color reproductivity can be obtained.

Figure 6C:
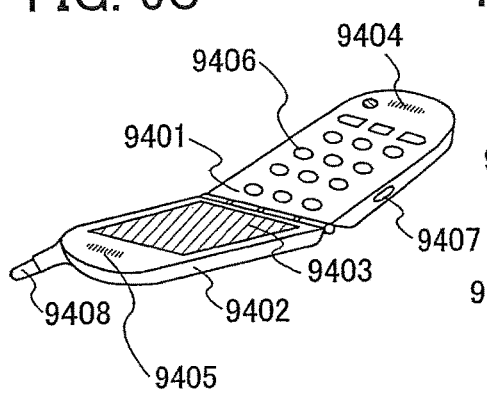

FIG. 6C shows a mobile phone according to the present invention, which includes a main body 9401, a housing 9402, a display portion 9403, an audio input portion 9404, an audio output portion 9405, an operation key 9406, an external connection port 9407, an antenna 9408, and the like. In the mobile phone, the display portion 9403 has light emitting elements similar to those described in Embodiment Modes 2 to 5, which are arranged in matrix. One feature of the light emitting element is that high light emission efficiency and low power consumption are possible. In addition, light emission of red color with high luminous efficiency can be realized. The display portion 9403 which includes the light emitting elements has similar features. Therefore, in the mobile phone, image quality is hardly deteriorated and lower power consumption is achieved. With such features, deterioration compensation functions and power supply circuits can be significantly reduced or downsized in the mobile phone; therefore, small size and lightweight main body 9401 and the housing 9402 can be achieved. In the mobile phone according to the present invention, low power consumption, high image quality, and small size and lightweight are achieved; therefore, a production which is suitable for carrying can be provided. Further, since the light emitting element capable of emitting red light with high luminous efficiency is included, a mobile phone having a display portion with low power consumption and excellent color reproductivity can be obtained.

Figure 6D:
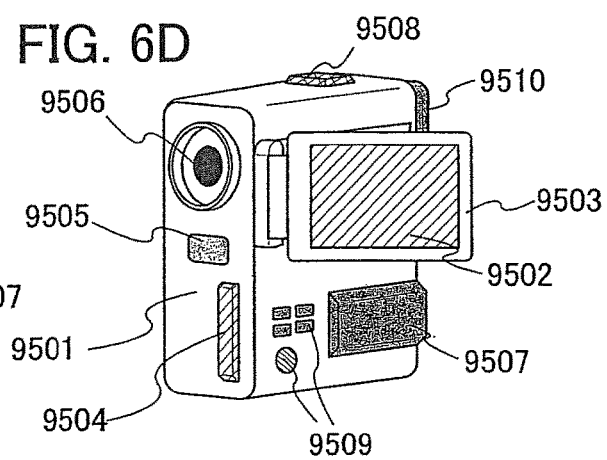

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In this camera, the display portion 9502 has light emitting elements similar to those described in Embodiment Modes 2 to 5, which are arranged in matrix. One feature of the light emitting element is that high light emission efficiency and low power consumption are possible. In addition, light emission of red color with high luminous efficiency can be realized. The display portion 9502 which includes the light emitting elements has similar features. Therefore, in the camera, image quality is hardly deteriorated and lower power consumption can be achieved. With such features, deterioration compensation functions and power supply circuits can be significantly reduced or downsized in the camera; therefore, small size and lightweight main body 9501 can be achieved. In the camera according to the present invention, low power consumption, high image quality, and small size and lightweight are achieved; therefore, a product which is suitable for carrying can be provided. Further, since the light emitting element capable of emitting red light with high luminous efficiency is included, a camera having a display portion with low power consumption and excellent color reproductivity can be obtained.

As described above, the applicable range of the light emitting device of the present invention is so wide that the light emitting device can be applied to electronic devices in various fields. By using the organometallic complex of the present invention, electronic devices which have display portions consuming low power and having excellent color reproductivity can be provided.

The light emitting device of the present invention can also be used as a lighting device. One mode using the light emitting element of the present invention as the lighting device is described with reference to FIG. 7.

Figure 7:
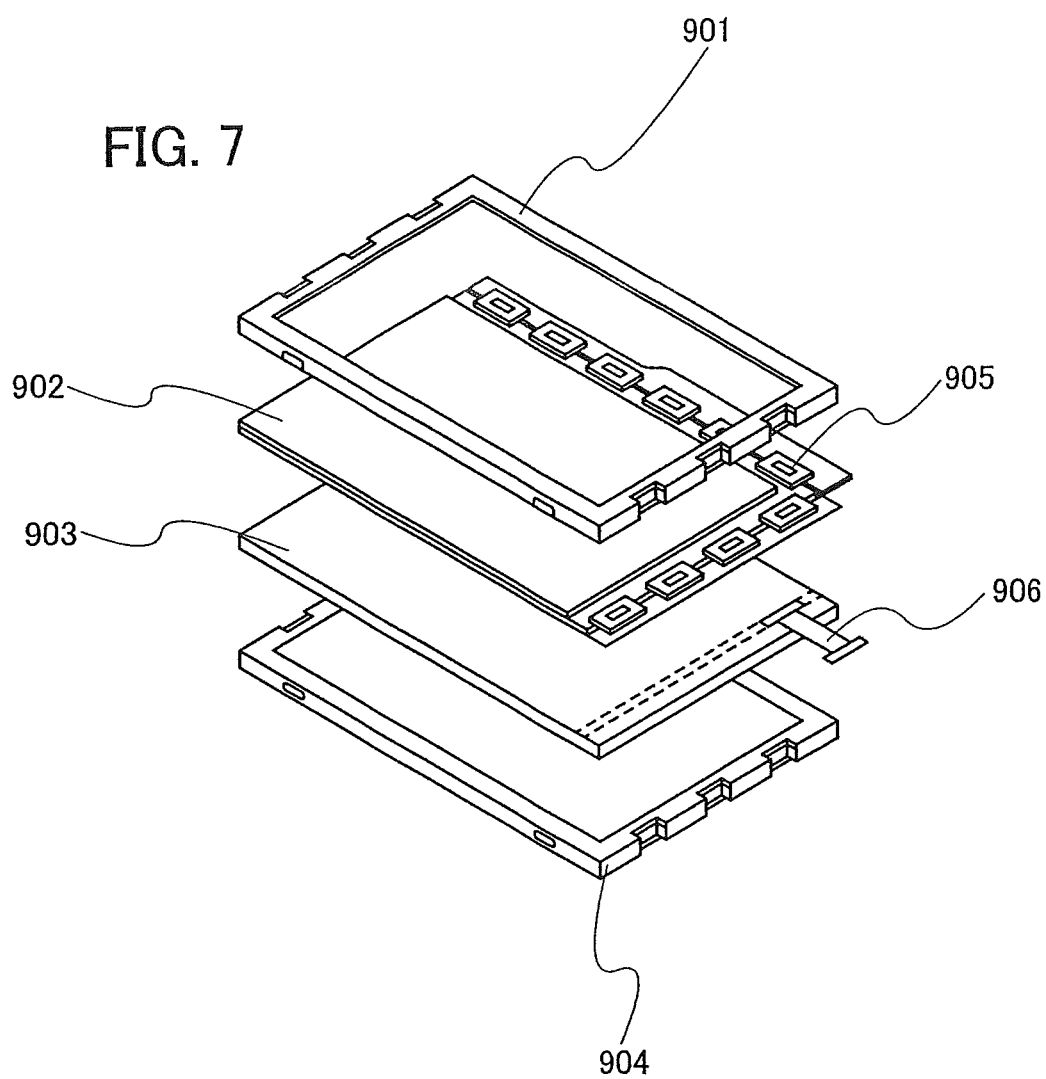
FIG. 7 shows an electronic device of the present invention.

FIG. 7 shows an example of a liquid crystal display device using the light emitting device of the present invention as a backlight. The liquid crystal display device shown in FIG. 7 includes a housing 901, a liquid crystal layer 902, a backlight 903, and a housing 904, and the liquid crystal layer 902 is connected to a driver IC 905. The light emitting device of the present invention is used for the backlight 903, and current is supplied through a terminal 906.

By using the light emitting device of the present invention as the backlight of the liquid crystal display device, a backlight with reduced power consumption can be obtained. The light emitting device of the present invention is a lighting device with plane light emission, and can have a large area. Therefore, the backlight can have a large area, and a liquid crystal display device having a large area can be realized. Furthermore, the light emitting device of the present invention has a thin shape and consumes low power; therefore, a thin shape and low power consumption of a display device can also be achieved.

Figure 8:
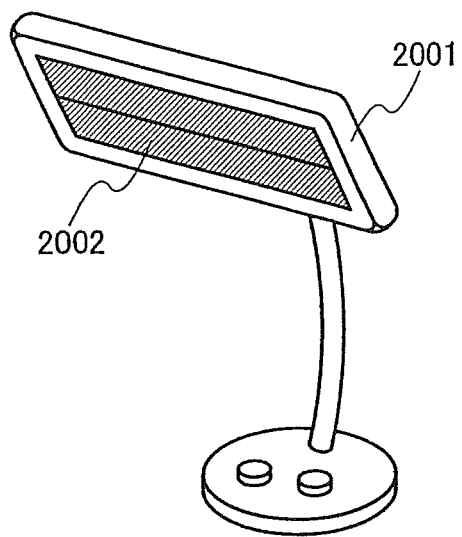
FIG. 8 shows a lighting device of the present invention.

FIG. 8 shows an example of using the light emitting device to which the present invention is applied as a table lamp, which is a lighting device. A table lamp shown in FIG. 8 has a chassis 2001 and a light source 2002, and the light emitting device of the present invention is used as the light source 2002. The light emitting device of the present invention can emit light with high luminance; therefore, in such a case where fine manipulation is performed, the manipulator's hand can be brightly lighted.

FIG. 9 shows an example of using the light emitting device to which the present invention is applied as an indoor lighting device 3001. Since the light emitting device of the present invention can have a large area, the light emitting device of the present invention can be used as a lighting device having a large area. Further, the light emitting device of the present invention has a thin shape and consumes low power; therefore, the light emitting device of the present invention can be used as a lighting device having a thin shape and consuming low power. A television device relating to the present invention as shown in FIG. 6A is placed in a room where the light emitting device to which the present invention is applied is used as the indoor lighting device 3001. Thus, public broadcasting and movies can be watched. In such a case, since both of the devices consume low power, a powerful image can be watched in a bright room without concern about electricity charges.

EXAMPLE 1

SYNTHETIC EXAMPLE 1

In Synthetic Example 1, a synthetic example of an organometallic complex of the present invention represented by structural formula (1) in Embodiment Mode 1, (acetylacetonato)bis(2,3,5-triphenylpyrazinato)iridium(III) (abbreviation: [Ir(tppr)$_2$(acac)]), will be specifically described.

Step 1: Synthesis of 2,3,5-triphenylpyrazine (abbreviation: Htppr)

First, in a nitrogen atmosphere, 5.5 mL of a dibutyl ether solution containing phenyl lithium (produced by Wako Pure Chemical Industries, Ltd., 2.1 mol/L) and 50 mL of diethylether were mixed to prepare a solution. Then, 2.43 g of 2,3-diphenylpyrazine was dropped into this solution while the solution was being cooled with ice, and stirred at a room temperature for 24 hours. After the stirring, water was added into the mixture and an organic layer was extracted with diethylether. The extracted organic layer was washed with water and dried with magnesium sulfate. After the drying, the organic layer was added with activated manganese dioxide excessively, mixed sufficiently, and then filtered. A solvent of the filtrate was distilled off, and a residue obtained was recrystallized with ethanol so that a pyrazine derivative, Htppr (yellow powder, yield of 56%), was obtained. A synthetic scheme of Step 1 is shown in the following (a-1).

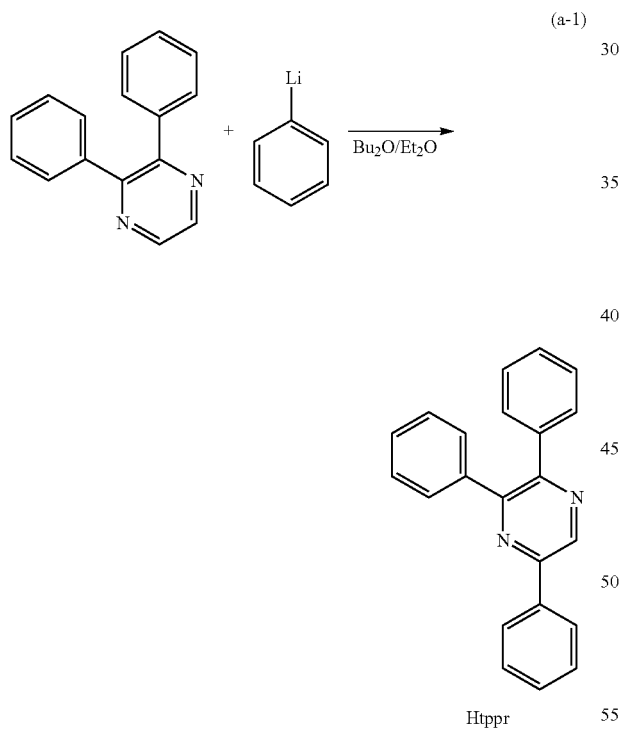

Step 2: Synthesis of di-µ-chloro-bis[bis(2,3,5-triphenylpyrazinato)iridium(III)] (abbreviation: [Ir(tppr)$_2$Cl]$_2$)

Next, 1.08 g of the pyrazine derivative Htppr obtained in the above step 1 and 0.73 g of iridium chloride hydrate (IrCl$_3$·H$_2$O) (produced by Sigma-Aldrich Corp.) were mixed in a mixed solution containing 30 mL of 2-ethoxyethanol and 10 mL of water, and the mixture was refluxed in a nitrogen atmosphere for 16 hours. A powder precipitated was filtered and washed with ethanol, ether, and then hexane; thereby obtaining a dinuclear complex [Ir(tppr)$_2$Cl]$_2$ (orange powder, yield of 97%). A synthetic scheme of Step 2 is shown in the following (b-1).

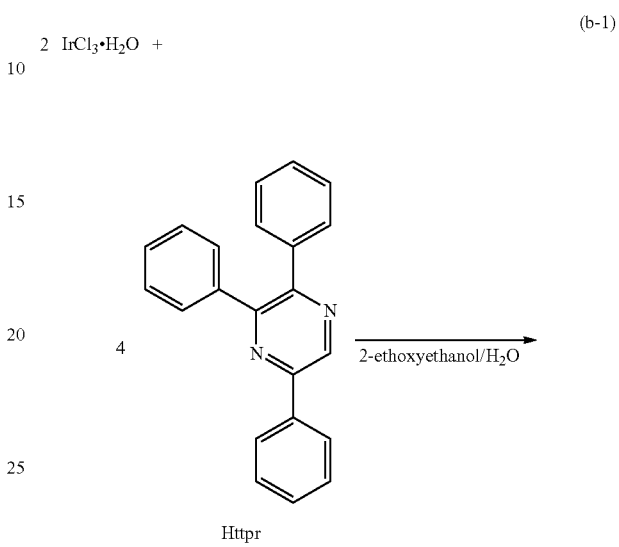

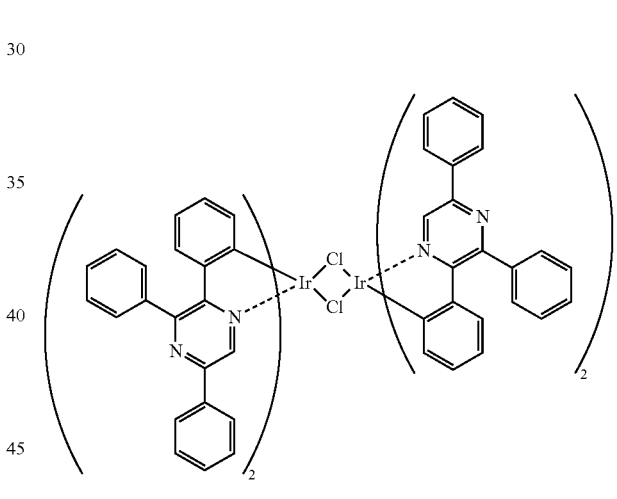

Step 3: Synthesis of (acetylacetonato)bis(2,3,5-triphenylpyrazinato)iridium(III) (abbreviation: [Ir(tppr)$_2$(acac)])

Further, 2.00 g of the dinuclear complex [Ir(tppr)$_2$Cl]$_2$ obtained in the above step 2, 0.37 mL of acetylacetone and 1.26 g of sodium carbonate were mixed in a solvent of 2-ethoxyethanol (40 mL), and the mixture was refluxed in a nitrogen atmosphere for 18 hours. After the reflux, the mixture was filtered and the filtrate was left for one week. Then, a crystal precipitated was removed by filtration and a solvent of the filtrate was distilled off. A residue obtained was recrystallized with a mixed solvent of dichloromethane and ethanol. A powder obtained by the recrystallization was washed with ethanol and then ether; thereby obtaining an organometallic complex [Ir(tppr)$_2$(acac)] of the present invention (red powder, yield of 16%). A synthetic scheme of Step 3 is shown in the following (c-1).

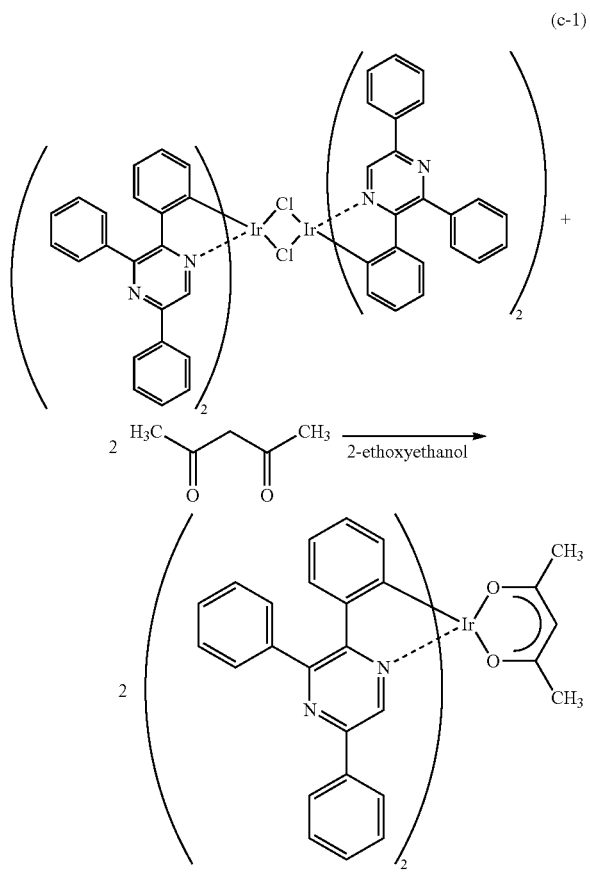

(c-1)

Figure 10A:
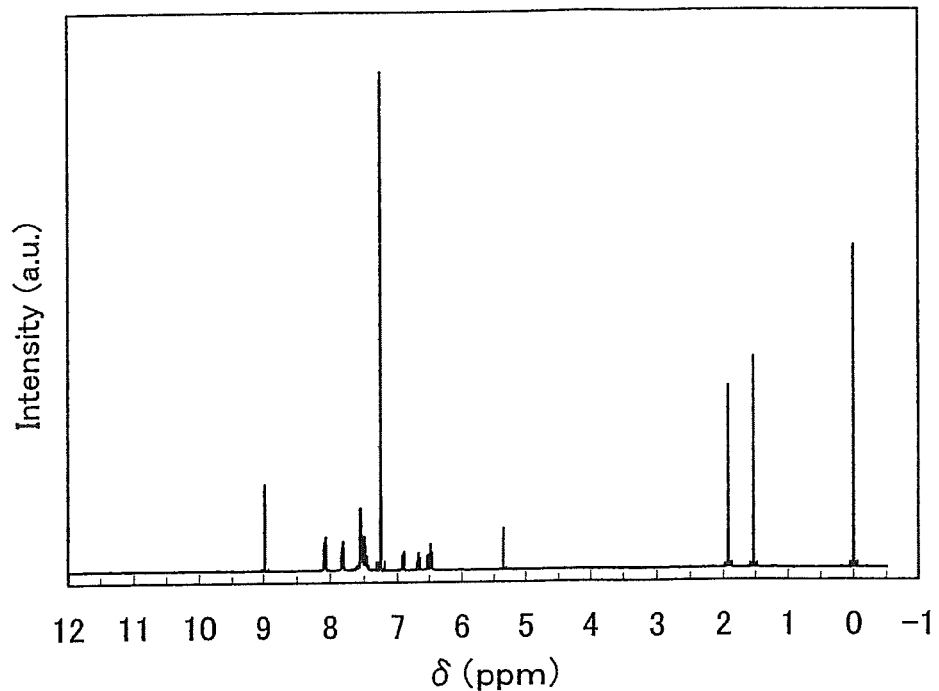
FIGS. 10A and 10B show a $^1$H-NMR chart of (acetylacetonato)bis(2,3,5-triphenylpyrazinato)iridium(III)
Figure 10B:
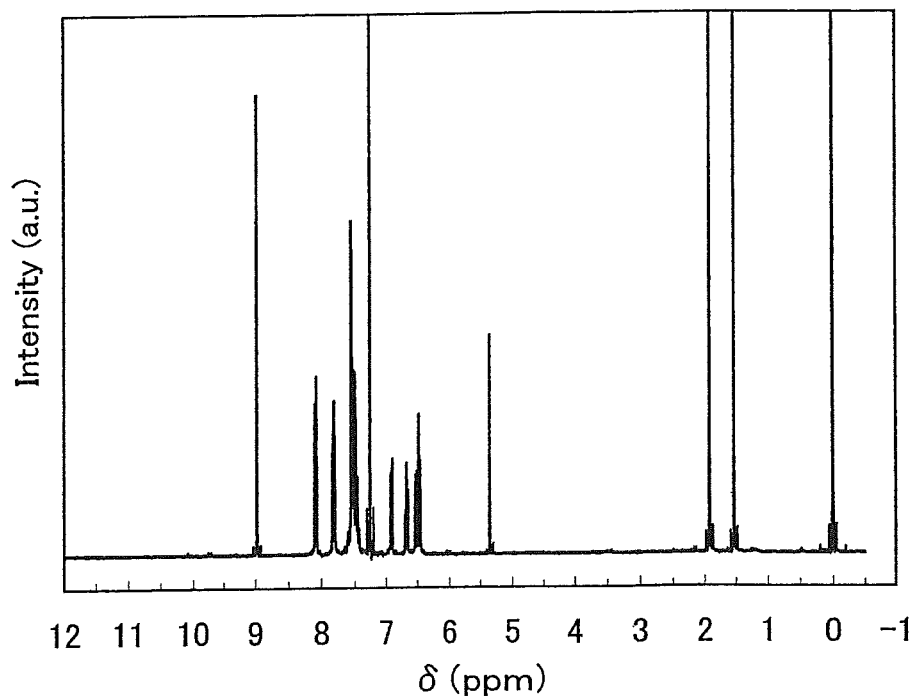

An analysis result of the red powder obtained in Step 3 by nuclear magnetic resonance spectrometry ($^1$H-NMR) is shown below. A $^1$H-NMR chart is shown in FIGS. 10A and 10B. FIG. 10B shows an enlarged view of FIG. 10A in the vertical axis direction. From FIGS. 10A and 10B, it was found that the organometallic complex [Ir(tppr)$_2$(acac)] of the present invention represented by the above structural formula (1) was obtained in Synthetic Example 1.

$^1$H-NMR. δ (CDCl$_3$): 1.92 (s, 6H), 5.35 (s, 1H), 6.45-6.54 (m, 4H), 6.67 (td, 2H), 6.91 (d, 2H), 7.41-7.57 (m, 12H), 7.81 (m, 4H), 8.08 (dd, 4H), 8.98 (s, 2H).

A decomposition temperature T$_d$ of the obtained organometallic complex [Ir(tppr)$_2$(acac)] of the present invention was measured by Thermo-Gravimetric/Differential Thermal Analyzer (manufactured by Seiko Instrument Inc., TG/DTA 320 type), and the result was T$_d$=331° C. It was found that the obtained product showed favorable heat resistance.

Figure 11:
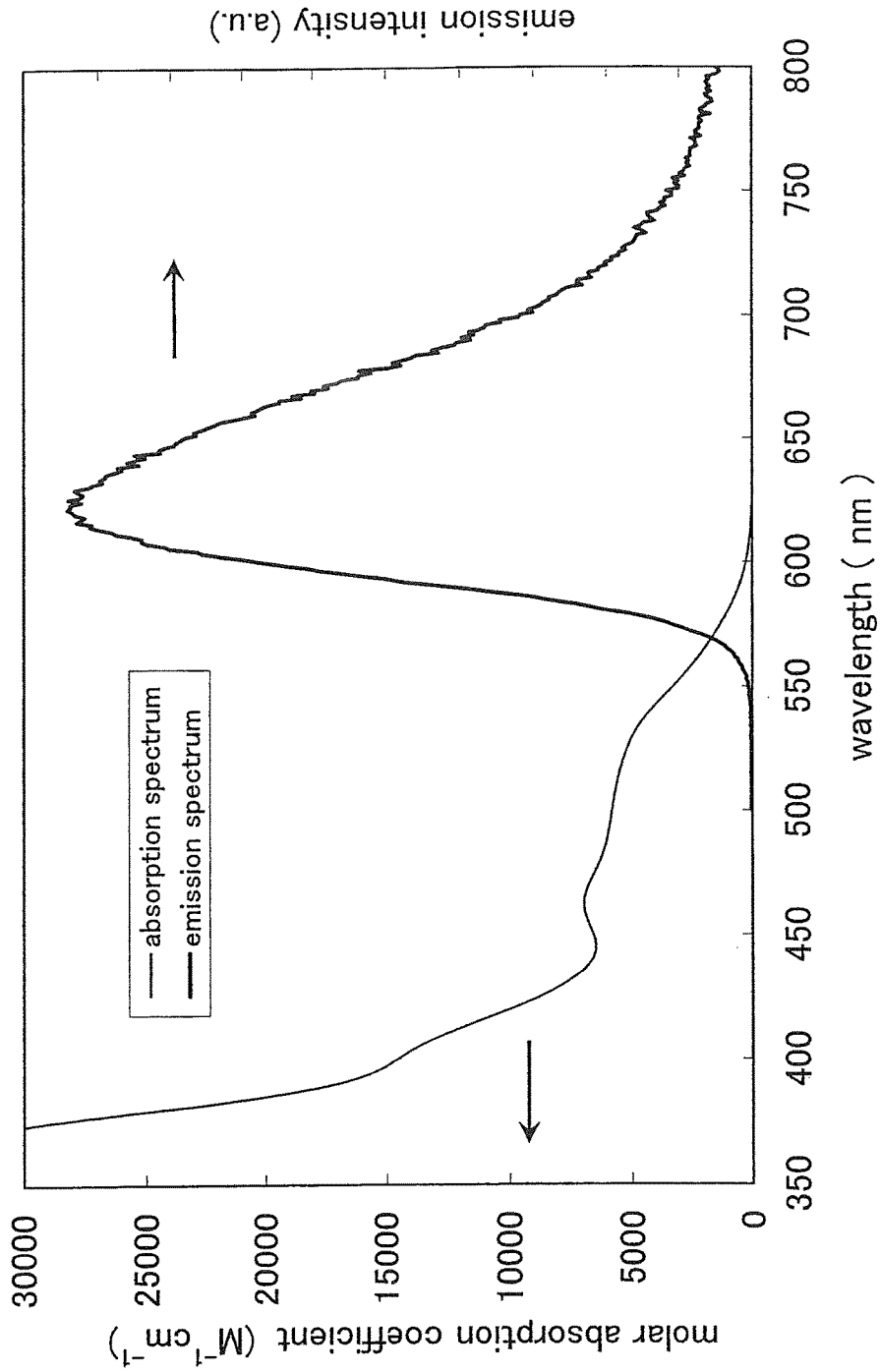
FIG. 11 shows an absorption spectrum and an emission spectrum of (acetylacetonato)bis(2,3,5-triphenylpyrazinato)iridium(III)

Next, an absorption spectrum of [Ir(tppr)$_2$(acac)] was measured with the use of an ultraviolet-visible light spectrophotometer (manufactured by Japan Spectroscopy Corporation, V550 type). The measurement was conducted by using a degassed dichloromethane solution (0.10 mmol/L) at a room temperature. In addition, an emission spectrum of [Ir(tppr)$_2$(acac)] was measured with the use of a fluorescence spectrophotometer (manufactured by Hamamatsu Photonics Corporation, FS920). The measurement was conducted by using a degassed dichloromethane solution (0.35 mmol/L) at a room temperature. FIG. 11 shows the measurement results. The horizontal axis indicates a wavelength and the vertical axis indicates a molar absorption coefficient and emission intensity.

As shown in FIG. 11, the organometallic complex [Ir(tppr)$_2$(acac)] of the present invention has a peak of emission spectrum at 622 nm, and red-orange light was observed from the solution.

Further, it is observed that the organometallic complex [Ir(tppr)$_2$(acac)] of the present invention has several absorption peaks in a visible light region. This is an absorption unique to some organometallic complexes, which is often observed in an ortho-metalated complex or the like, and is considered to correspond to singlet MLCT transition, triplet π-π* transition, triplet MLCT transition, or the like. In particular, the absorption peak having the longest wavelength spreads broadly in the visible light region, which would be owing to triplet MLCT transition. In other words, it was found that the organometallic complex [Ir(tppr)$_2$(acac)] of the present invention was a compound capable of direct photo-excitation to a triplet excited state and intersystem crossing. Therefore, it can be considered that obtained emission was light emission from the triplet excited state, in other words, phosphorescence.

SYNTHETIC EXAMPLE 2

In Synthetic Example 2, a synthetic method of 2,3,5-triphenylpyrazine (abbreviation: Htppr), which was synthesized in the above Step 1 of Synthetic Example 1, different from the method of Synthetic Example 1, will be described.

First, 4.60 g of phenylglyoxal (produced by Tokyo Chemical Industries Co., Ltd.) and 7.28 g of meso-1,2-diphenylethylenediamine (produced by Sigma-Aldrich Corp.) were mixed in a solvent of ethanol (200 mL), and the mixture was refluxed in a nitrogen atmosphere for 6 hours. After the reflux, a solvent of this mixture was distilled off, and a residue obtained was recrystallized with ethanol. An ocher powder obtained by the recrystallization was dissolved in dichloromethane, and this solution was added with activated manganese dioxide excessively, mixed sufficiently, and then filtered. After a solvent of the filtrate was distilled off, a residue obtained was recrystallized with ethanol; thereby obtaining a pyrazine derivative Htppr (yellow powder, yield of 37%). A synthetic scheme of Synthetic Example 2 is shown in the following (a-1-2).

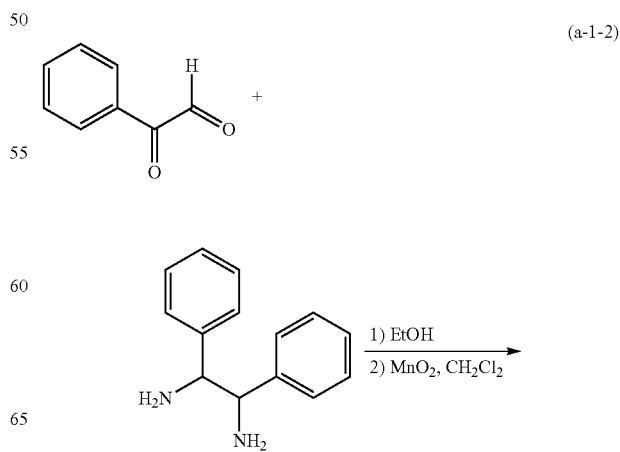

(a-1-2)

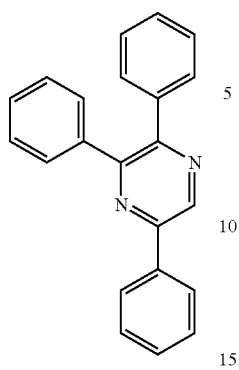

EXAMPLE 2

Figure 12:
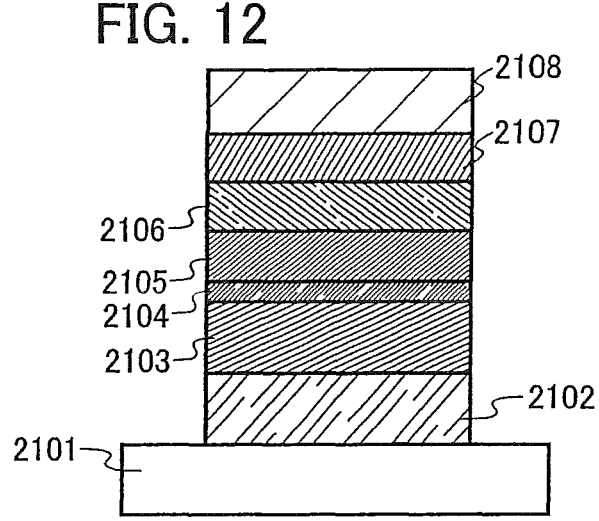
FIG. 12 shows a light emitting element of examples.

Example 2 will describe a light emitting element of the present invention with reference to FIG. 12. Chemical formulae of materials used in Examples 2 and 3 are shown below.

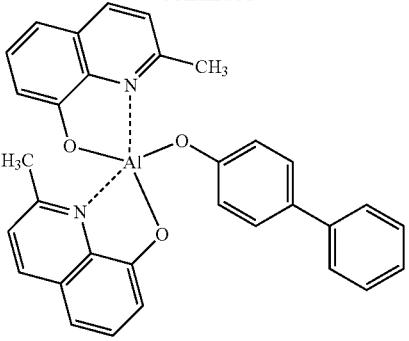

BAlq

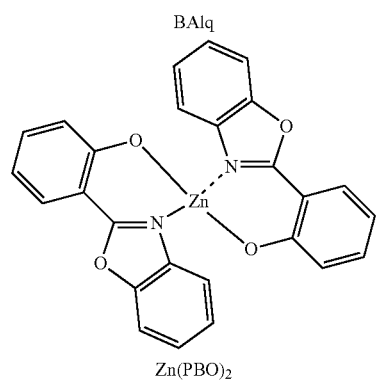

Zn(PBO)$_2$

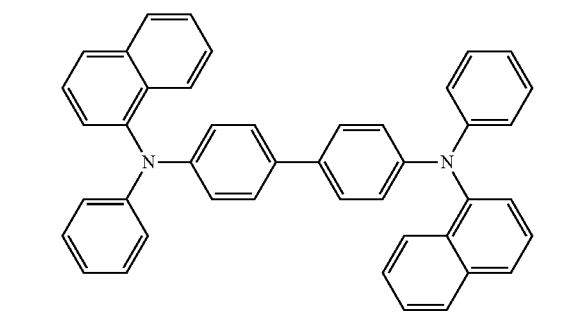

NPB

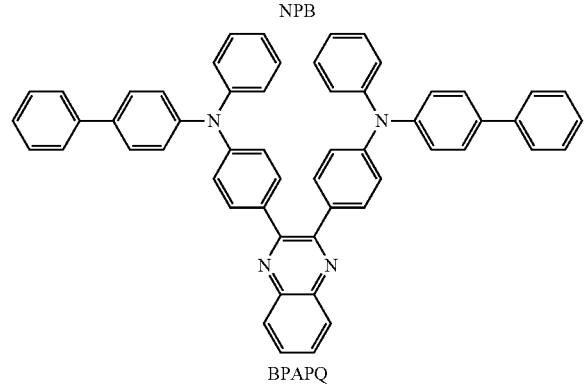

BPAPQ

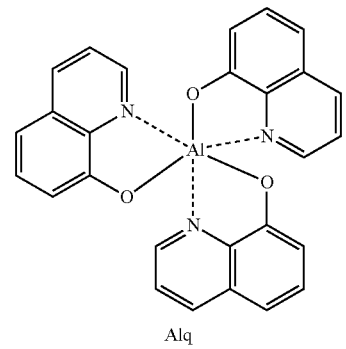

Alq (Light Emitting Element 1)

First, indium tin oxide containing silicon oxide was formed over a glass substrate 2101 by sputtering as a first electrode 2102. The film thickness of the first electrode 2102 was 110 nm and the area thereof was 2 mm×2 mm.

Then, the substrate provided with the first electrode was fixed on a substrate holder which was provided in a vacuum evaporation apparatus, in such a way that a surface provided with the first electrode faced downward. After that, the air inside the vacuum evaporation apparatus was evacuated to approximately 10-4 Pa. Then, a layer 2103 including a composite material including an organic compound and an inorganic compound was formed on the first electrode 2102 by co-evaporation of NPB and molybdenum (VI) oxide. The film thickness was 50 nm and the weight ratio between NPB and molybdenum (VI) oxide was adjusted to be 4:1 (=NPB: molybdenum oxide). It is to be noted that the co-evaporation is an evaporation method by which evaporation is carried out simultaneously from a plurality of evaporation sources in one process chamber.

Next, a hole transporting layer 2104 was formed on the layer including the composite material 2103 to have a thickness of 10 nm using 4,4'-bis[N-(1-naphthyl)-N-phenylamino]biphenyl (abbreviation: NPB) by evaporation using resistance heating.

Further, a light emitting layer 2105 was formed on the hole transporting layer 2104 to have a thickness of 30 nm by co-evaporation of 2,3-bis{4-[N-(4-biphenylyl)-N-phenylamino]phenyl}quinoxaline (abbreviation: BPAPQ) and (acetylacetonato)bis(2,3,5-triphenylpyrazinato)iridium(III) (abbreviation: Ir(tppr)$_2$(acac)) which is expressed by the structural formula (1). Here, the weight ratio between BPAPQ and Ir(tppr)$_2$(acac) was adjusted to be 1:0.05 BPAPQ: Ir(tppr)$_2$(acac)).

After that, an electron transporting layer 2106 was formed on the light emitting layer 2105 by depositing bis(2-methyl-8-quinolinolato)(4-phenylphenolato)aluminum (abbreviation: BAlq) so as to have a thickness of 10 nm by evaporation using resistance heating.

Further, an electron injecting layer 2107 was formed on the electron transporting layer 2106 so as to have a thickness of 50 nm by co-evaporation of tris(8-quinolinolato)aluminum (abbreviation: Alq) and lithium. The weight ratio between Alq and lithium was adjusted to be 1:0.01 (=Alq: lithium).

Finally, a second electrode 2108 was formed on the electron injecting layer 2107 by depositing aluminum so as to have a thickness of 200 nm by evaporation using resistance heating. Thus, the light emitting element 1 was formed.

Figure 13:
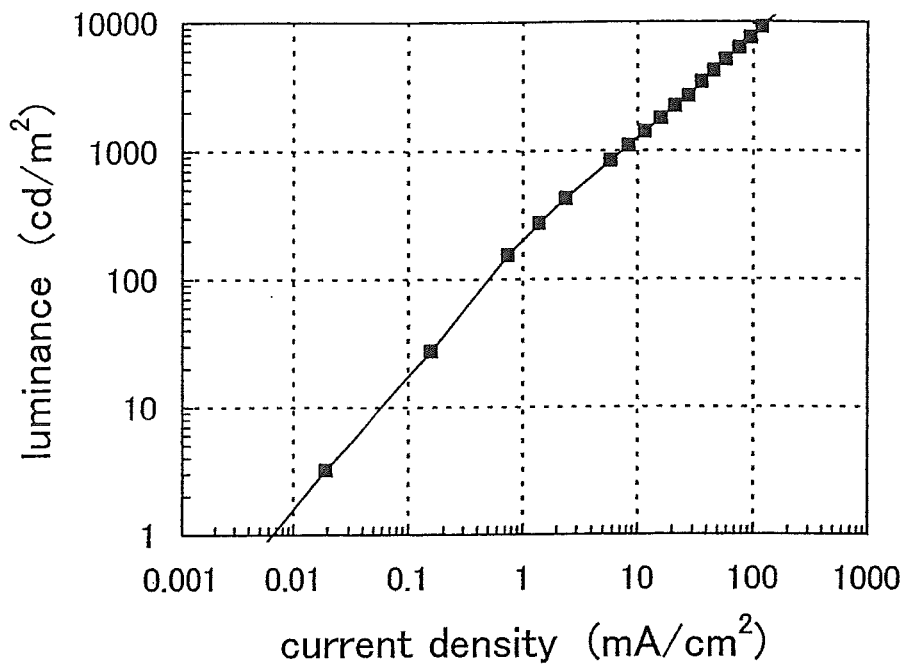
FIG. 13 shows current density-luminance characteristics of a light emitting element manufactured in Example 2.
Figure 14:
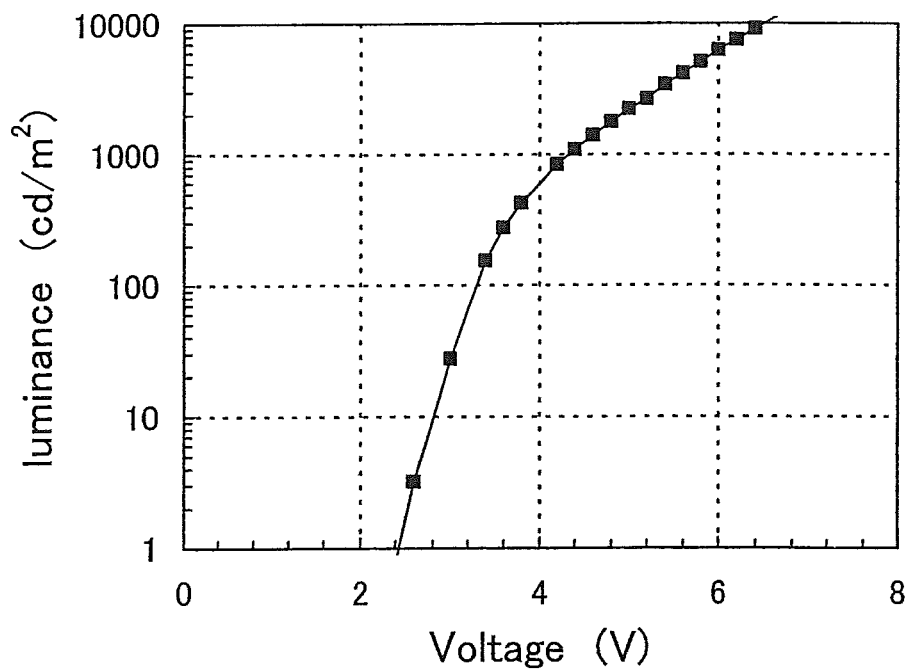
FIG. 14 shows voltage-luminance characteristics of a light emitting element manufactured in Example 2.
Figure 15:
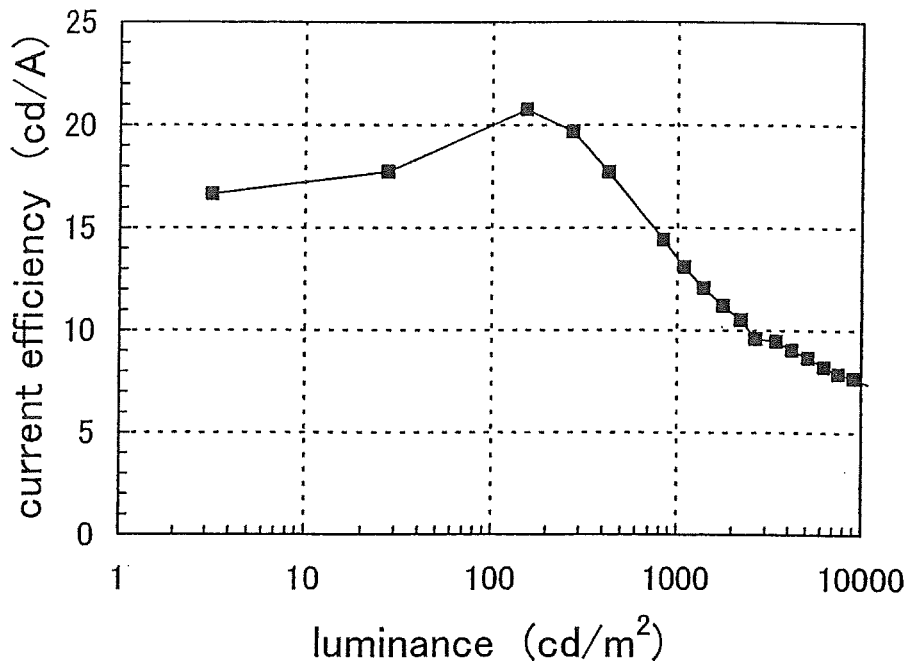
FIG. 15 shows luminance-current efficiency characteristics of a light emitting element manufactured in Example 2.
Figure 16:
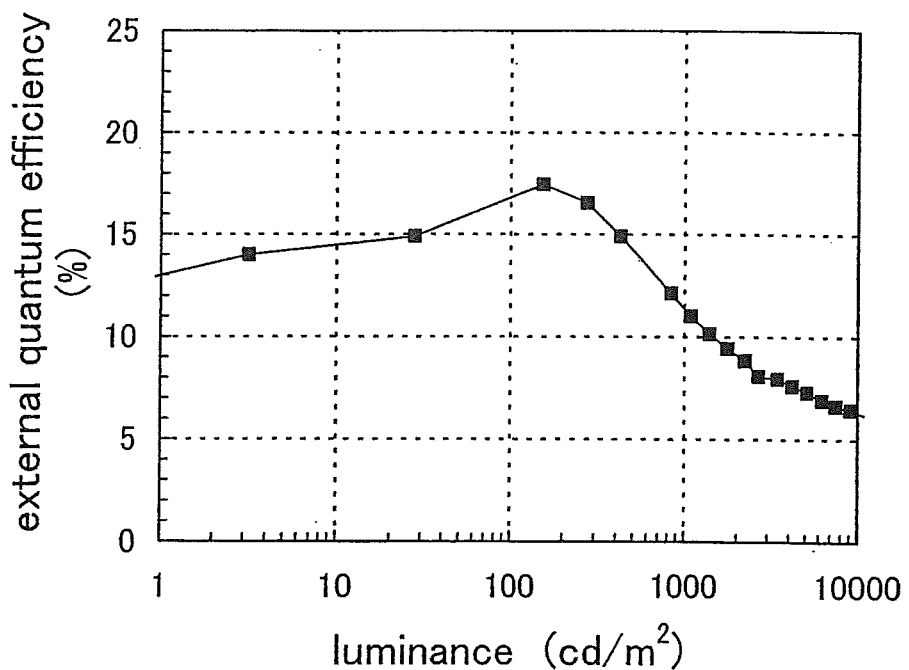
FIG. 16 shows luminance-external quantum efficiency characteristics of a light emitting element manufactured in Example 2.
Figure 17:
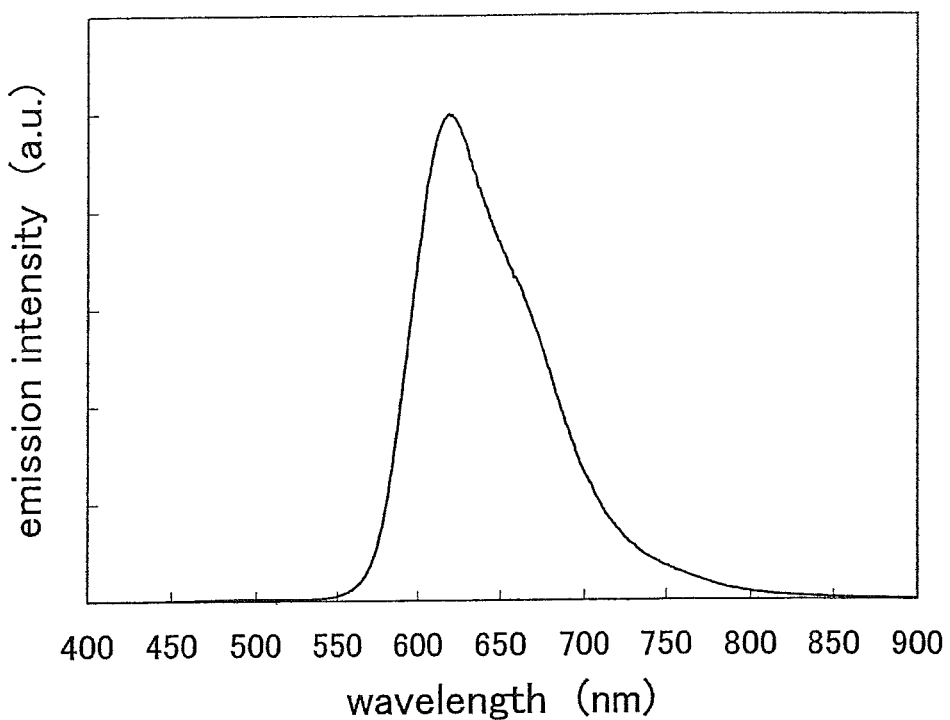
FIG. 17 shows an emission spectrum of a light emitting element manufactured in Example 2.

Current density-luminance characteristics of the light emitting element 1 are shown in FIG. 13. Voltage-luminance characteristics thereof are shown in FIG. 14. Luminance-current efficiency characteristics thereof are shown in FIG. 15. In addition, luminance-external quantum efficiency characteristics are shown in FIG. 16. Also, an emission spectrum upon applying a current of 1 mA is shown in FIG. 17. From FIG. 17, it can be found that light emission of the light emitting element 1 is the light emission of Ir(tppr)$_2$(acac). The CIE chromaticity coordinates of the light emitting element 1 are (x, y)=(0.66, 0.34) when the luminance is 1000 cd/m$^2$, and the light emitting element 1 emits red-color light. Further, as is seen from FIG. 16, the light emitting element 1 exhibits high external quantum efficiency. Therefore, the light emitting element 1 has high light emission efficiency. From FIG. 15, it can be found that the light emitting element 1 has high luminous efficiency. Further, in FIG. 14, the voltage for obtaining a certain level of luminance is low, and this shows that the light emitting element 1 has small power consumption.

An initial luminance was set at 1000 cd/m$^2$, and the light emitting element 1 of this example was driven under a condition of constant current density. After a lapse of 100 hours, the light emitting element 1 kept 97% of the initial luminance, which shows that the light emitting element 1 hardly deteriorated.

EXAMPLE 3

Example 3 will describe a light emitting element of the present invention with reference to FIG. 12.
(Light Emitting Element 2)

First, a film containing indium tin oxide containing silicon oxide was formed over a glass substrate 2101 by sputtering as a first electrode 2102. The film thickness of the first electrode was 110 nm and the area thereof was 2 mm×2 mm.

Then, the substrate provided with the first electrode was fixed on a substrate holder which was provided in a vacuum evaporation apparatus, in such a way that a surface provided with the first electrode should face downward. After that, the air inside the vacuum evaporation apparatus was evacuated to approximately 10$^{-4}$ Pa. Then, a layer including a composite material 2103 including an organic compound and an inorganic compound was formed on the first electrode 2102 by co-evaporation of NPB and molybdenum oxide (VI). The film thickness was 50 nm and the weight ratio between NPB and molybdenum oxide (VI) was adjusted to be 4:1 NPB: molybdenum oxide). Note that the co-evaporation is an evaporation method by which evaporation is carried out simultaneously from a plurality of evaporation sources in one process chamber.

Next, a hole transporting layer 2104 was formed on the layer including the composite material 2103 so as to have a thickness of 10 nm using 4,4'-bis[N-(1-naphthyl)-N-phenylamino]biphenyl (abbreviation: NPB) by evaporation using resistance heating.

Further, a light emitting layer 2105 was formed on the hole transporting layer 2104 to have a thickness of 30 nm by co-evaporation of bis[2-(2-hydroxyphenyl)benzoxazolato] zinc (abbreviation: Zn(PBO)$_2$) and (acetylacetonato)bis(2, 3,5-triphenylpyrazinato)iridium(III) (abbreviation: Ir(tppr)$_2$ (acac)) which is expressed by the structural formula (1). Here, the weight ratio between Zn(PBO)$_2$ and Ir(tppr)$_2$(acac) was adjusted to be 1:0.05 (=Zn(PBO)$_2$: Ir(tppr)$_2$(acac)).

After that, an electron transporting layer 2106 was formed on the light emitting layer 2105 by depositing bis(2-methyl-8-quinolinolato)(4-phenylphenolato)aluminum (abbreviation: BAlq) so as to have a thickness of 10 nm by evaporation using resistance heating.

Further, an electron injecting layer 2107 was formed on the electron transporting layer 2106 so as to have a thickness of 50 nm by co-evaporation of tris(8-quinolinolato)aluminum (abbreviation; Alq) and lithium. The weight ratio between Alq and lithium was adjusted to be 1:0.01 (=Alq: lithium).

Finally, a second electrode 2108 was formed over the electron injecting layer 2107 by depositing aluminum so as to have a thickness of 200 nm by evaporation using resistance heating. Thus, the light emitting element 2 was formed.

Figure 18:
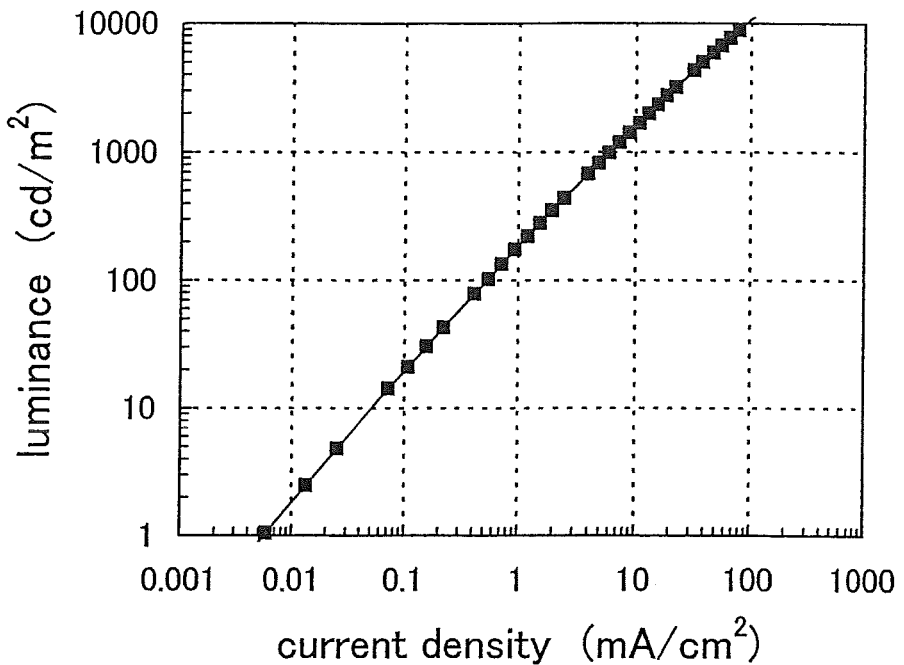
FIG. 18 shows current density-luminance characteristics of a light emitting element manufactured in Example 3.
Figure 19:
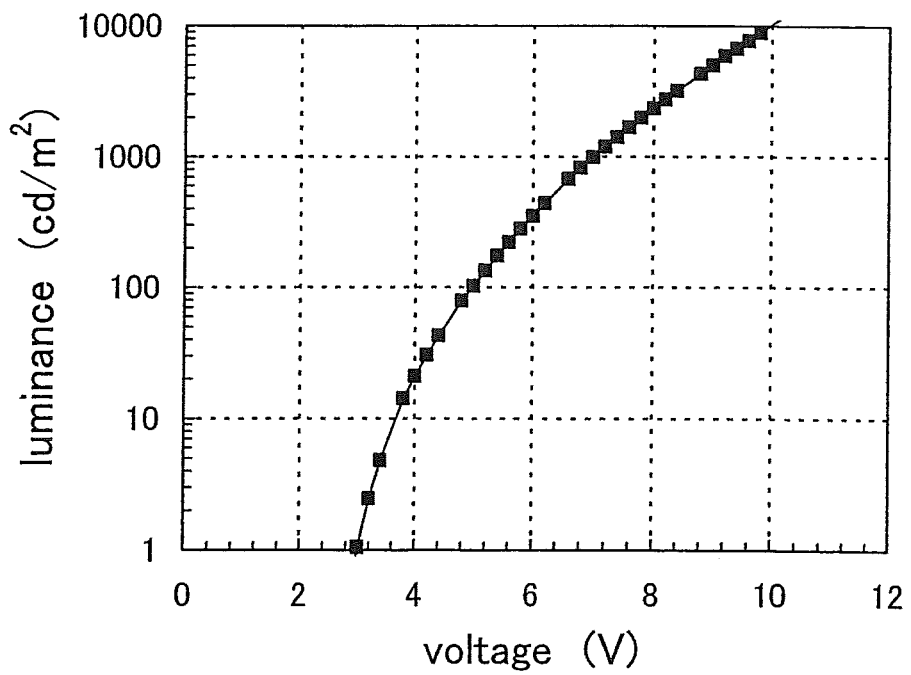
FIG. 19 shows voltage-luminance characteristics of a light emitting element manufactured in Example 3.
Figure 20:
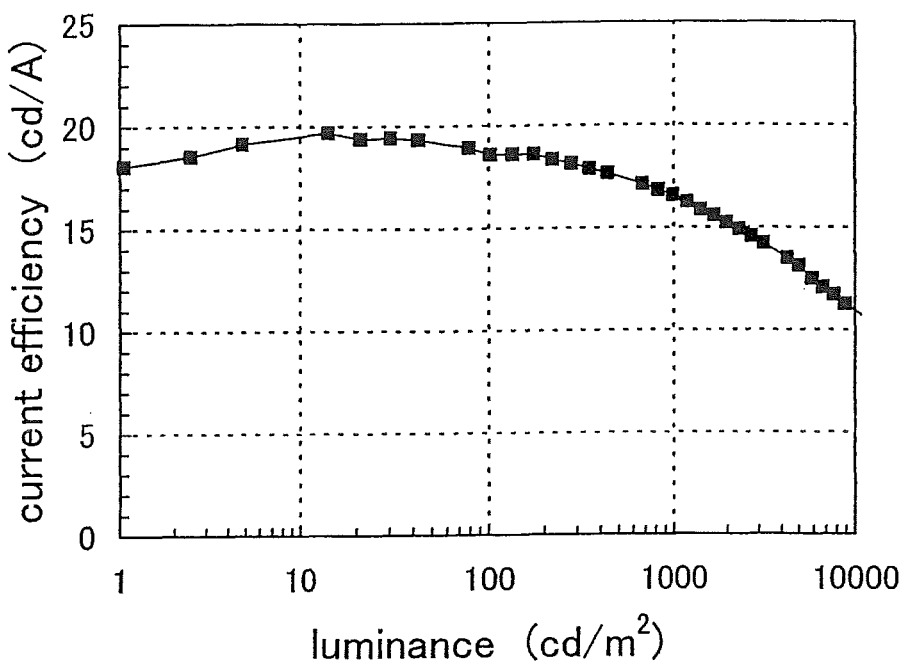
FIG. 20 shows luminance-current efficiency characteristics of a light emitting element manufactured in Example 3.
Figure 21:
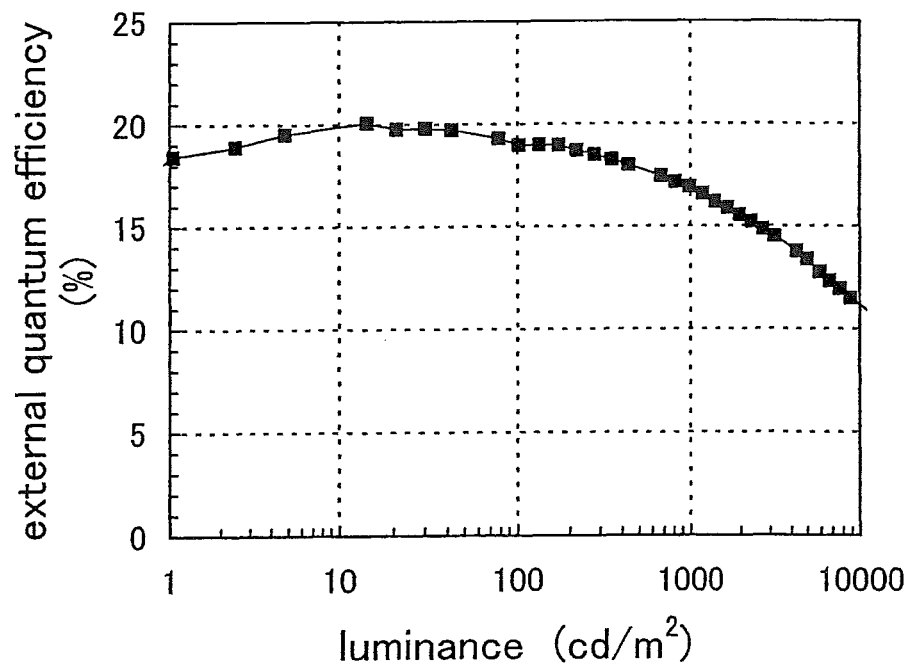
FIG. 21 shows luminance-external quantum efficiency characteristics of a light emitting element manufactured in Example 3.
Figure 22:
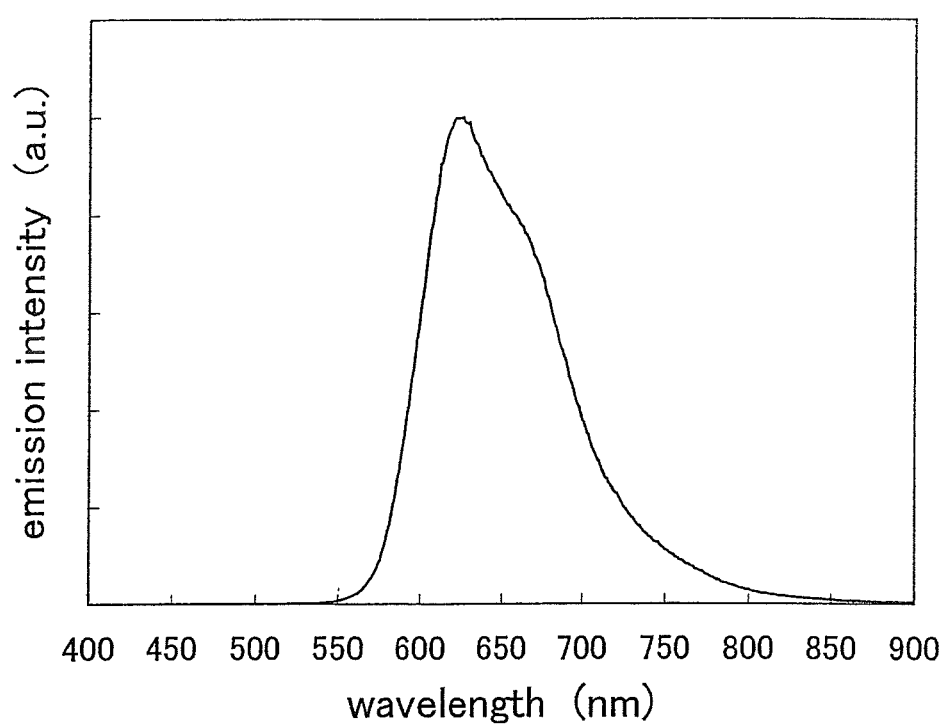
FIG. 22 shows an emission spectrum of a light emitting element manufactured in Example 3.

Current density-luminance characteristics of the light emitting element 2 are shown in FIG. 18. Voltage-luminance characteristics thereof are shown in FIG. 19. Luminance-current efficiency characteristics thereof are shown in FIG. 20. In addition, luminance-external quantum efficiency characteristics are shown in FIG. 21. Also, an emission spectrum upon applying a current of 1 mA is shown in FIG. 22. From FIG. 22, it can be found that light emission of the light emitting element 2 is owing to the light emission of Ir(tppr)$_2$(acac). The CIE chromaticity coordinates of the light emitting element 2 are (x, y)=(0.67, 0.33) when the luminance is 1000 cd/m$^2$, and the light emitting element 2 emits red-color light. Further, as is seen from FIG. 21, the light emitting element 2 exhibits high external quantum efficiency. In particular, it can be found that the light emitting element 2 has further higher external quantum efficiency than the light emitting element 1 formed in Example 1. The light emitting element 2 uses an organometallic complex of the present invention and a zinc complex for the light emitting layer, which is considered as a cause of realizing higher external quantum efficiency.

From FIG. 20, it is found that the light emitting element 2 has high luminous efficiency. Further, it can be found from FIG. 19 that the voltage for obtaining a certain level of luminance is low. This shows that the light emitting element 2 has small power consumption.

EXAMPLE 4

SYNTHETIC EXAMPLE 3

In Synthetic Example 3, a synthetic example of an organometallic complex of the present invention represented by structural formula (20) in Embodiment Mode 1, (acetylacetonato)bis(2,3-diphenyl-5-p-tolylpyrazinato)iridium(III) (abbreviation: [Ir(dppr-MP)$_2$(acac)]), will be specifically described.

Step 1: Synthesis of 2,3-diphenyl-5-p-tolylpyrazine (abbreviation: Hdppr-MP)

First, 0.49 g of magnesium and 3 mL of THF were suspended in a nitrogen atmosphere, and a small amount of 1,2-dibromoethane was added thereto. Then, a mixed solution in which 3.42 g of 4-bromotoluene was dissolved in 20 mL of THF was delivered by drops, and the mixture was stirred for 3 hours under reflux and made into a Grignard reagent. Next, 4.22 g of 2,3-diphenylpyrazine was dissolved in 20 mL of THF, and the Grignard reagent prepared before was delivered thereto by drops, and stirring was conducted for 5 hours under reflux. Water was added to this mixture and an organic layer was extracted with chloroform. The organic layer obtained was dried with magnesium sulfate, and manganese dioxide was added into the dried solution. The mixture was shaken lightly and then filtered, and a solvent of this solution was distilled off. A residue obtained by distillation was dissolved in dichloromethane, and the mixture was added with ethanol and then left, so that a yellow crystal was precipitated. This crystal was filtered out and washed with ethanol; thereby obtaining an objective pyrazine derivative Hdppr-MP (yield of 30%). A synthetic scheme of Step 1 is shown in the following (a-2).

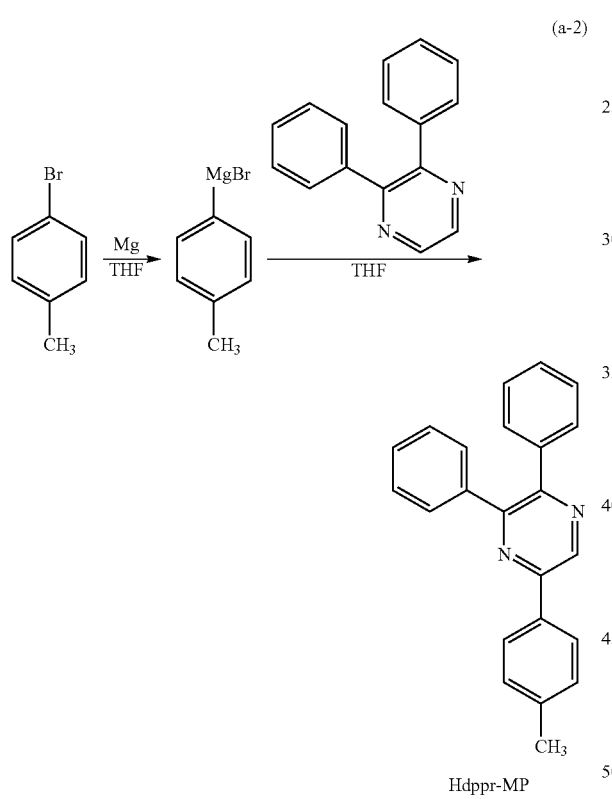

(a-2)

Hdppr-MP

Step 2: Synthesis of di-μ-chloro-bis[bis(2,3-diphenyl-5-p-tolylpyrazinato)iridium (III)] (abbreviation: [Ir(dppr-MP)$_2$Cl]$_2$)

Next, 24 mL of 2-ethoxyethanol, 8 mL of water, 0.64 g of the pyrazine derivative Hdppr-MP obtained in the above Step 1, and 0.30 g of iridium chloride hydrate (IrCl$_3$·H$_2$O) (produced by Sigma-Aldrich Corp.) were put in an eggplant-type flask with a reflux pipe, and the inside air of the flask was substituted by argon. Then, a reaction was carried out by irradiation with microwave (2.45 GHz, 150 W) for 1 hour. An orange powder precipitated from the reacted solution was filtered and washed with ethanol; thereby obtaining a dinuclear complex [Ir(dppr-MP)$_2$Cl]$_2$ (yield of 58%). The irradiation of microwave was conducted using a microwave synthesis system (Discovery, manufactured by CEM Corporation). A synthetic scheme of Step 2 is shown in the following (b-2).

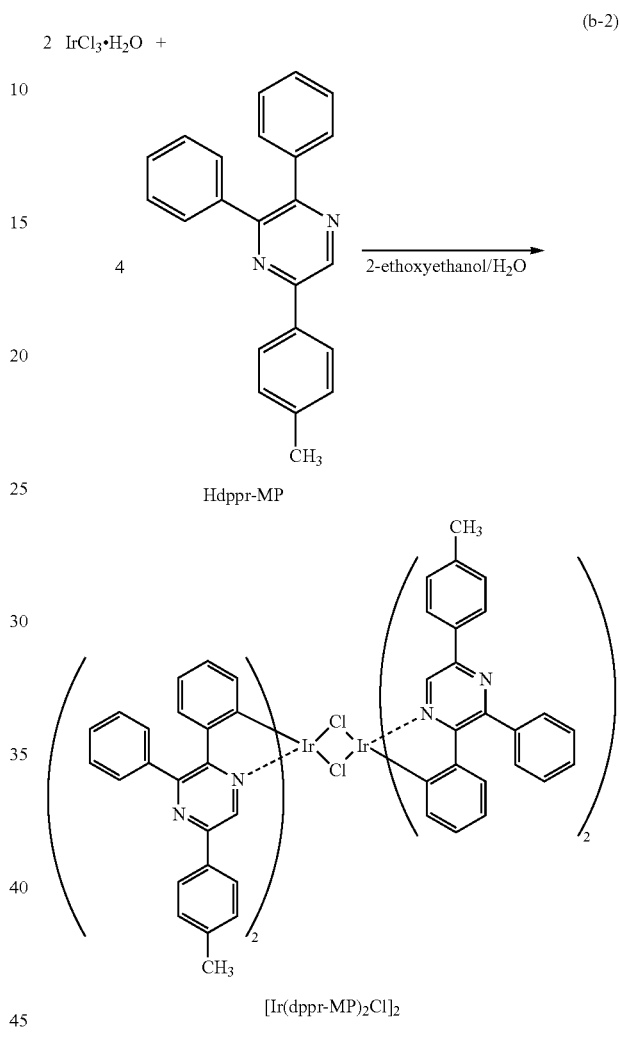

(b-2)

Step 3: Synthesis of (acetylacetonato)bis(2,3-diphenyl-5-p-tolylpyrazinato)iridium(III) (abbreviation: [Ir(dppr-MP)$_2$(acac)]

Next, 20 mL of 2-ethoxyethanol, 0.50 g of the dinuclear complex [Ir(dppr-MP)$_2$Cl]$_2$ obtained in the above Step 2, 0.09 mL of acetylacetone, and 0.31 g of sodium carbonate were put in an eggplant-type flask with a reflux pipe, and the inside air of the flask was substituted by argon. Then, a reaction was carried out by irradiation with microwave (2.45 GHz, 150 W) for 30 minutes. The reacted solution was filtered, and a filtrate obtained was condensed and dried. A residue obtained was recrystallized with ethanol, and a red powder obtained was washed with ethanol and then ether; thereby obtaining an organometallic complex of the present invention [Ir(dppr-MP)$_2$(acac)] (yield of 96%). A synthetic scheme of Step 3 is shown in the following (c-2).

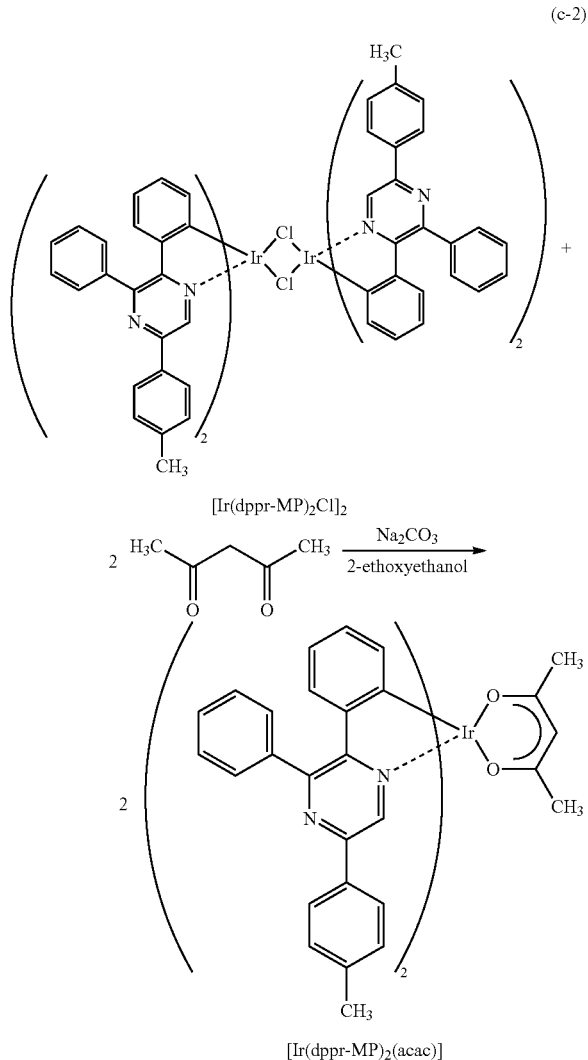

[Ir(dppr-MP)₂Cl]₂

[Ir(dppr-MP)₂(acac)]

Figure 24A:
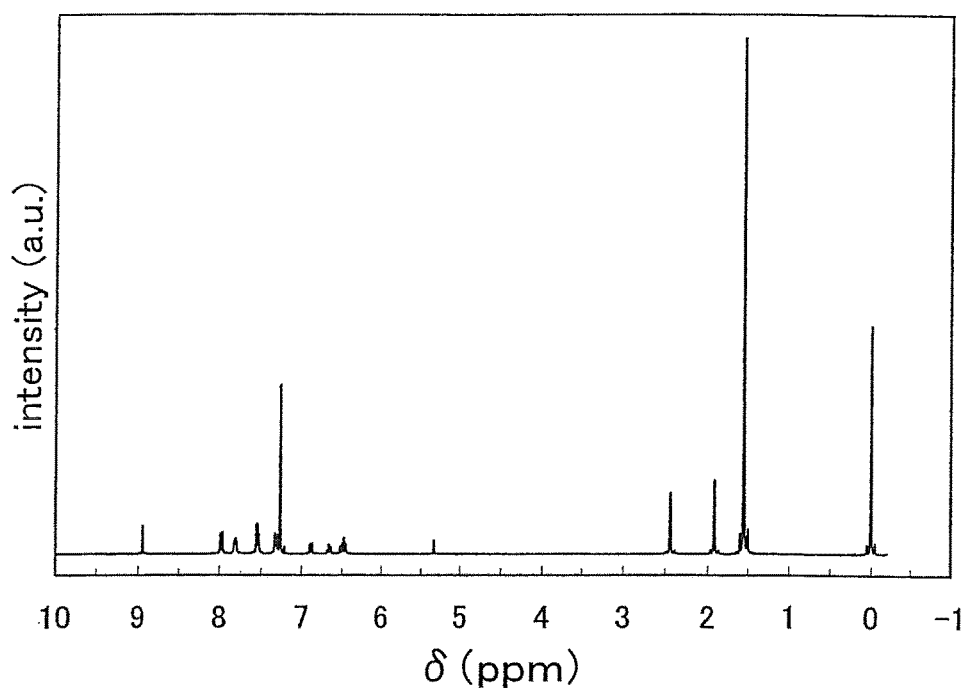
FIGS. 24A and 24B show a $^1$H-NMR chart of (acetylacetonato)bis(2,3-diphenyl-5-p-tolylpyrazinato)iridium(III)
Figure 24B:
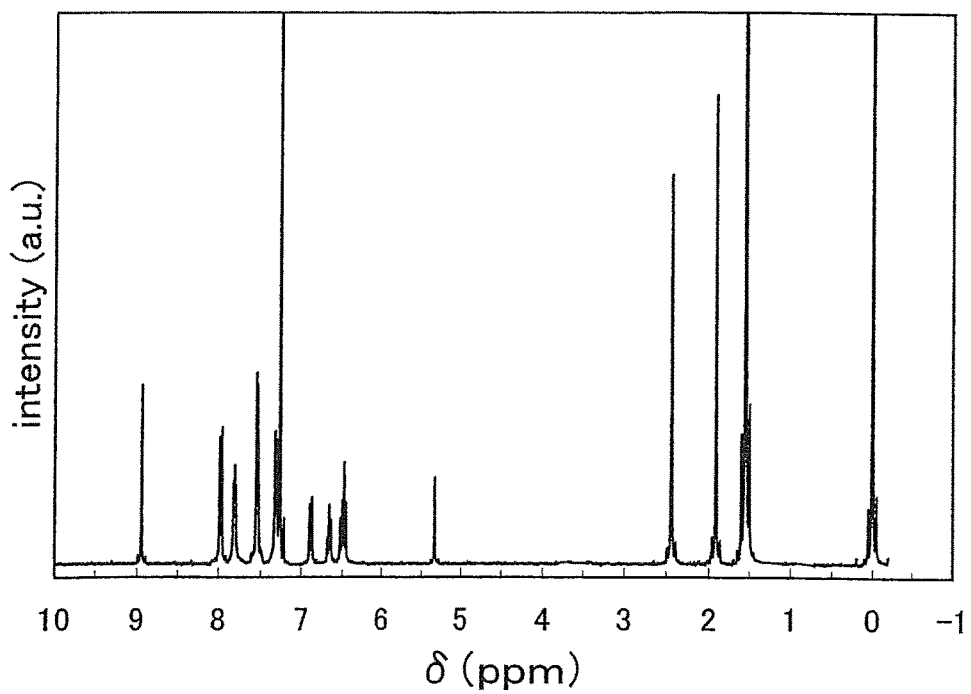

An analysis result of the red powder obtained in Step 3 by nuclear magnetic resonance spectrometry ($^1$H-NMR) is shown below. A $^1$H-NMR chart is shown in FIGS. 24A and 24B. From FIGS. 24A and 24B, it was found that the organometallic complex [Ir(dppr-MP)₂(acac)] of the present invention represented by the above structural formula (20) was obtained in Synthetic Example 3.

$^1$H-NMR. δ (CDCl₃): 1.91 (s, 6H), 2.44 (s, 6H), 5.33 (s, 1H), 6.47 (m, 4H), 6.66 (t, 2H), 6.89 (d, 2H), 7.33 (m, 5H), 7.54 (m, 7H), 7.80 (m, 4H), 7.79 (d, 4H), 8.94 (s, 2H).

A decomposition temperature of the obtained organometallic complex [Ir(dppr-MP)₂(acac)] of the present invention was measured using a high-vacuum differential type differential thermal analyzer/thermogravimetry-differential thermal analyzer (manufactured by Bruker AXS K.K., TG-DTA2410SA). The rising temperature rate was set at 10° C./min. When the temperature was raised at a normal pressure, 5% of gravity reduction was seen at a temperature of 338° C., and it was found that the organometallic complex exhibited excellent heat resistance.

Figure 25:
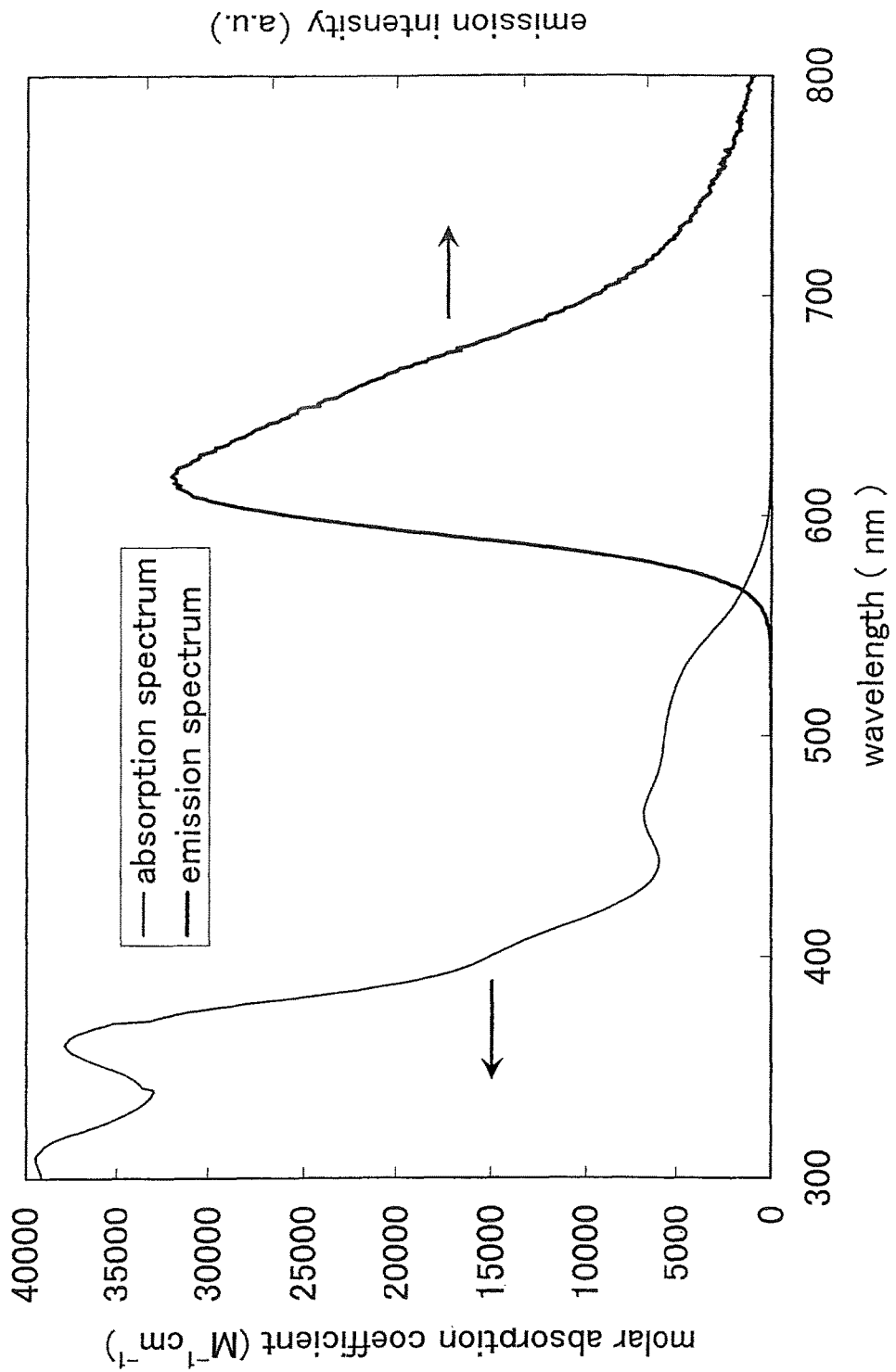
FIG. 25 shows an absorption spectrum and an emission spectrum of (acetylacetonato)bis(2,3-diphenyl-5-p-tolylpyrazinato)iridium(III)

Next, an absorption spectrum of [Ir(dppr-MP)₂(acac)] was measured with the use of an ultraviolet-visible light spectrophotometer (manufactured by Japan Spectroscopy Corporation, V550 type). The measurement was conducted by using a dichloromethane solution (0.10 mmol/L) at a room temperature. In addition, an emission spectrum of [Ir(dppr-MP)₂(acac)] was measured with the use of a fluorescence spectrophotometer (manufactured by Hamamatsu Photonics Corporation, FS920). The measurement was conducted by using a degassed dichloromethane solution (0.35 mmol/L) at a room temperature. FIG. 25 shows the measurement results. The horizontal axis indicates a wavelength and the vertical axis indicates a molar absorption coefficient and emission intensity.

As shown in FIG. 25, the organometallic complex [Ir(dppr-MP)₂(acac)] of the present invention has a peak of emission spectrum at 620 nm, and red light was observed from the solution.

EXAMPLE 5

SYNTHETIC EXAMPLE 4

In Synthetic Example 4, a synthetic example of an organometallic complex of the present invention represented by structural formula (27) in Embodiment Mode 1, (acetylacetonato)bis(5-phenyl-2,3-di-p-tolylpyrazinato)iridium(III) (abbreviation: [Ir(Mdppr-P)₂(acac)]), will be specifically described.

Step 1: Synthesis of 2,3-di-p-tolylpyrazine

First, 25.52 g of 4,4'-dimethylbenzyl and 6.44 g of anhydrous ethylenediamine were dissolved in a solvent of dehydrated ethanol (300 mL) in a nitrogen atmosphere and reacted for 12.5 hours by refluxing. 34.71 g of iron oxide (III) was added into this reacted solution, and a reaction was carried out by slowly stirring the solution while being heated at 70° C. or lower for 2.5 hours. Water was added into this mixture and an organic layer was extracted with dichloromethane. The organic layer obtained was dried with magnesium sulfate. After the drying, filtration was conducted and a solvent of this solution was distilled off. A residue obtained by the distillation was purified by silica gel column chromatography which uses dichloromethane as a developing solvent; thereby obtaining an intermediate, 2,3-di-p-tolylpyrazine (orange powder, yield of 31%).

Step 2: Synthesis of 5-phenyl-2,3-di-p-tolylpyrazine (abbreviation: HMdppr-P)

Next, in a nitrogen atmosphere, 6.48 mL of a dibutyl ether solution containing phenyl lithium (produced by Wako Pure Chemical Industries, Ltd., 2.1 mol/L) and 80 mL of diethylether were mixed. While the mixed solution was being cooled with ice, 3.22 g of 2,3-di-p-tolylpyrazine which was an intermediate obtained in the above Step 1 was added thereto and stirred at a room temperature for 24 hours. Water was added into this mixture, and an organic layer was extracted with dichloromethane. The organic layer obtained was washed with water and dried with magnesium sulfate. The solution after drying was added with activated manganese dioxide excessively and filtration was conducted. After a solvent of this solution was distilled off, a residue obtained by the distillation was purified by silica gel column chromatography which uses dichloromethane as a developing solvent; thereby obtaining an objective pyrazine derivative HMdppr-P (orange powder, yield of 22%). A synthetic scheme of Step 1 and Step 2 is shown in the following (a-3).

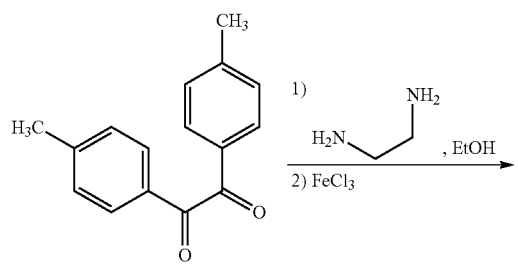

(a-3)

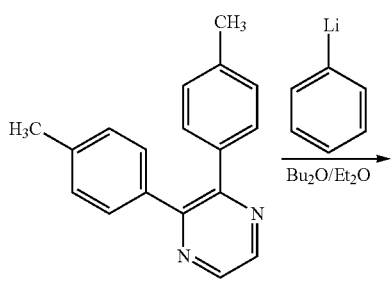

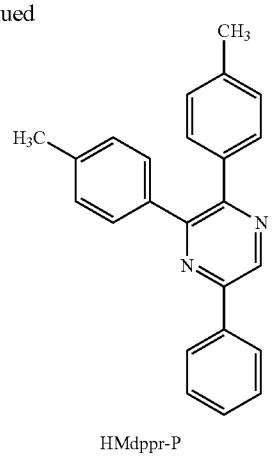

HMdppr-P

Step 3: Synthesis of di-µ-chloro-bis[bis(5-phenyl-2,3-di-p-tolylpyrazinato)iridium(III)] (abbreviation: [Ir(Mdppr-P)$_2$Cl]$_2$)

18 mL of 2-ethoxyethanol, 6 mL of water, 0.82 g of the pyrazine derivative HMdppr-P obtained in the above Step 2, and 0.36 g of iridium chloride hydrate (IrCl$_3$·H$_2$O) (produced by Sigma-Aldrich Corp.) were put in an eggplant-type flask with a reflux pipe, and the inside air of the flask was substituted by argon. Then, a reaction was carried out by irradiation with microwave (2.45 GHz, 200 W) for 1 hour. An orange powder precipitated from the reacted solution was filtered and washed with ethanol; thereby obtaining a dinuclear complex [Ir(Mdppr-P)$_2$Cl]$_2$ (yield of 82%). The irradiation of microwave was conducted using a microwave synthesis system (Discovery, manufactured by CEM Corporation). A synthetic scheme of Step 3 is shown in the following (b-3).

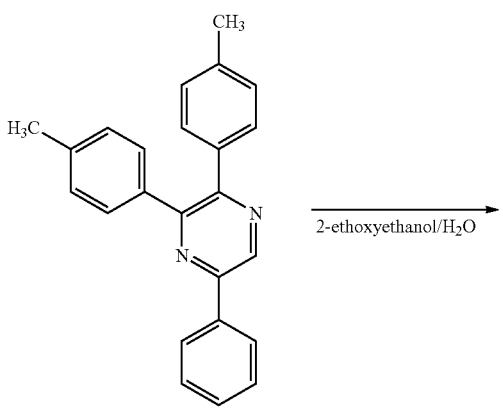

(b-3)

HMdppr-P

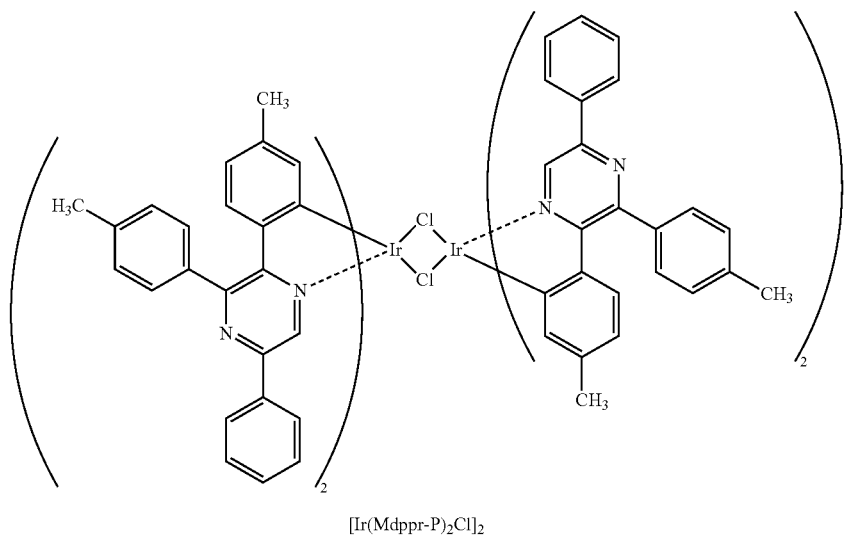

[Ir(Mdppr-P)₂Cl]₂

Step 4: Synthesis of (acetylacetonato)bis(5-phenyl-2,3-di-p-tolylpyrazinato)iridium(III) (abbreviation: [Ir(Mdppr-P)₂(acac)])

Next, 20 mL of 2-ethoxyethanol, 0.44 g of the dinuclear complex [Ir(Mdppr-P)₂Cl]₂ obtained in the above Step 3, 0.08 mL of acetylacetone, and 0.25 g of sodium carbonate were put in an eggplant-type flask with a reflux pipe, and the inside air of the flask was substituted by argon. Then, a reaction was carried out by irradiation with microwave (2.45 GHz, 200 W) for 30 minutes. The reacted solution was filtered, and then a filtrate obtained was condensed and dried. A residue obtained was recrystallized with ethanol, and a red powder obtained was washed with ethanol and then ether; thereby obtaining an organometallic complex of the present invention, [Ir(Mdppr-P)₂(acac)] (yield of 31%). A synthetic scheme of Step 4 is shown in the following (c-3).

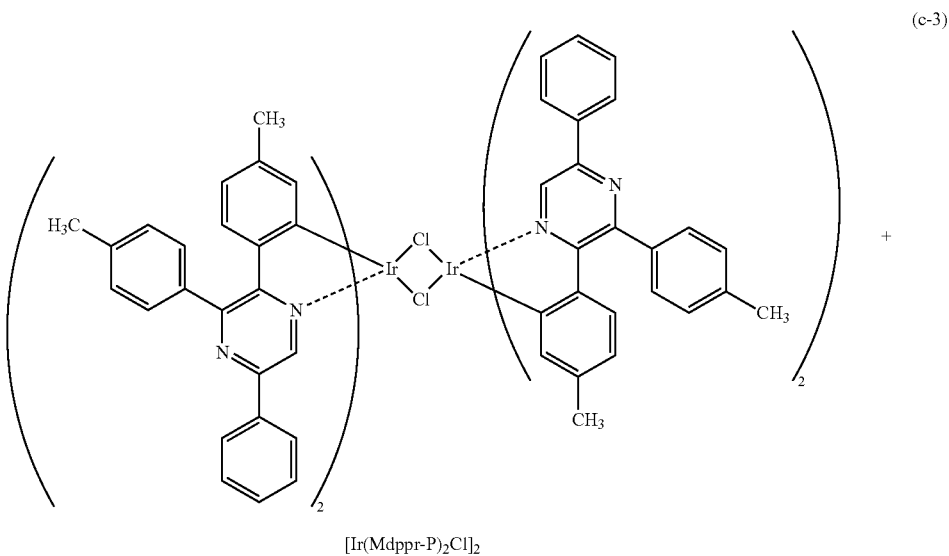

(c-3)

[Ir(Mdppr-P)₂Cl]₂

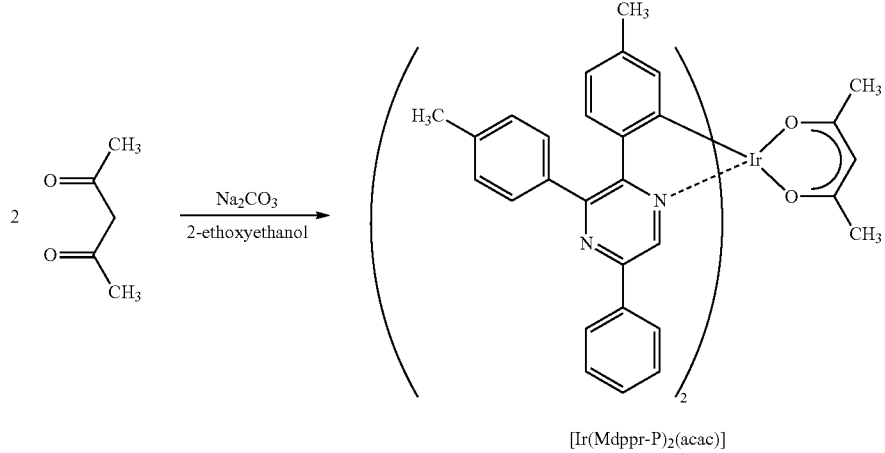

[Ir(Mdppr-P)₂(acac)]

Figure 26A:
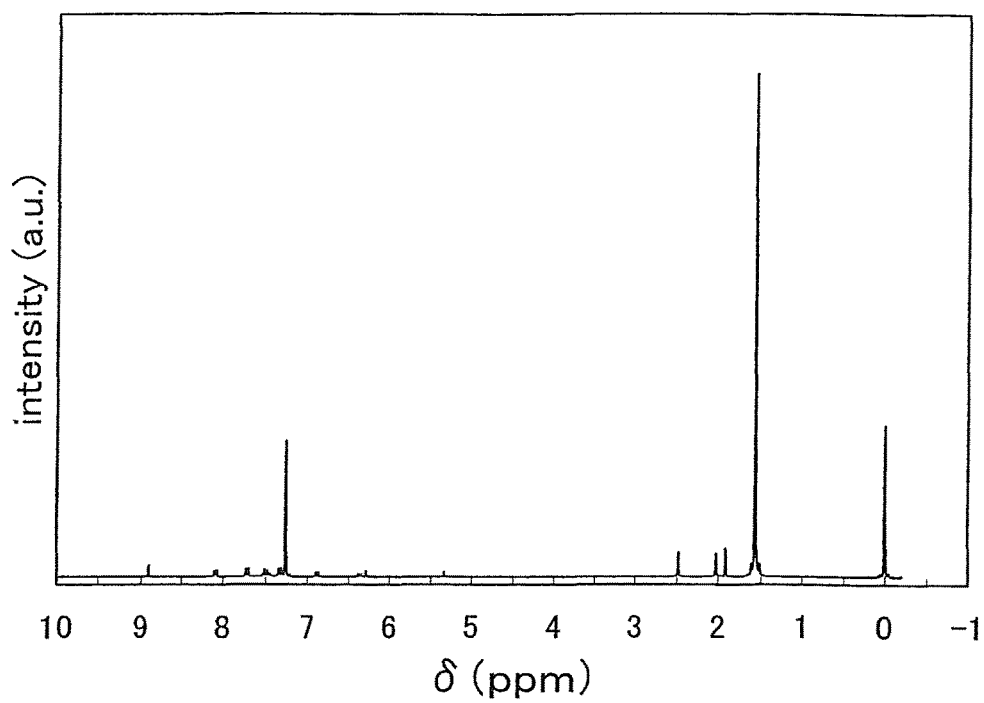
FIGS. 26A and 26B show a $^1$H-NMR chart (acetylacetonato)bis(5-phenyl-2,3-di-p-tolylpyrazinato)iridium(III)
Figure 26B:
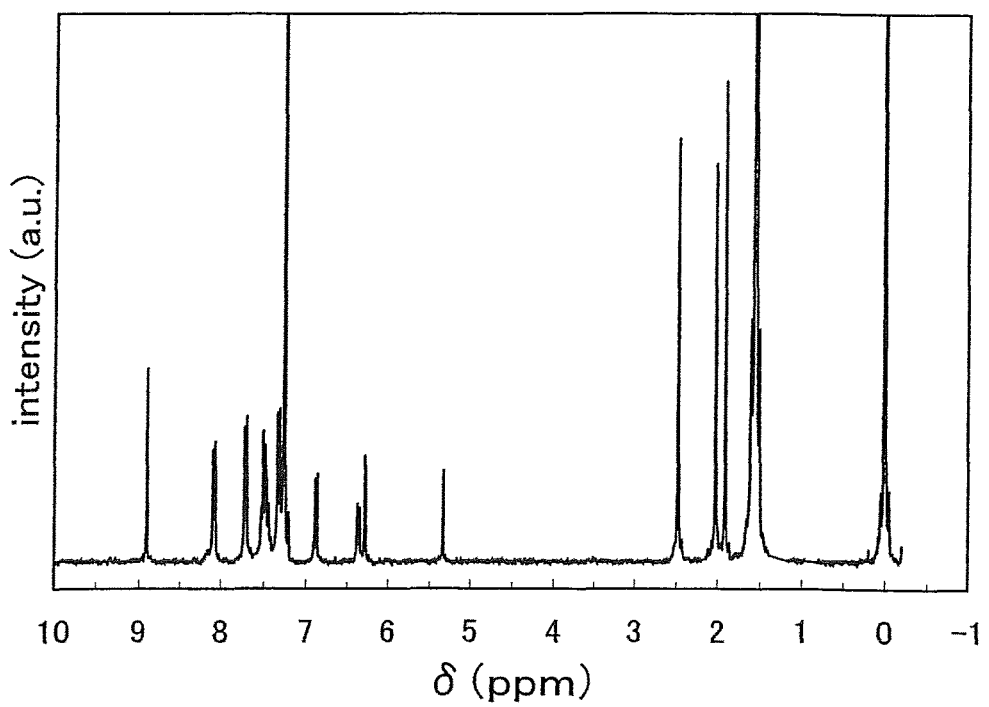

An analysis result of the red powder obtained in Step 4 by nuclear magnetic resonance spectrometry (¹H-NMR) is shown below. A ¹H-NMR chart is shown in FIGS. 26A and 26B. From FIGS. 26A and 26B, it was found that the organometallic complex [Ir(Mdppr-P)₂(acac)] of the present invention represented by the above structural formula (27) was obtained in Synthetic Example 4.

¹H-NMR. δ (CDCl₃): 1.91 (s, 6H), 2.02 (s, 6H), 2.48 (s, 6H), 5.33 (s, 1H), 6.28 (s, 2H), 6.36 (d, 2H), 6.88 (d, 2H), 7.33 (m, 4H), 7.51 (m, 6H), 7.72 (d, 4H), 8.08 (d, 4H), 8.91 (s, 2H).

A decomposition temperature of the obtained organometallic complex [Ir(Mdppr-P)₂(acac)] of the present invention was measured using a high-vacuum differential type differential thermal analyzer/thermogravimetry-differential thermal analyzer (manufactured by Bruker AXS K.K., TG-DTA2410SA). The rising temperature rate was set at 10° C./min. When the temperature was raised at a no' mal pressure, 5% of gravity reduction was seen at a temperature of 342° C., and it was found that the organometallic complex exhibited excellent heat resistance.

Figure 27:
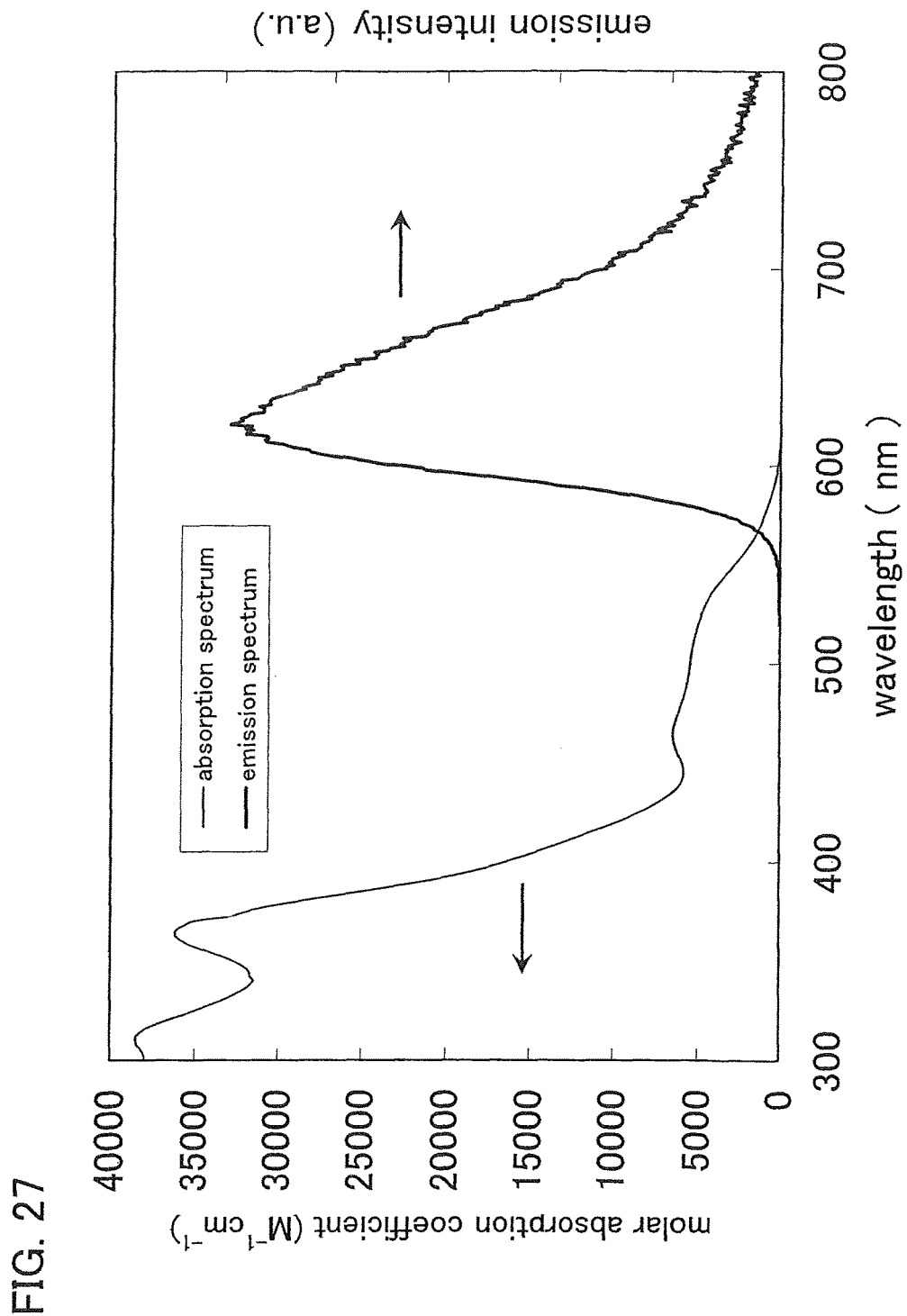
FIG. 27 shows an absorption spectrum and an emission spectrum of (acetylacetonato)bis(5-phenyl-2,3-di-p-tolylpyrazinato)iridium(III)

Next, an absorption spectrum of [Ir(Mdppr-P)₂(acac)] was measured with the use of an ultraviolet-visible light spectrophotometer (manufactured by Japan Spectroscopy Corporation, V550 type). The measurement was conducted by using a dichloromethane solution (0.096 mmol/L) at a room temperature. In addition, an emission spectrum of [Ir(Mdppr-P)₂(acac)] was measured with the use of a fluorescence spectrophotometer (manufactured by Hamamatsu Photonics Corporation, FS920). The measurement was conducted by using a degassed dichloromethane solution (0.34 mmol/L) at a room temperature. FIG. 27 shows the measurement results. The horizontal axis indicates a wavelength and the vertical axis indicates a molar absorption coefficient and emission intensity.

As shown in FIG. 27, the organometallic complex [Ir(Mdppr-P)₂(acac)] of the present invention has a peak of emission spectrum at 620 nm, and red light was observed from the solution.

EXAMPLE 6

SYNTHETIC EXAMPLE 5

In Synthetic Example 5, a synthetic example of an organometallic complex of the present invention represented by structural formula (3) in Embodiment Mode 1, bis(2,3,5-tolylpyrazinato)(picolinato)iridium(III) (abbreviation: [Ir(tppr)₂(pic)]), will be specifically described.

Synthesis of bis(2,3,5-triphenylpyrazinato)(picolinato)iridium(III) (abbreviation; [Ir(tppr)₂(pic)]

25 mL of dichloromethane, 0.84 g of the dinuclear complex [Ir(tppr)₂Cl]₂ obtained in Step 2 of Synthetic Example 1, and 0.49 g of picolinic acid were put in an eggplant-type flask with a reflux pipe, and the inside air of the flask was substituted by argon. Then, a reaction was carried out by irradiation with microwave (2.45 GHz, 100 W) for 30 minutes. The reacted solution was filtered, and a filtrate obtained was condensed and dried. A residue obtained was recrystallized with a mixed solvent of methanol and dichloromethane; thereby obtaining an organometallic complex of the present invention, [Ir(tppr)₂(pic)] (yield of 84%, red-orange powder). The irradiation of microwave was conducted using a microwave synthesis system (Discovery, manufactured by CEM Corporation). A synthetic scheme of this complex is shown in the following (c-4).

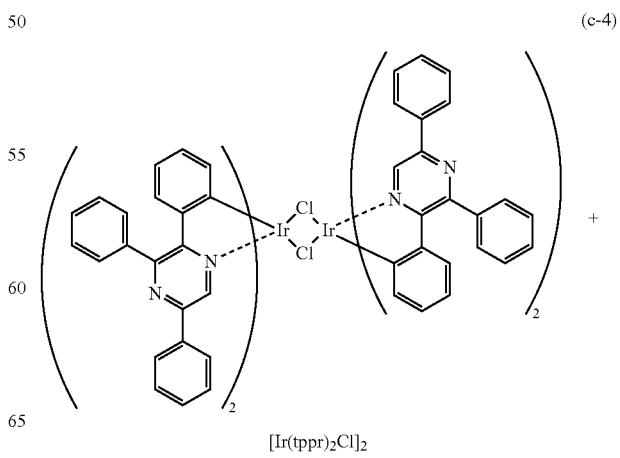

(c-4)

[Ir(tppr)₂Cl]₂

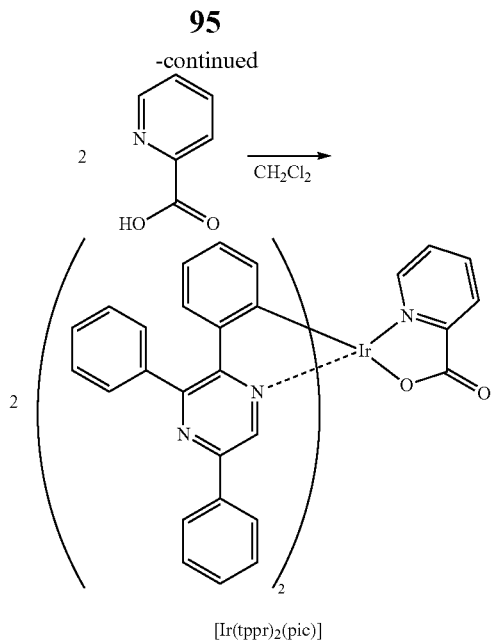

[Ir(tppr)₂(pic)]

Figure 28A:
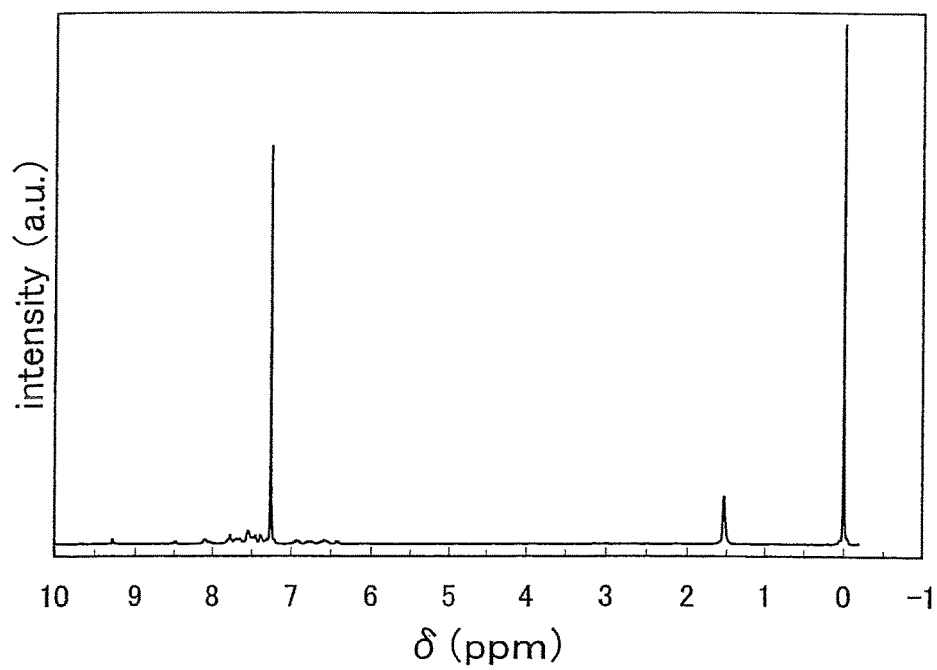
FIGS. 28A and 28B show a $^1$H-NMR chart of bis(2,3,5-triphenylpyrazinato)(picolinato)iridium(III)
Figure 28B:
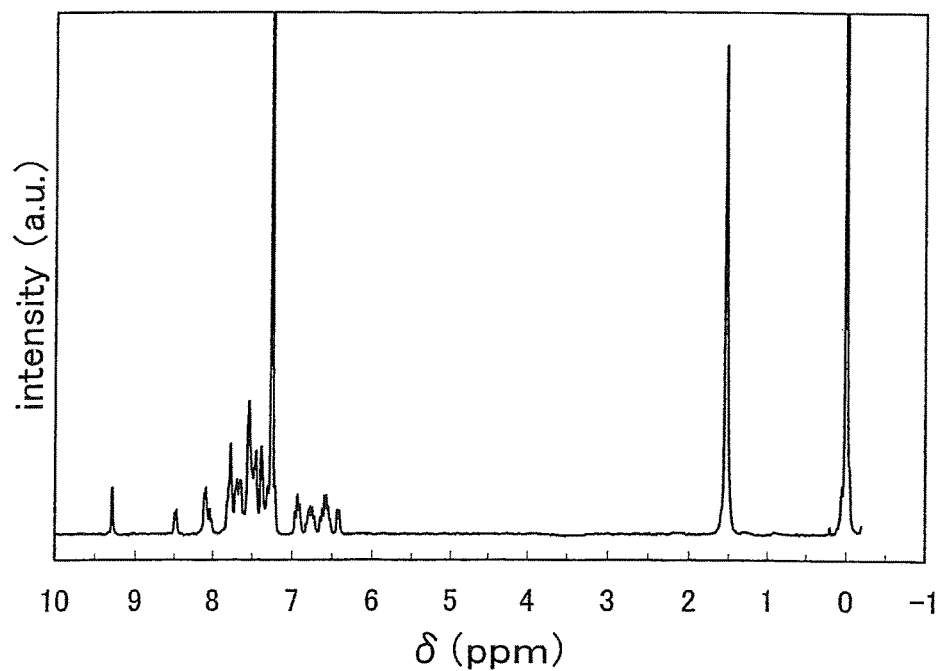

An analysis result of the red-orange powder obtained by the above step by nuclear magnetic resonance spectrometry (¹H-NMR) is shown below. A ¹H-NMR chart is shown in FIGS. 28A and 28B. From FIGS. 28A and 28B, it was found that the organometallic complex [Ir(tppr)₂(pic)] of the present invention represented by the above structural formula (3) was obtained in Synthetic Example 5.

¹H-NMR. δ (CDCl₃): 6.42 (d, 1H), 6.58 (m, 3H), 6.77 (m, 2H), 6.93 (m, 2H), 7.39 (m, 3H), 7.45-7.56 (m, 8H), 7.67 (m, 4H), 7.77 (m, 4H), 8.09 (m, 3H), 8.48 (d, 1H), 8.28 (s, 1H).

A decomposition temperature of the obtained organometallic complex [Ir(tppr)₂(pic)] of the present invention was measured using a high-vacuum differential type differential thermal analyzer/thermogravimetry-differential thermal analyzer (manufactured by Bruker AXS K.K., TG-DTA2410SA). The rising temperature rate was set at 10° C./min. When the temperature was raised at a normal pressure, 5% of gravity reduction was seen at a temperature of 368° C., and it was found that the organometallic complex exhibited excellent heat resistance.

Figure 29:
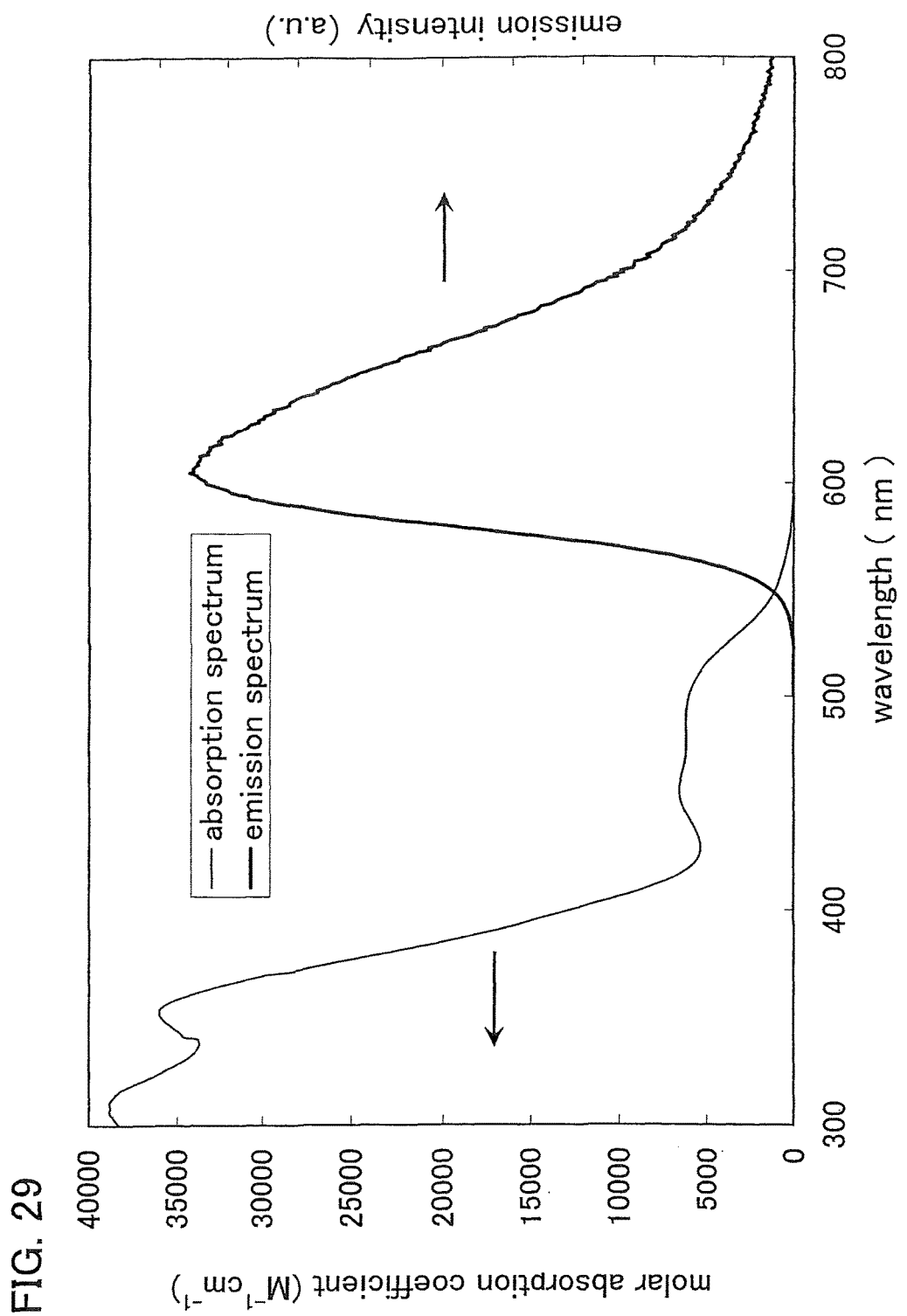
FIG. 29 shows an absorption spectrum and an emission spectrum of bis(2,3,5-triphenylpyrazinato)(picolinato)iridium(III)

Next, an absorption spectrum of [Ir(tppr)₂(pic)] was measured with the use of an ultraviolet-visible light spectrophotometer (manufactured by Japan Spectroscopy Corporation, V550 type). The measurement was conducted by using a dichloromethane solution (0.10 mmol/L) at a room temperature. In addition, an emission spectrum of [Ir(tppr)₂(pic)] was measured with the use of a fluorescence spectrophotometer (manufactured by Hamamatsu Photonics Corporation, FS920). The measurement was conducted by using a degassed dichloromethane solution (0.35 mmol/L) at a room temperature. FIG. 29 shows the measurement results. The horizontal axis indicates a wavelength and the vertical axis indicates a molar absorption coefficient and emission intensity.

As shown in FIG. 29, the organometallic complex [Ir(tppr)₂(pic)] of the present invention has a peak of emission spectrum at 606 nm, and orange light was observed from the solution.

EXAMPLE 7

Synthetic Example 6

In Synthetic Example 6, a synthetic example of an organometallic complex of the present invention represented by structural formula (34) in Embodiment Mode 1, (acethylacetonato)bis(3-methyl-2,5-diphenylpyrazinato)iridium(III) (abbreviation: [Ir(mppr-P)₂(acac)]), will be specifically described.

Step 1: Synthesis of 3-methyl-2,5-diphenylpyrazine (abbreviation: Hmppr-P)

In a nitrogen atmosphere, 10 mL of a dibutyl ether solution containing phenyl lithium (produced by Wako Pure Chemical Industries, Ltd., 2.1 mol/L) and 120 mL of diethylether were mixed. While the mixed solution was being cooled with ice, 2.87 g of 2-methyl-3-phenylpyrazine was added thereto and stirred at a room temperature for 24 hours. Water was added into this mixture, and an organic layer was extracted with ethyl acetate. The organic layer obtained was dried with magnesium sulfate. The solution after drying was added with activated manganese dioxide excessively and filtration was conducted. A solvent of the obtained filtrate was distilled off, so that a residue was obtained. This residue was purified by silica gel column chromatography which uses dichloromethane as a developing solvent; thereby obtaining an objective pyrazine derivative Hmppr-P (orange oily substance, yield of 12%). A synthetic scheme of Step 1 is shown in the following (a-5).

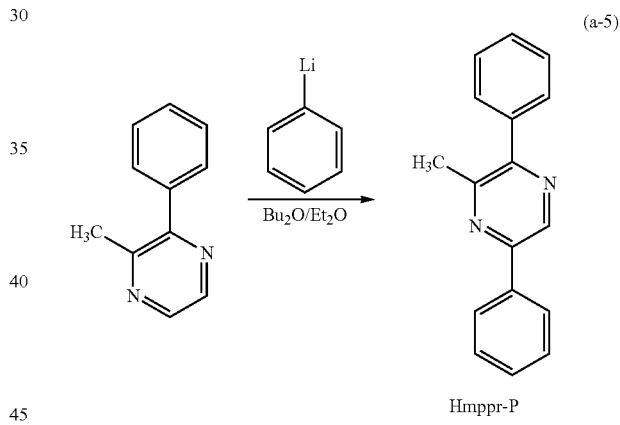

Step 2: Synthesis of di-μ-chloro-bis[bis(3-methyl-2,5-diphenylpyrazinato)iridium(III)] (abbreviation: [Ir(mppr-P)₂Cl]₂)

Next, 21 mL of 2-ethoxyethanol, 7 mL of water, 0.49 g of the pyrazine derivative Hmppr-P obtained in the above Step 1, and 0.30 g of iridium chloride hydrate (IrCl₃·H₂O) (produced by Sigma-Aldrich Corp.) were put in an eggplant-type flask with a reflux pipe, and the inside air of the flask was substituted by argon. Then, a reaction was carried out by irradiation with microwave (2.45 GHz, 150 W) for 30 minutes. An orange powder precipitated from the reacted solution was filtered and washed with ethanol; thereby obtaining a dinuclear complex [Ir(mppr-P)₂Cl]₂ (yield of 10%). The irradiation of microwave was conducted using a microwave synthesis system (Discovery, manufactured by CEM Corporation). A synthetic scheme of Step 2 is shown in the following (b-5).

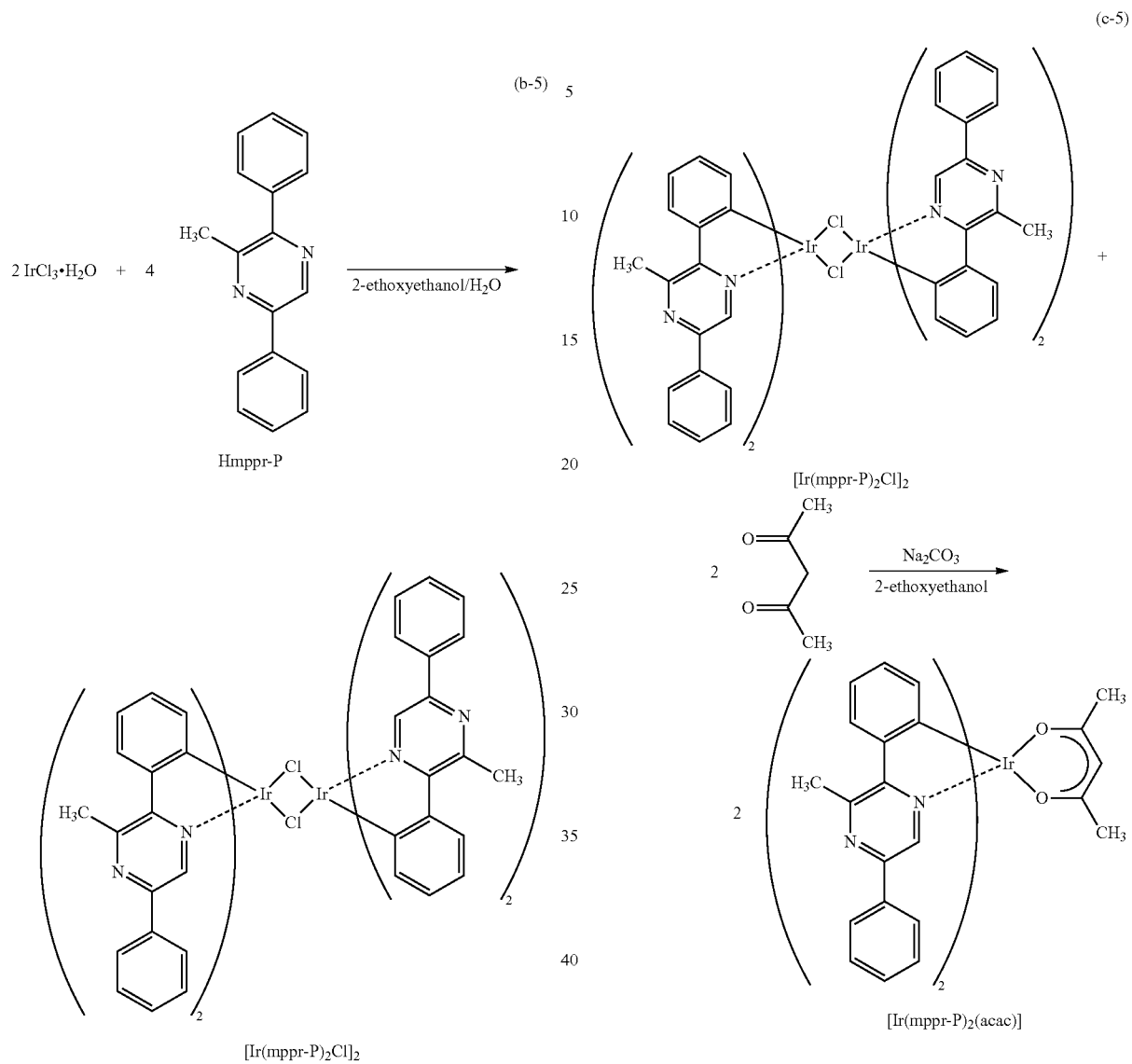

Step 3: synthesis of (acetylacetonato)bis(3-methyl-2,5-diphenylpyrazinato)iridium(III) (abbreviation: [Ir(mppr-P)₂(acac)])

Next, 10 mL of 2-ethoxyethanol, 0.14 g of the dinuclear complex [Ir(mppr-P)₂Cl]₂ obtained in the above Step 2, 0.03 mL of acetylacetone, and 0.10 g of sodium carbonate were put in an eggplant-type flask with a reflux pipe, and the inside air of the flask was substituted by argon. Then, a reaction was carried out by irradiation with microwave (2.45 GHz, 100 W) for 30 minutes. A red-orange powder precipitated from the reacted solution was filtered, and washed with water, ethanol, and then ether; thereby obtaining an organometallic complex of the present invention, [Ir(mppr-P)₂(acac)] (yield of 77%). A synthetic scheme of Step 3 is shown in the following (c-5).

Figure 30A:
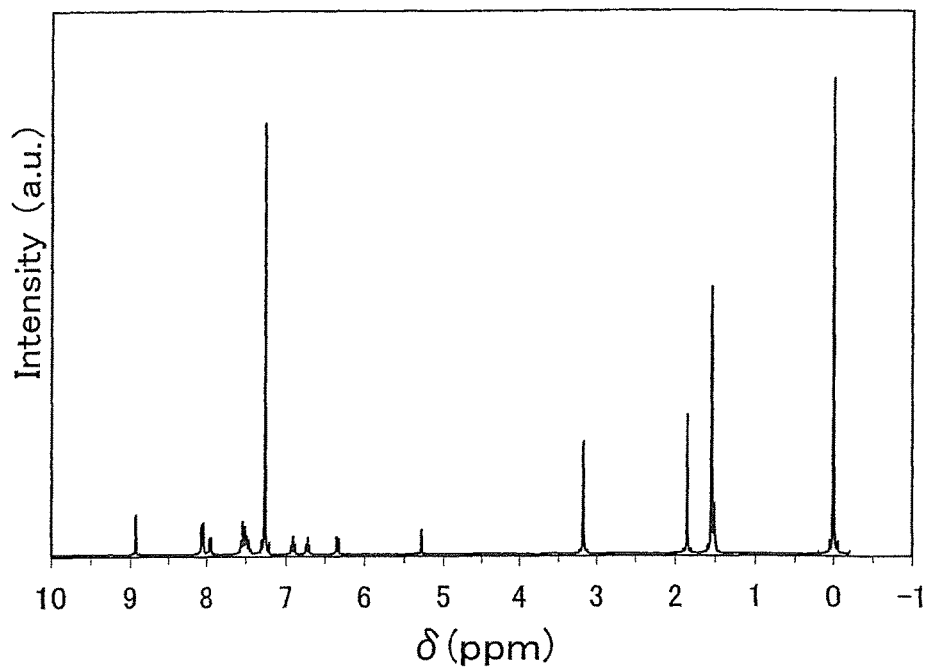
FIGS. 30A and 30B show a $^1$H-NMR chart of (acetylacetonato)bis(3-methyl-2,5-diphenylpyrazinato)iridium(III)
Figure 30B:
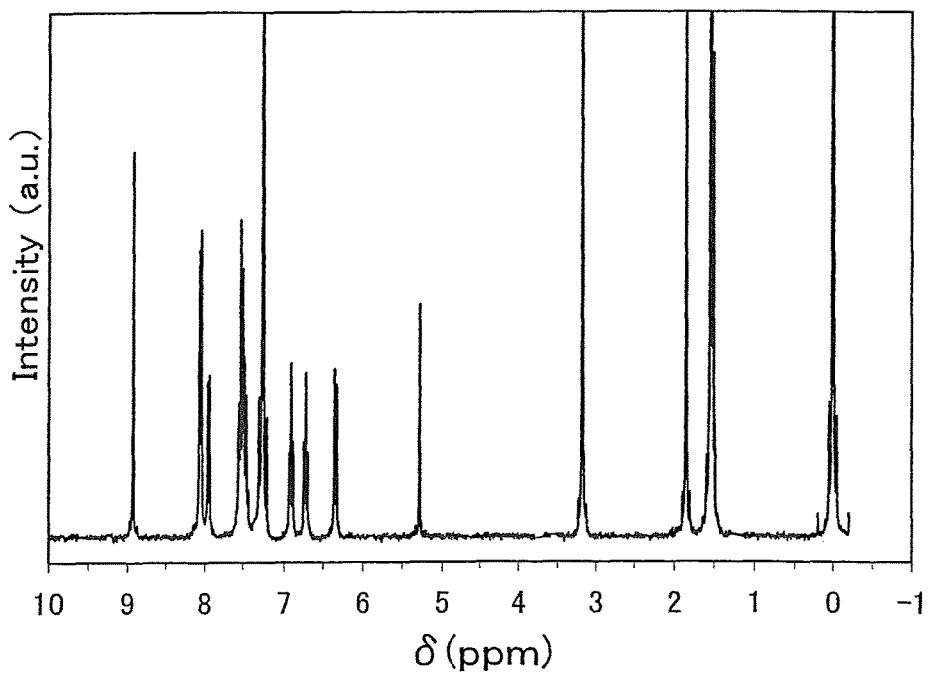

An analysis result of the red-orange powder obtained by the above step by nuclear magnetic resonance spectrometry (¹H-NMR) is shown below. A ¹H-NMR chart is shown in FIGS. 30A and 30B. From FIGS. 30A and 30B, it was found that the organometallic complex [Ir(mppr-P)₂(acac)] of the present invention represented by the above structural formula (34) was obtained in Synthetic Example 6.

¹H-NMR. δ (CDCl₃): 1.85 (s, 6H), 3.17 (s, 6H), 5.29 (s, 1H), 6.35 (d, 2H), 6.72 (t, 2H), 6.91 (t, 2H), 7.55 (m, 6H), 7.95 (d, 2H), 8.06 (d, 4H), 8.93 (s, 2H).

Figure 31:
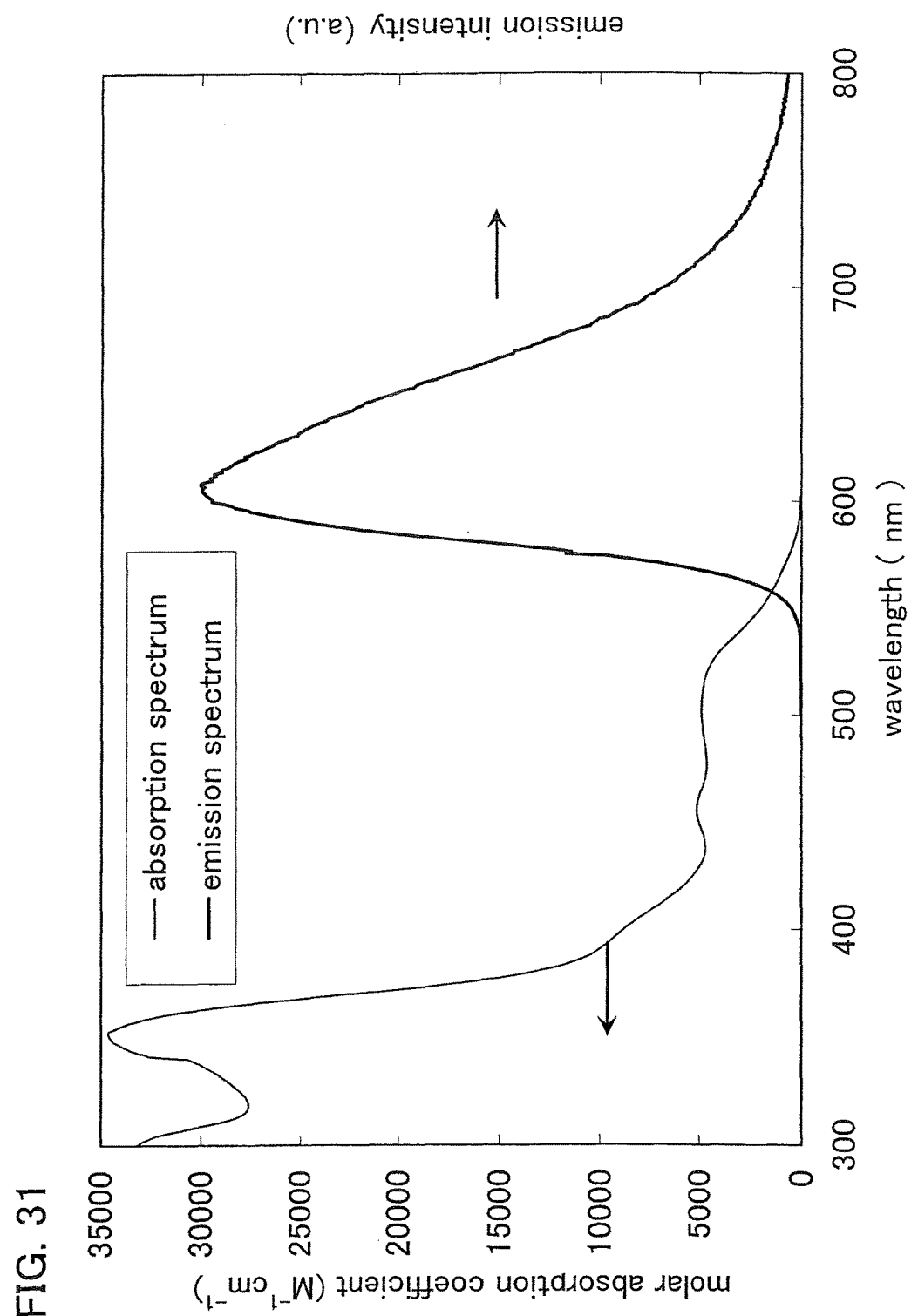
FIG. 31 shows an absorption spectrum and an emission spectrum of (acetylacetonato)bis(3-methyl-2,5-diphenylpyrazinato)iridium(III)

Next, an absorption spectrum of [Ir(mppr-P)₂(acac)] was measured with the use of an ultraviolet-visible light spectrophotometer (manufactured by Japan Spectroscopy Corporation, V550 type). The measurement was conducted by using a dichloromethane solution (0.12 mmol/L) at a room temperature. In addition, an emission spectrum of [Ir(mppr-P)₂(acac)] was measured with the use of a fluorescence spectrophotometer (manufactured by Hamamatsu Photonics Corporation, FS920). The measurement was conducted by using a degassed dichloromethane solution (0.41 mmol/L) at a room temperature. FIG. 31 shows the measurement results. The horizontal axis indicates a wavelength and the vertical axis indicates a molar absorption coefficient and emission intensity.

As shown in FIG. 31, the organometallic complex [Ir(mppr-P)$_2$(acac)] of the present invention has a peak of emission spectrum at 607 nm, and orange light was observed from the solution.

EXAMPLE 8

Example 8 will describe a light emitting element of the present invention with reference to FIG. 12. A chemical formula of a material to be used in this example is shown below.

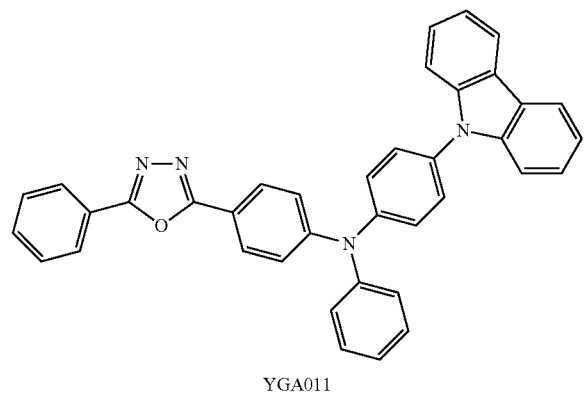 [SMILES: c1ccc(-c2nnc(-c3ccc(N(c4ccccc4)c4ccc(-n5c6ccccc6c6ccccc65)cc4)cc3)o2)cc1]

YGA011

(Light Emitting Element 3)

First, indium tin oxide containing silicon oxide was formed over a glass substrate 2101 by sputtering as a first electrode 2102. The film thickness of the first electrode 2102 was 110 nm and the area thereof was 2 mm×2 mm.

Then, the substrate provided with the first electrode was fixed on a substrate holder which was provided in a vacuum evaporation apparatus, in such a way that a surface provided with the first electrode faced downward. After that, the air inside the vacuum evaporation apparatus was evacuated to approximately 10$^{-4}$ Pa. Then, a layer including a composite material 2103 including an organic compound and an inorganic compound was formed on the first electrode 2102 by co-evaporation of NPB and molybdenum oxide (VI). The film thickness was 50 nm and the weight ratio between NPB and molybdenum oxide (VI) was adjusted to be 4:1 (=NPB: molybdenum oxide). Note that the co-evaporation is an evaporation method by which evaporation is carried out simultaneously from a plurality of evaporation sources in one process chamber.

Next, a hole transporting layer 2104 was foil red on the layer including the composite material 2103 to have a thickness of 10 run using 4,4'-bis[N-(1-naphthyl)-N-phenylamino]biphenyl (abbreviation: NPB) by evaporation using resistance heating.

Further, a light emitting layer 2105 was formed on the hole transporting layer 2104 to have a thickness of 30 mn by co-evaporation of 4-(9H-carbazole-9-yl)-4'-(5-phenyl-1,3,4-oxadiazole-2-yl)triphenylamine) (abbreviation: YGAO11) and (acetylacetonato)bis(2,3,5-triphenylpyrazinato)iridium (III) (abbreviation: Ir(tppr)$_2$(acac)) which is expressed by the structural formula (1). Here, the weight ratio between YGAO11 and Ir(tppr)$_2$(acac) was adjusted to be 1:0.06 (=YGAO11: Ir(tppr)$_2$(acac)).

After that, an electron transporting layer 2106 was formed on the light emitting layer 2105 by depositing bis(2-methyl-8-quinolinolato)(4-phenylphenolato)aluminum (abbreviation: BAlq) so as to have a thickness of 10 nm by evaporation using resistance heating.

Further, an electron injecting layer 2107 was formed on the electron transporting layer 2106 so as to have a thickness of 50 nm by co-evaporation of tris(8-quinolinolato)aluminum (abbreviation: Alq) and lithium. The weight ratio between Alq and lithium was adjusted to be 1:0.01 (=Alq: lithium).

Finally, a second electrode 2108 was formed the electron injecting layer 2107 by depositing aluminum so as to have a thickness of 200 nm by evaporation using resistance heating. Thus, the light emitting element 3 was formed.

Figure 32:
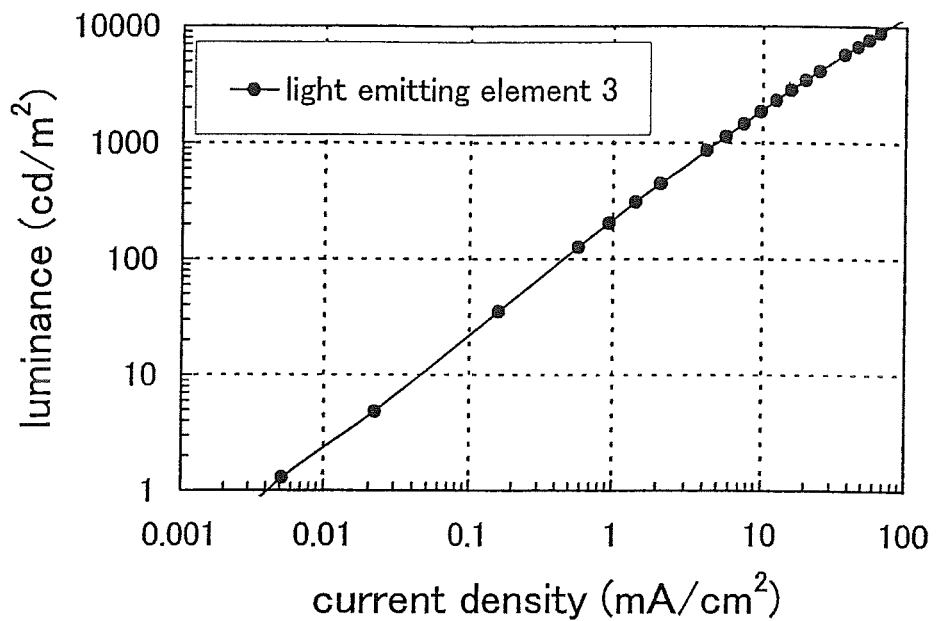
FIG. 32 shows current density-luminance characteristics of a light emitting element manufactured in Example 8.
Figure 33:
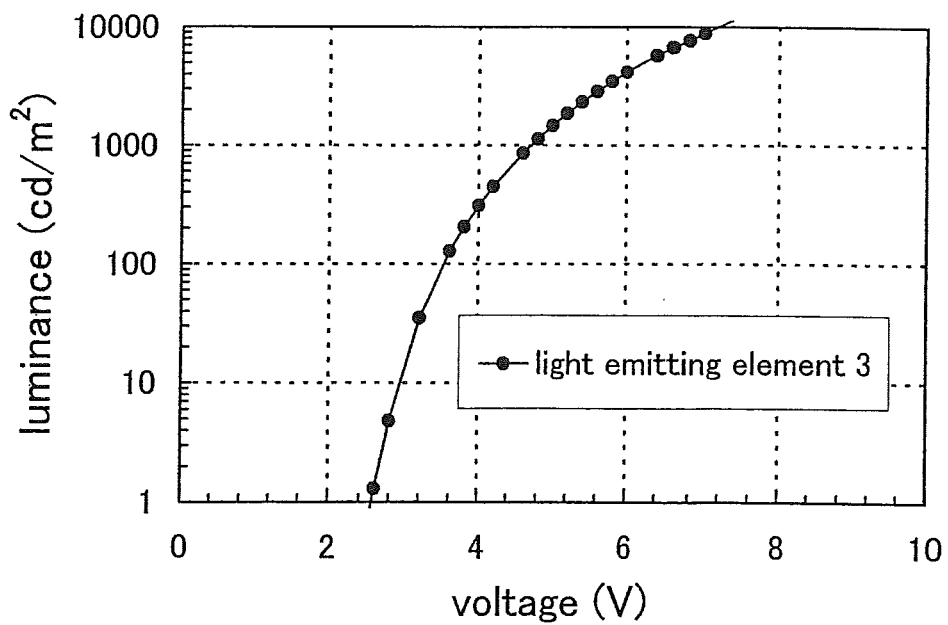
FIG. 33 shows voltage-luminance characteristics of a light emitting element manufactured in Example 8.
Figure 34:
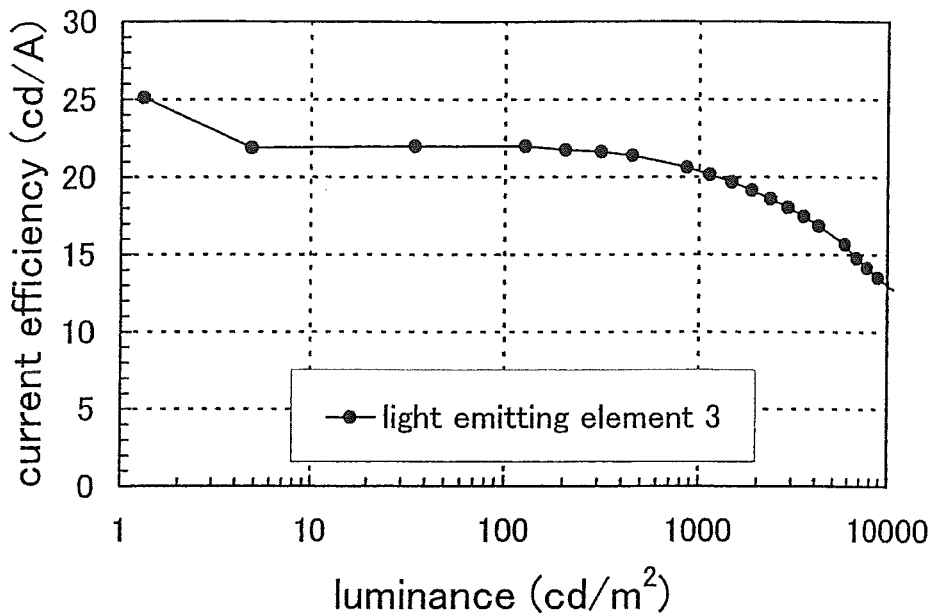
FIG. 34 shows luminance-current efficiency characteristics of a light emitting element manufactured in Example 8.
Figure 35:
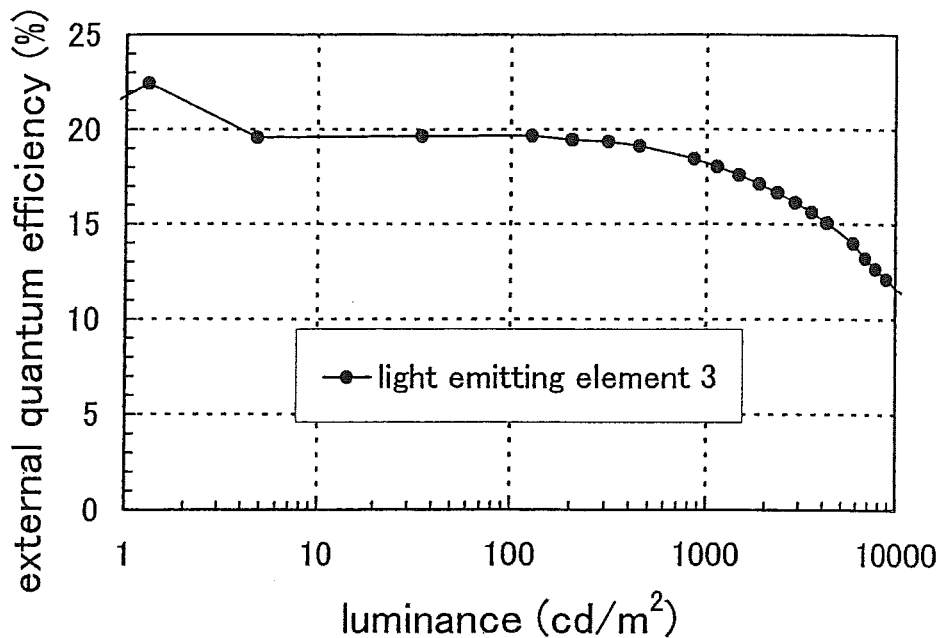
FIG. 35 shows luminance-external quantum efficiency characteristics of a light emitting element manufactured in Example 8.
Figure 36:
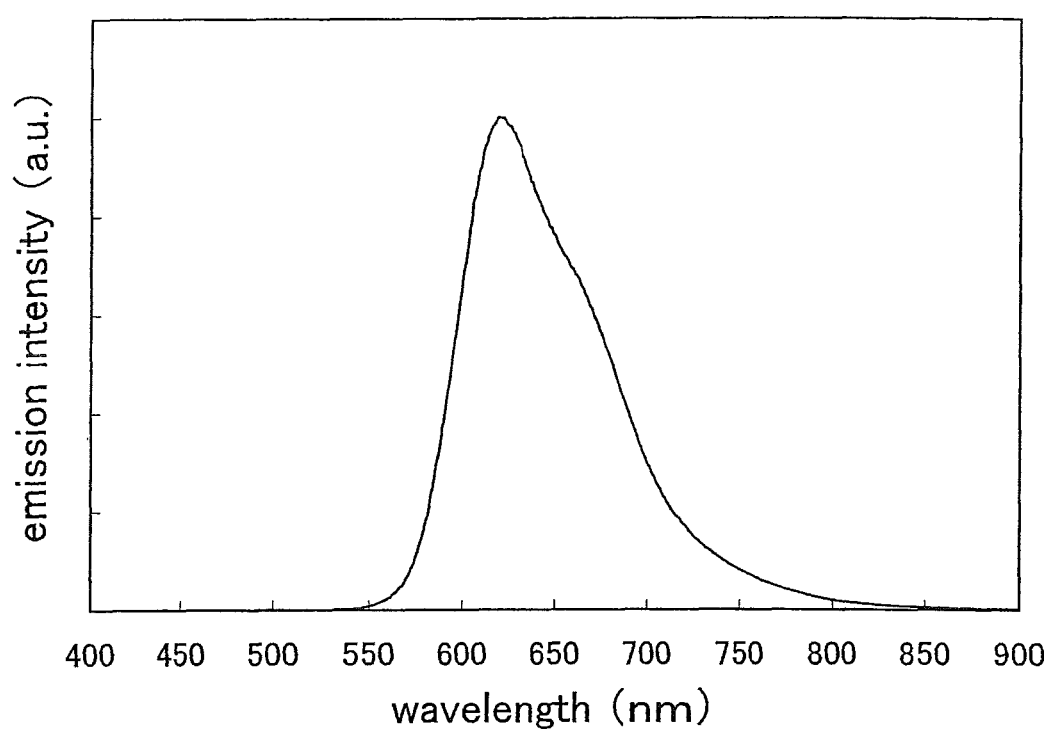
FIG. 36 shows an emission spectrum of a light emitting element manufactured in Example 8.

Current density-luminance characteristics of the light emitting element 3 are shown in FIG. 32. Voltage-luminance characteristics thereof are shown in FIG. 33. Luminance-current efficiency characteristics thereof are shown in FIG. 34. In addition, luminance-external quantum efficiency characteristics are shown in FIG. 35. Also, an emission spectrum upon applying a current of 1 mA is shown in FIG. 36. From FIG. 36, it can be found that light emission of the light emitting element 3 is the light emission of Ir(tppr)$_2$(acac). The CIE chromaticity coordinates of the light emitting element 3 are (x, y)=(0.67, 0.34) when the luminance is 1000 cd/m$^2$, and the light emitting element 3 emits red-color light. Further, as is seen from FIG. 35, the light emitting element 3 exhibits high external quantum efficiency. Particularly, it can be found that the light emitting element 3 has further higher external quantum efficiency than the light emitting element 1 formed in Example 1. The light emitting element 3 uses an organometallic complex of the present invention and a zinc complex for the light emitting layer, which is considered as a cause of realizing higher external quantum efficiency.

From FIG. 34, it is found that the light emitting element 3 has high luminous efficiency. Further, it is found from FIG. 33 that the voltage for obtaining a certain level of luminance is low. This shows that the light emitting element 3 has small power consumption.

EXAMPLE 9

Example 9 will describe the materials used in other examples.

SYNTHETIC EXAMPLE OF BPAPQ

In this synthetic example, a synthetic method of 2,3-bis{4-[N-(4-biphenylyl)-N-phenylamino]phenyl} quinoxaline (abbreviation: BPAPQ) which is represented by the following structural formula (201) will be described.

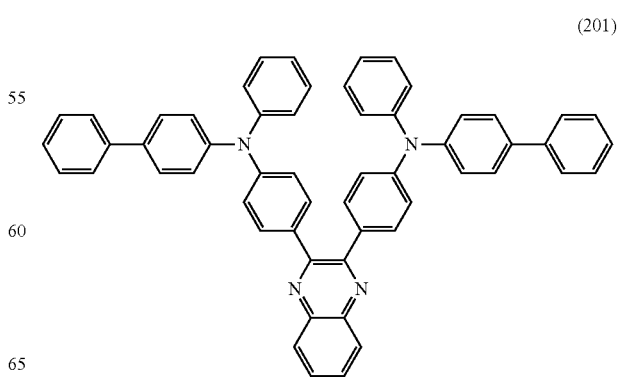

(201)

[Step 1]

A synthetic method of 2,3-bis(4-bromophenyl)quinoxaline will be described. A synthetic scheme of 2,3-bis(4-bromophenyl)quinoxaline will be shown in (D-1).

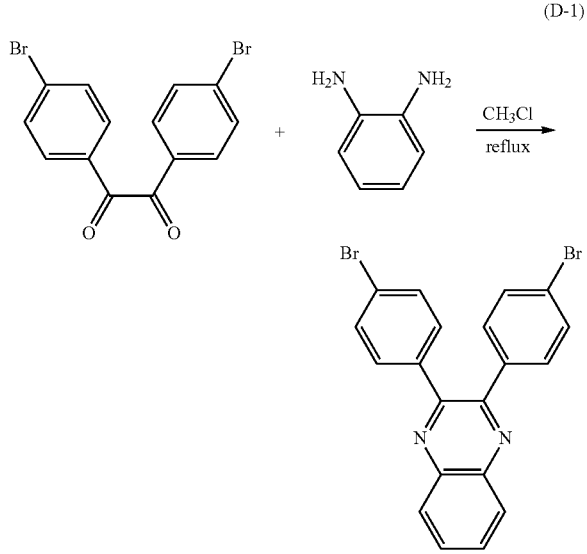

(D-1)

In a nitrogen atmosphere, a chloroform solution (200 mL) containing 30.0 g (81.5 mmol) of 4,4'-dibromobenzyl and 9.00 g (83.2 mmol) of o-phenylenediamine was refluxed at 80° C. for three hours. The reacted solution was washed with water after being cooled to a room temperature. An aqueous layer was extracted with chloroform and the solution obtained by extraction was washed with saturated saline together with the organic layer. After the organic layer was dried with magnesium sulfate, the mixture was filtered and the filtrate was condensed. Accordingly, 33 g (yield: 92%) of objective 2,3-bis(4-bromophenyl)quinoxaline was obtained as a white solid.

[Step 2]

A synthetic method of N-(4-biphenylyl)-N-phenylamine will be described. A synthetic scheme of N-(4-biphenylyl)-N-phenylamine is shown in (D-2).

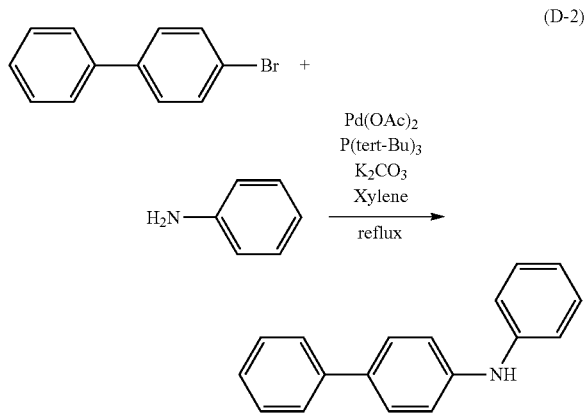

(D-2)

In a nitrogen atmosphere, a xylene suspension (150 mL) containing 20.0 g (85.8 mmol) of 4-bromobiphenyl, 16.0 g (172 mmol) of aniline, 0.19 g (0.858 mmol) of palladium acetate, and 23.7 g (172 mmol) of potassium carbonate, to which 5.2 g (2.5 mmol) of tri-tert-butylphosphine (10% hexane solution) was added, was refluxed at 120° C. for ten hours. After completion of reaction, the reaction mixture was washed with water and an aqueous layer was extracted with toluene. The toluene layer was washed with saturated saline together with an organic layer, and drying with magnesium sulfate was conducted. Then, the mixture was subjected to filtration and the filtrate was condensed. A residue obtained was purified by silica gel column chromatography (developing solution: toluene). The obtained solution was condensed to obtain 13.5 g (yield: 64%) of N-phenyl-N-(4-phenyl)-phenylamine as a white solid.

[Step 3]

A synthetic method of 2,3-bis{4-[N-(4-biphenylyl)-N-phenylamino]phenyl}quinoxaline (hereinafter referred to as BPAPQ) is described. A synthetic scheme of BPAPQ is shown in (D-3).

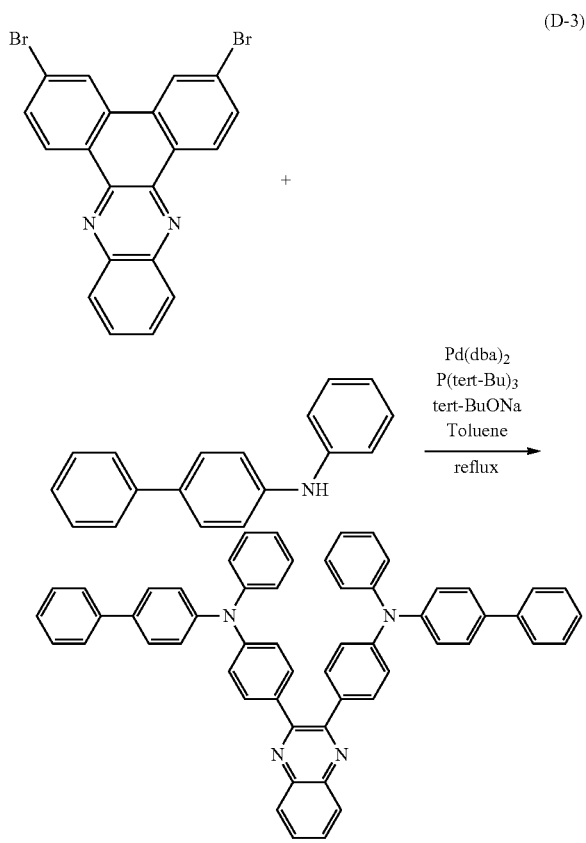

(D-3)

In a nitrogen atmosphere, a toluene suspension (80 mL) containing 5.0 g (11.4 mmol) of 2,3-bis(4-bromophenyl)quinoxaline, 6.1 g (25.0 mmol) of N-(4-biphenylyl)-N-phenylamine, 0.33 g (0.58 mmol) of bis(dibenzylidineacetone)palladium, and 5.5 g (56 8 mmol) of tert-butoxy sodium, to which 1.2 g (0.58 mmol) of tri-tert-butylphosphine (10% hexane solution) was added, was heated at 80° C. for seven hours. After completion of reaction, the reaction mixture was cooled to a room temperature and the precipitate was collected by filtration. The obtained filtrate was dissolved in toluene, the solution was subjected to filtration through celite, Florisil, and alumina, and the filtrate was condensed. The obtained residue was recrystallized with chloroform-hexane to obtain 8.1 g (yield: 78%) of BPAPQ as a yellow solid.

Figure 23A:
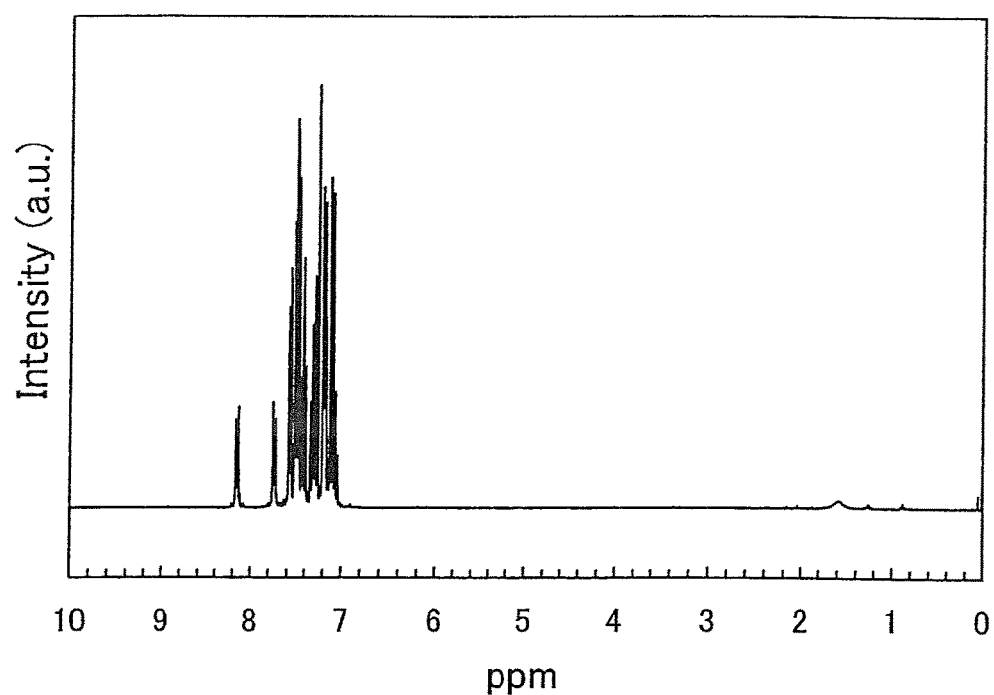
FIGS. 23A and 23B show a $^1$H-NMR chart of 2,3-bis{4-[N-(4-biphenylyl)-N-phenylamino]phenyl}quinoxaline.
Figure 23B:
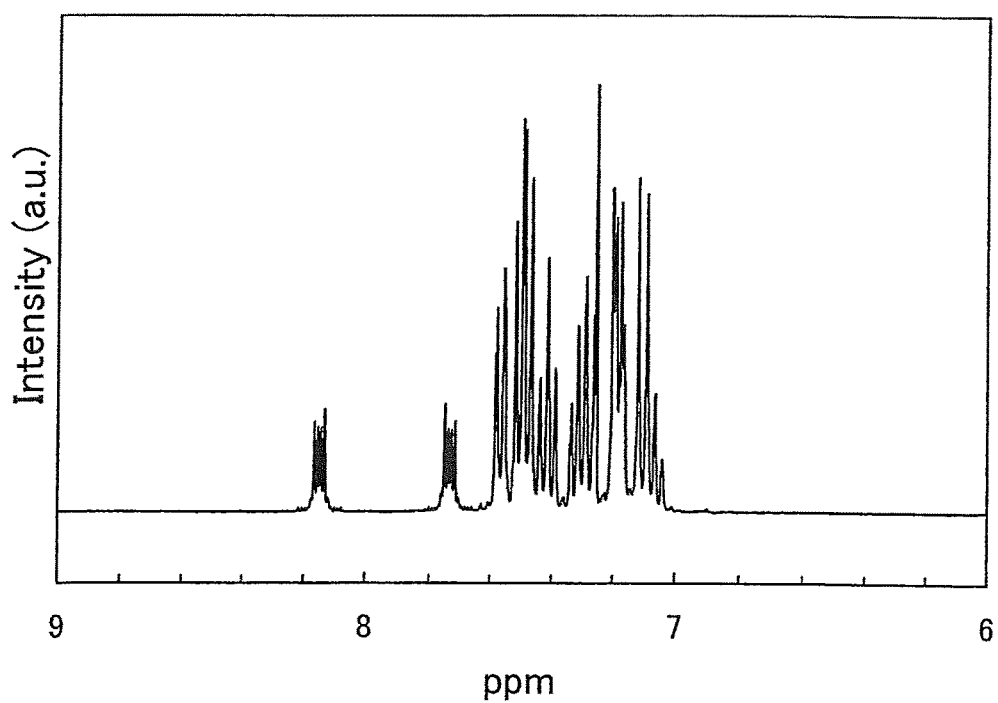

An analysis result of BPAPQ by a proton nuclear magnetic resonance spectroscopy ($^1$H NMR) is as follows. $^1$H NMR (300 MHz, CDCl$_3$); δ=8.16-8.13 (m, 2H), 7.75-7.72 (m, 2H), 7.58-7.04 (m, 36H). FIG. 23A shows an NMR chart of BPAPQ, and FIG. 23B shows an enlarged NMR chart of a part of 6 to 9 ppm.

SYNTHETIC EXAMPLE OF YGAO11

In this synthetic example, a synthetic example of 4-(9H-carbazole-9-yl)-4'-(5-phenyl-1,3,4-oxadiazole-2-yl)triphenylamine) (abbreviation: YGAO11), which is an oxadiazole derivative of the present invention represented by the following structural formula (202) will be specifically described.

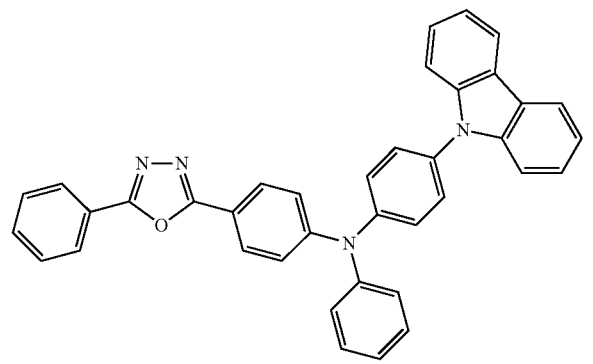

(202)

Step 1: Synthesis of
2-(4-bromophenyl)-5-phenyl-1,3,4-oxadiazole
(abbreviation: O11Br)

In Step 1, O11Br was synthesized in accordance with (i) to (iii) shown below.
(i) Synthesis of 4-bromobenzohydrazide
First, 3.0 g (13.9 mmol) of methyl-4-bromobenzoate was put in a 100-mL three-neck flask, 10 mL of ethanol was added therein, and the mixture was stirred. Thereafter, 4.0 mL of hydrazine monohydrate was added therein, and the mixture was heated and stirred at 78° C. for 5 hours. A solid obtained was washed with water and collected by suction filtration; thus, 2.0 g of a white solid of objective 4-bromobenzohydrazide was obtained (yield: 67%).
(ii) Synthesis of 1-benzoyl-2-(4-bromobenzoyl)hydrazine
Then, 2.0 g (13.9 mmol) of 4-bromobenzohydrazide obtained in (i) above was put in a 300-mL three-neck flask, 7 mL of N-methyl-2-pyrrolidone (abbreviation: NMP) was added therein, and the mixture was stirred. Thereafter, a mixture of 2.5 mL of N-methyl-2-pyrrolidone and 2.5 mL (21.5 mmol) of benzoyl chloride was dropped through a 50-mL dropping funnel, and the mixture was stirred at 80° C. for 3 hours. A solid obtained was washed with water and a sodium carbonate aqueous solution in this order and collected by suction filtration. Then, the solid was recrystallized with acetone; thus, 3.6 g of a white solid of objective 1-benzoyl-2-(4-bromobenzoyl)hydrazine was obtained (yield: 80%).
(iii) Synthesis of O11Br
Further, 15 g (47 mmol) of 1-benzoyl-2-(4-bromobenzoyl)hydrazine obtained by the method shown in (ii) above was put in a 200-mL three-neck flask, 100 mL of phosphoryl chloride was added therein, and the mixture was heated and stirred at 100° C. for 5 hours. After the reaction, a solid obtained by completely distilling off phosphoryl chloride was washed with water and a sodium carbonate aqueous solution in this order and collected by suction filtration. Then, the solid was recrystallized with methanol; thus, 13 g of a white solid of O11Br that was an object of Step 1 was obtained (yield: 89%). A synthetic scheme of Step 1 described above is shown in the following scheme (E-1).

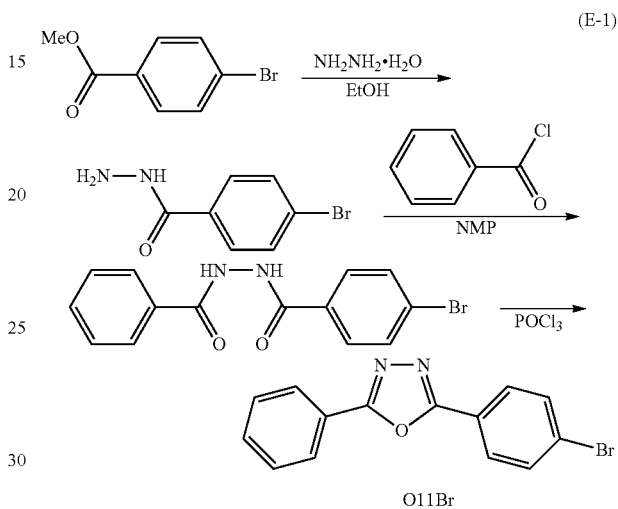

(E-1)

O11Br

Step 2: Synthesis of
4-(9H-carbazole-9-yl)diphenylamine (abbreviation: YGA)

In Step 2, YGA was synthesized according to (i) and (ii) shown below.
(i) Synthesis of 9-(4-bromophenyl)carbazole
First, 56 g (240 mmol) of p-dibromobenzene, 31 g (180 mmol) of carbazole, 4.6 g (24 mmol) of copper iodide, 66 g (480 mmol) of potassium carbonate, and 2.1 g (8 mmol) of 18-crown-6-ether were put in a 300-mL three-neck flask, and nitrogen was substituted for air in the flask. Then, 8 mL of N,N-dimethylpropyleneurea (abbreviation: DMPU) was added therein, and the mixture was stirred at 180° C. for 6 hours. After the reaction mixture was cooled to room temperature, a precipitate was removed by suction filtration. The filtrate was washed with dilute hydrochloric acid, a saturated sodium hydrogen carbonate aqueous solution, and a saturated saline solution in this order and dried with magnesium sulfate. After being dried, the solution was filtered naturally and condensed, and an obtained oily substance was purified by silica gel column chromatography (hexane: ethyl acetate=9:1) and recrystallized with chloroform and hexane; thus, 21 g of an objective light brown plate-shaped crystal of 9-(4-bromophenyl)carbazole was obtained (yield: 35%).
(ii) Synthesis of YGA
Next, 5.4 g (17 mmol) of 9-(4-bromophenyl)carbazole that was obtained in (i) above, 1.8 mL (20 mmol) of aniline, 0.1 g (0.2 mmol) of bis(dibenzylideneacetone)palladium(0), and 3.9 g (40 minol) of sodium-tert-butoxide were put in a 200-mL three-neck flask, and nitrogen was substituted for air in the flask. Then, 0.1 mL of a 10% hexane solution of tri(tert-butyl)phosphine and 50 mL of toluene were added

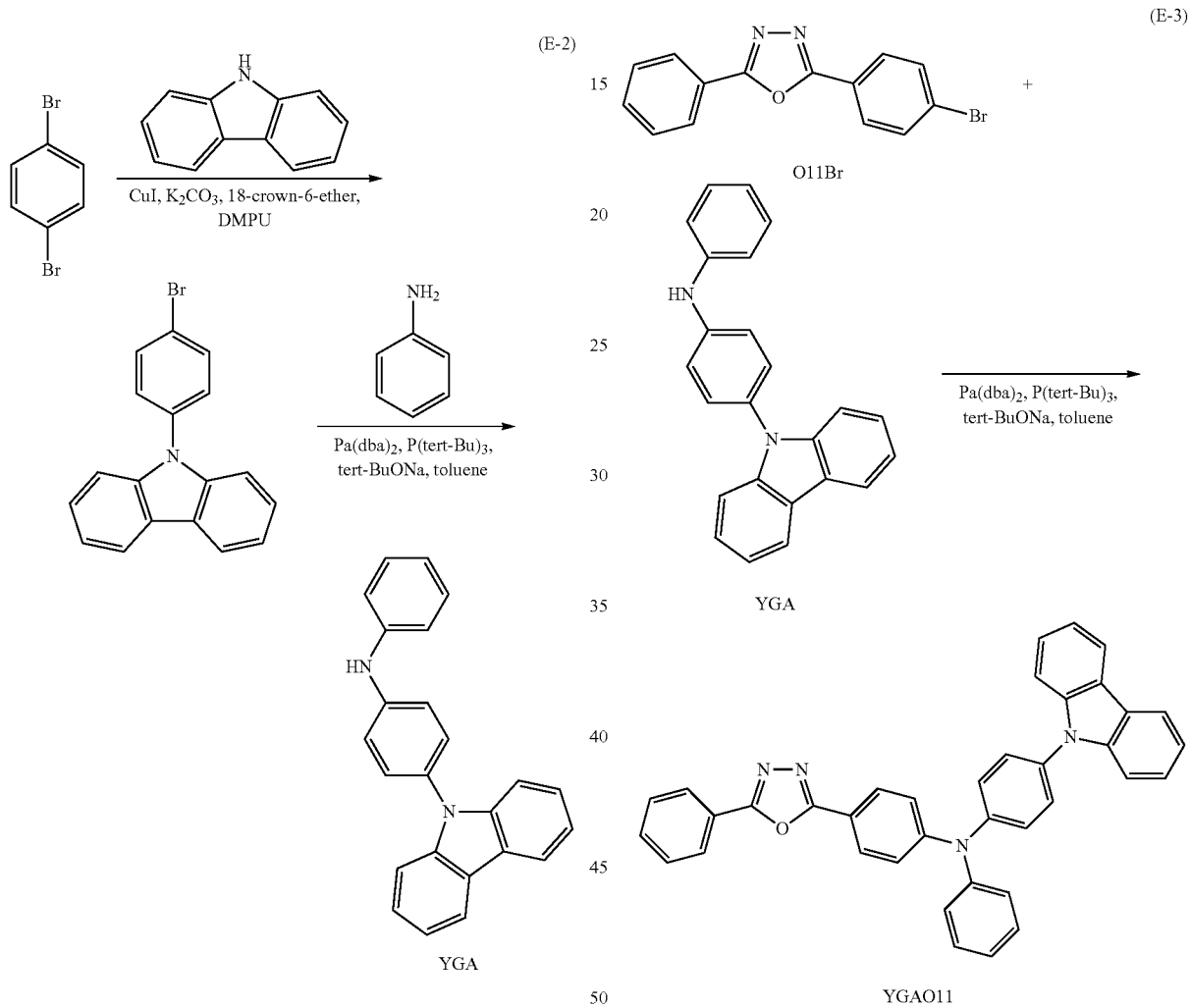

(E-2)

(E-3)

YGA

YGAO11

Step 3: Synthesis of 4-(9H-carbazole-9-yl)-4'-(5-phenyl-1,3,4-oxadiazole-2-yl)triphenylamine) (abbreviation: YGAO11)

3.0 g (10.0 mmol) of O11Br obtained in Step 1, 3.4 g (10.0 mmol) of YGA obtained in Step 2, and 1.9 g (19.9 mmol) of sodium-tert-butoxide were put in a 100-mL three-neck flask, and nitrogen was substituted for air in the flask. Then, 45 mL of toluene, 0.3 mL of a 10% hexane solution of tri(tert-butyl)phosphine, and 0.3 g (0.6 mmol) of bis(dibenzylideneacetone)palladium(0) were added therein, and the mixture was heated and stirred at 120° C. for 5 hours. After the reaction, the mixture was filtered through Celite, and the filtrate was washed with water and dried with magnesium sulfate. After being dried, the solution was filtered, and the filtrate was condensed. A solid obtained was dissolved in toluene and purified by silica gel column chromatography. Purification by column chromatography was performed by using toluene as a developing solvent and then using a mixed solvent of toluene:ethyl acetate=1:1 as a developing solvent. The purified solid was recrystallized with chloroform and hexane; thus, 4.7 g of a light yellow solid YGAO11 that was an object of Synthesis Example 1 was obtained (yield: 85%). The synthetic scheme of Step 3 as described above is shown in the following scheme (E-3).

Figure 37A:
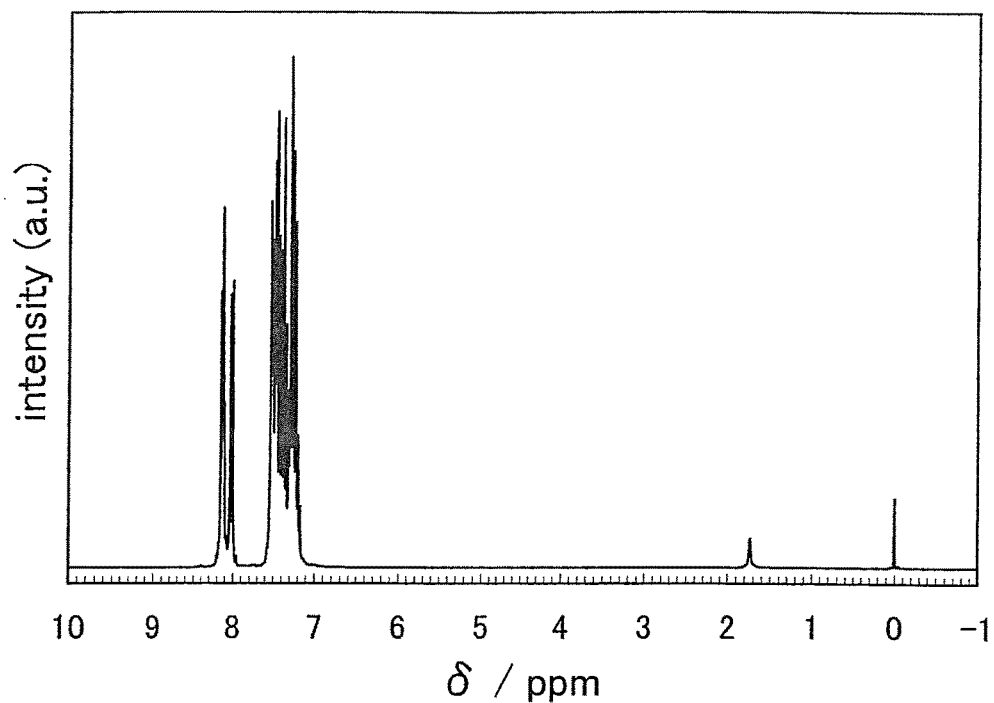
FIGS. 37A and 37B show a $^1$H-NMR chart of 4-(9H-carbazole-9-yl)-4'-(5-phenyl-1,3,4-oxadiazole-2-yl)triphenylamine)
Figure 37B:
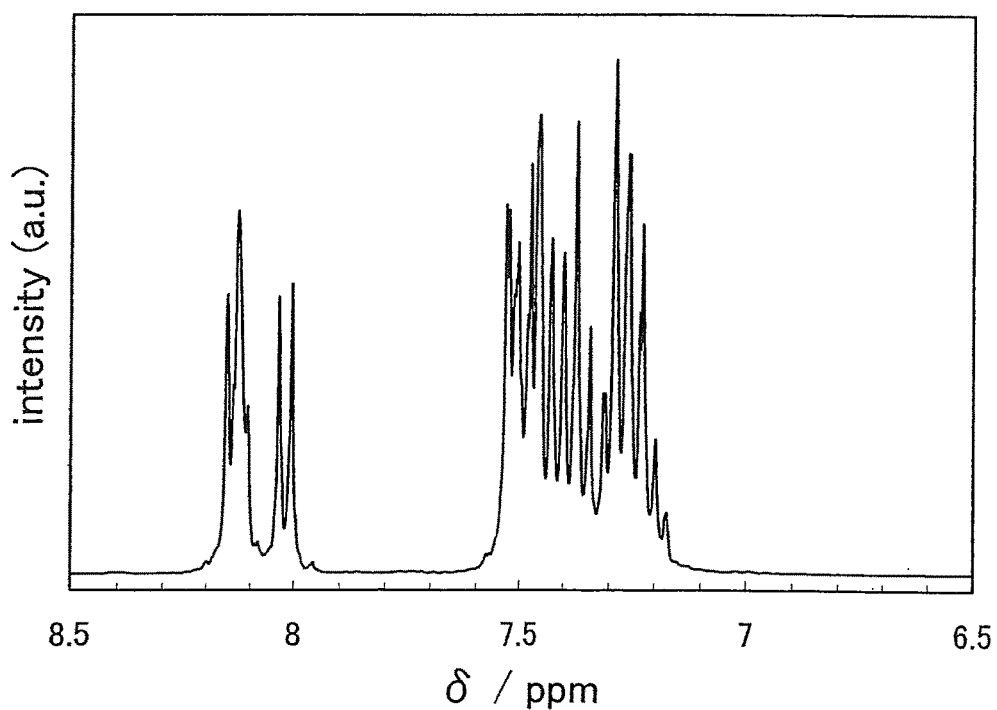

An analysis result of the obtained YGAO11 by nuclear magnetic resonance spectroscopy ($^1$H-NMR) is shown below. FIG. 37A shows an $^1$H-NMR chart and FIG. 37B shows an enlarged chart thereof. Accordingly, it was found that the YGAO11 represented by the above structural formula (202) was obtained in Synthesis Example 1.

$^1$H-NMR (CDCl$_3$, 300 MHz,): δ=7.14-7.53 (m, 19H), δ=8.03 (d, J=8.7, 2H), δ=8.11-8.15 (m, 4H)

In addition, sublimation purification of the obtained YGAO11 was performed by a train sublimation method. Under a reduced pressure of 7 Pa, sublimation purification was performed at 265° C. for 12 hours, setting the flow rate of argon to be 3 mL/min. When sublimation purification was performed on 4.5 g of YGAO11, the yield was 3.4 g and 76%.

Further, the optimal molecular structure of YGAO11 in the ground state was calculated using the B3LYP/6-311 (d, p) of the density functional theory (DFT). The accuracy of calculation of the DFT is higher than that of a Hartree-Fock (HF) method which does not consider electron correlation. In addition, calculation costs for the DFT are lower than that of a method of perturbation (MP) which has the same level of accuracy of calculation as that of the DFT. Therefore, the DFT was employed for this calculation. The calculation was performed using a high performance computer (HPC) (Altix3700 DX, by SGI Japan, Ltd.). When singlet excitation energy (energy gap) of YGAO11 was calculated using the B3LYP/6-311 (d, p) of a time-dependent density functional theory (TDDFT) in the molecular structure optimized by the DFT, the singlet excitation energy was 3.18 eV. In addition, when triplet excitation energy of YGAO11 was calculated, it was 2.53 eV. According to the above results, it is understood that the oxadiazole derivative of the present invention is a substance having high excitation energy, in particular, a substance having high triplet excitation energy.

EXAMPLE 10

SYNTHETIC EXAMPLE 7

In the organometallic complex represented by the general formula (G12) in the embodiment mode, Synthetic Example 7 will specifically describe a synthetic example of an organometallic complex of the present invention represented by structural formula (45), in which each of $R^4$ and $R^9$ is a methyl group, each of $R^3$, $R^5$ to $R^8$, and $R^{10}$ to $R^{11}$ is hydrogen, $Ar^1$ is a 3-fluorophenyl group, and L is a ligand represented by structural formula (L1), that is (acethylacetonato)bis[5-(3-fluorophenyl)-2,3-di-p-tolylpyrazinato]iridium(III) (abbreviation: [Ir(Mdppr-3FP)$_2$(acac)]).

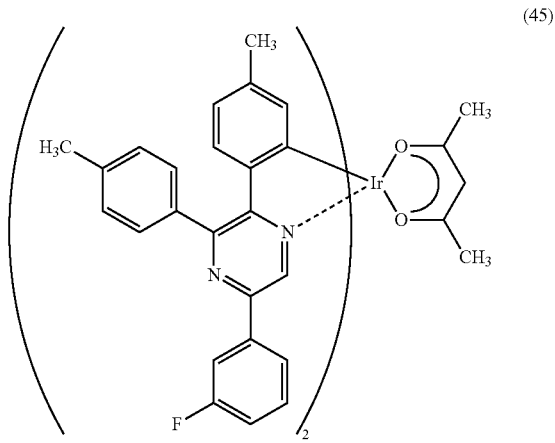

(45)

Step 1: Synthesis of 5-(3-fluorophenyl)-2,3-di-p-tolylpyrazine (abbreviation: HMdppr-3FP)

In a nitrogen atmosphere, 11 mL of a hexane solution (1.58 mol/L) of n-butyllithium was dropped into a mixed solution of 2.86 g of 3-bromofluorobenzene and 16 mL of tetrahydrofuran at −78° C., and the solution was stirred for 2 hours, keeping the temperature at −78° C. The solution obtained was dropped into a mixed solution, which is cooled with ice, of 3.53 g of 2,3-di-p-tolylpyrazine that is an intermediate obtained in Step 1 of Synthetic Example 4 and 25 mL of tetrahydrofuran, and stirred for 12 hours at a room temperature. This mixture was added with water, and an organic layer was extracted with dichloromethane. The organic layer obtained was washed with water and dried with anhydrous magnesium sulfate. The solution after drying was added with activated manganese dioxide excessively and filtration was conducted. A solvent of this solution was distilled off A residue obtained by the distillation was purified by silica gel column chromatography which uses dichloromethane as a developing solvent; thereby obtaining an objective pyrazine derivative HMdppr-3FP (orange powder, yield of 8%). A synthetic scheme of Step 1 is shown in the following (a-6).

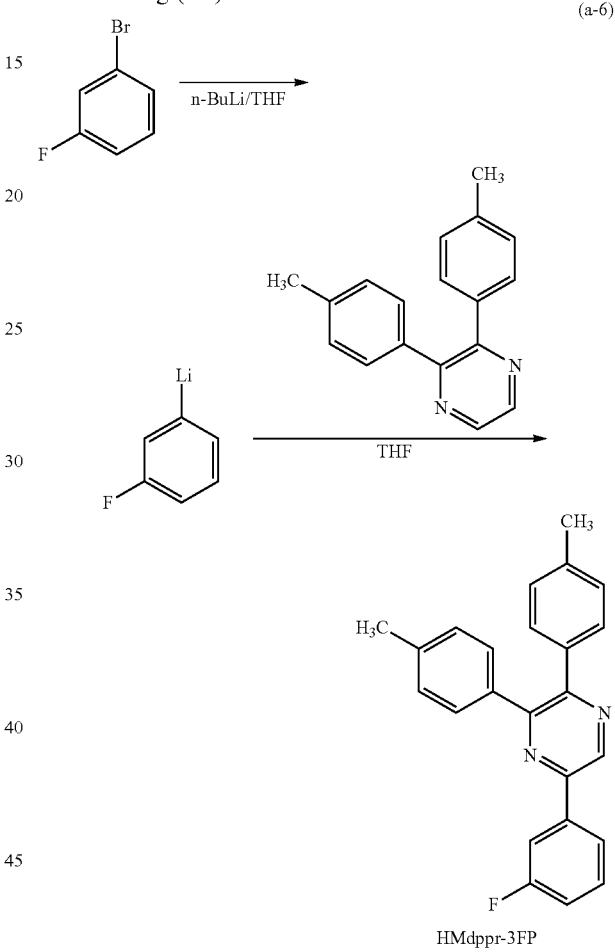

(a-6)

HMdppr-3FP

Step 2: Synthesis of di-μ-chloro-bis{bis[5-(3-fluorophenyl)-2,3-di-p-tolylpyrazinato]iridium(III)}(abbreviation: [Ir(Mdppr-3FP)$_2$Cl]$_2$)

Next, 12 mL of 2-ethoxyethanol, 4 mL of water, 0.14 g of the pyrazine derivative HMdppr-3FP obtained in the above Step 1, and 0.06 g of iridium chloride hydrate (IrCl$_3$·H$_2$O) (produced by Sigma-Aldrich Corp.) were put in an eggplant-type flask with a reflux pipe, and the inside air of the flask was substituted by argon. Then, a reaction was carried out by irradiation with microwave (2.45 GHz, 100 W) for 30 minutes. A red powder precipitated from the reacted solution was filtered and washed with ethanol; thereby obtaining a dinuclear complex [Ir(Mdppr-3FP)$_2$Cl]$_2$ (yield of 16%). The irradiation of microwave was conducted using a microwave synthesis system (Discovery, manufactured by CEM Corporation). A synthetic scheme of Step 2 is shown in the following (b-6).

(b-6)

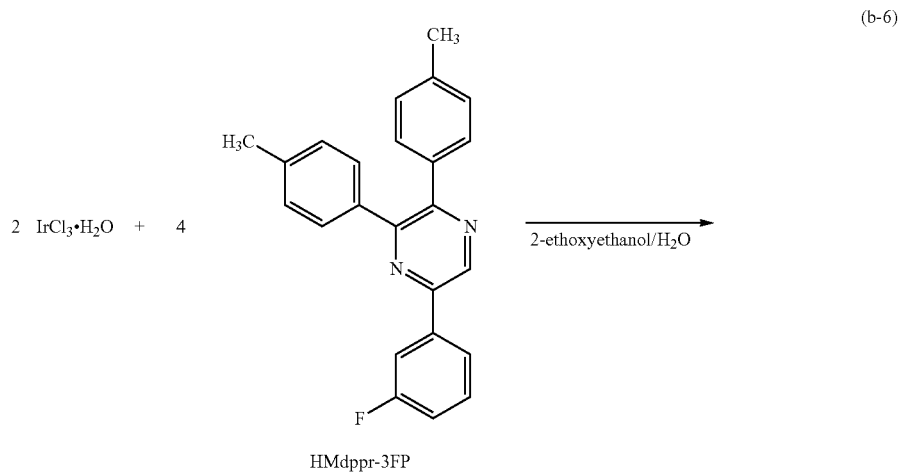

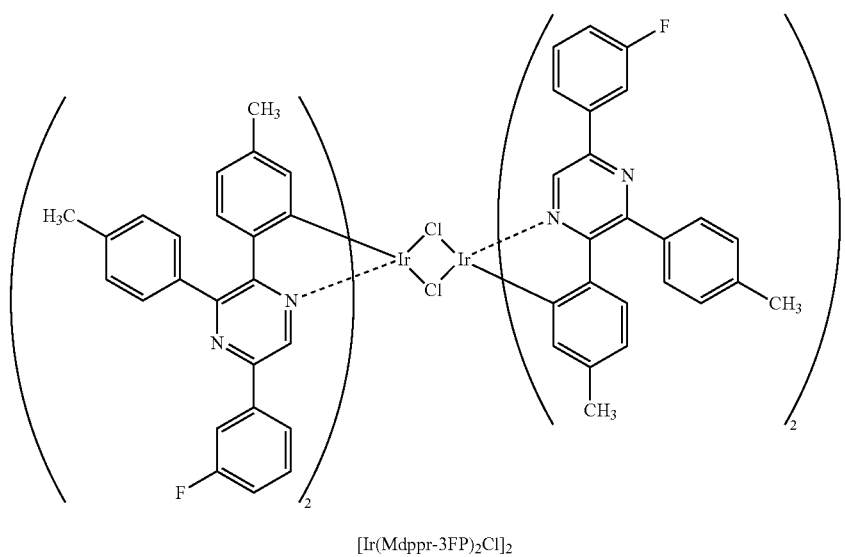

[Ir(Mdppr-3FP)₂Cl]₂

Step 3: Synthesis of (acetylacetonato)bis[5-(3-fluorophenyl)2,3-di-p-tolylpyrazinato]iridium(III) (abbreviation: [Ir(Mdppr-3FP)₂(acac)]

Next, 3 mL of 2-ethoxyethanol, 0.03 g of the dinuclear complex [Ir(Mdppr-3FP)₂Cl]₂ obtained in the above Step 2, 0.005 mL of acetylacetone, and 0.02 g of sodium carbonate were put in an eggplant-type flask with a reflux pipe, and the inside air of the flask was substituted by argon. Then, a reaction was carried out by irradiation with microwave (2.45 GHz, 100 W) for 15 minutes. The reacted solution was filtered, and then a solvent of the obtained filtrate was distilled off. A residue obtained by the distillation was purified by silica gel column chromatography which uses dichloromethane as a developing solvent; thereby obtaining an organometallic complex of the present invention, [Ir(Mdppr-3FP)₂(acac)] (red powder, yield of 50%). A synthetic scheme of Step 3 is shown in the following (c-6).

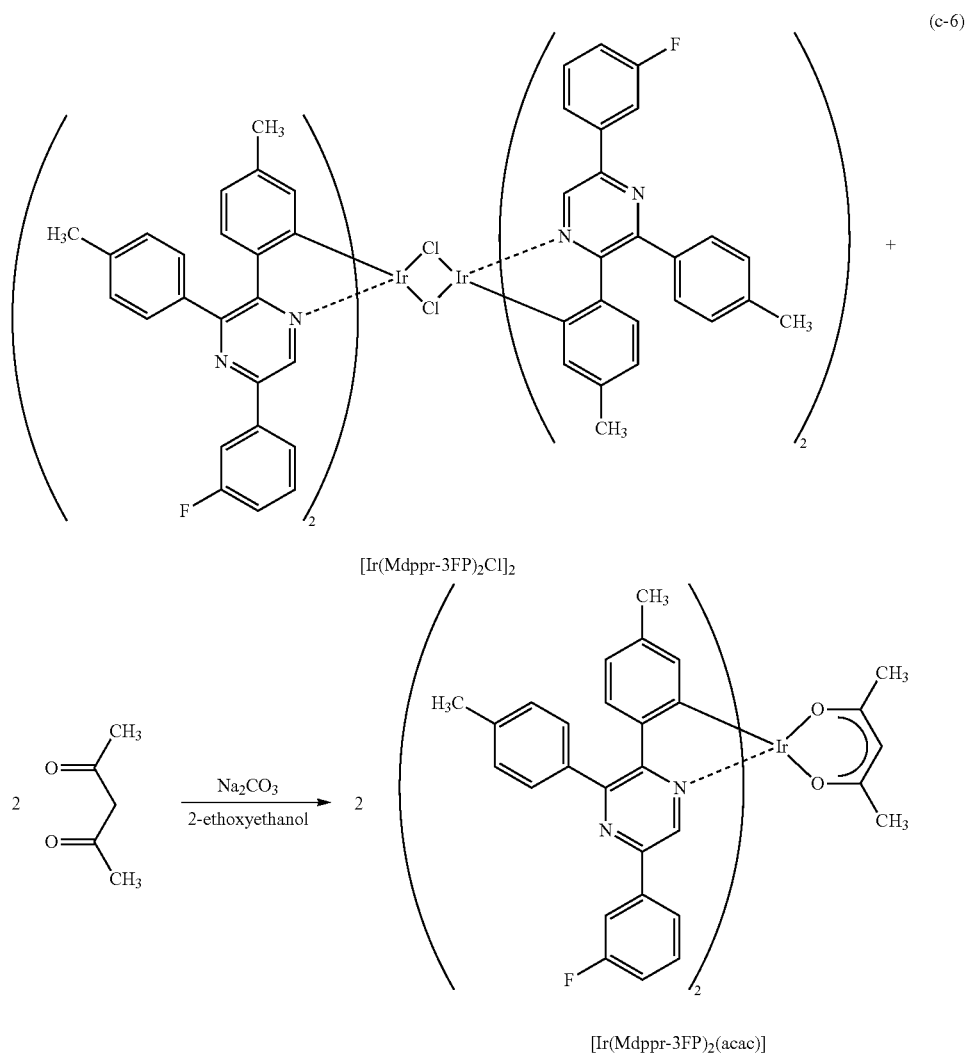

[Ir(Mdppr-3FP)₂Cl]₂

[Ir(Mdppr-3FP)₂(acac)]

Figure 38A:
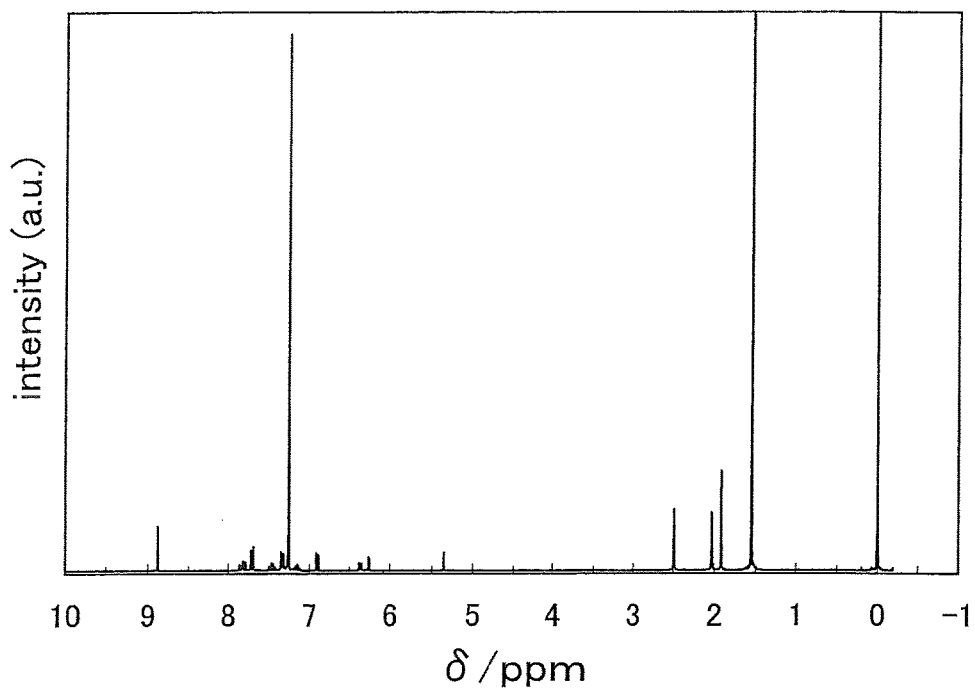
FIGS. 38A and 38B show a $^1$H-NMR chart of (acetylacetonato)bis[5-(3-fluorophenyl)2,3-di-p-tolylpyrazinato] iridium(III)
Figure 38B:
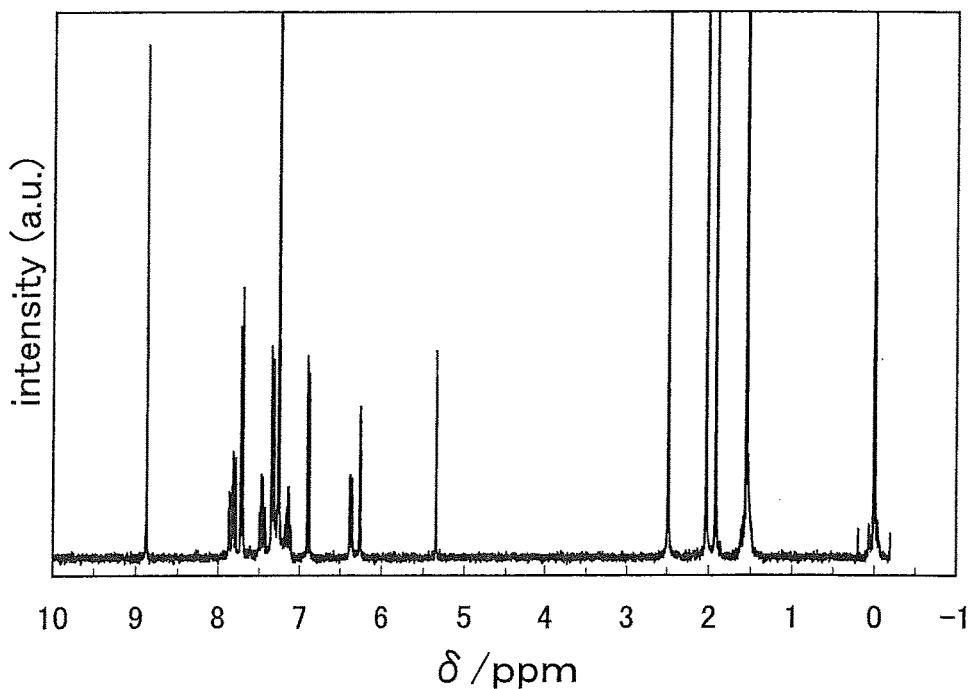

An analysis result of the red powder obtained in Step 3 by nuclear magnetic resonance spectrometry ($^1$H-NMR) is shown below. A $^1$H-NMR chart is shown in FIGS. 38A and 38B. From FIGS. 38A and 38B, it was found that the organometallic complex [Ir(Mdppr-3FP)₂(acac)] of the present invention represented by the above structural formula (45) was obtained in Synthetic Example 7.

$^1$H-NMR. δ (CDCl₃): 1.92 (s, 6H), 2.03 (s, 6H), 2.49 (s, 6H), 5.36 (s, 1H), 6.27 (s, 2H), 6.37 (dd, 2H), 6.90 (d, 2H), 7.15 (m, 2H), 7.34 (d, 4H), 7.46 (m, 2H), 7.71 (d, 4H), 7.82 (m, 4H), 8.87 (s, 2H).

Figure 39:
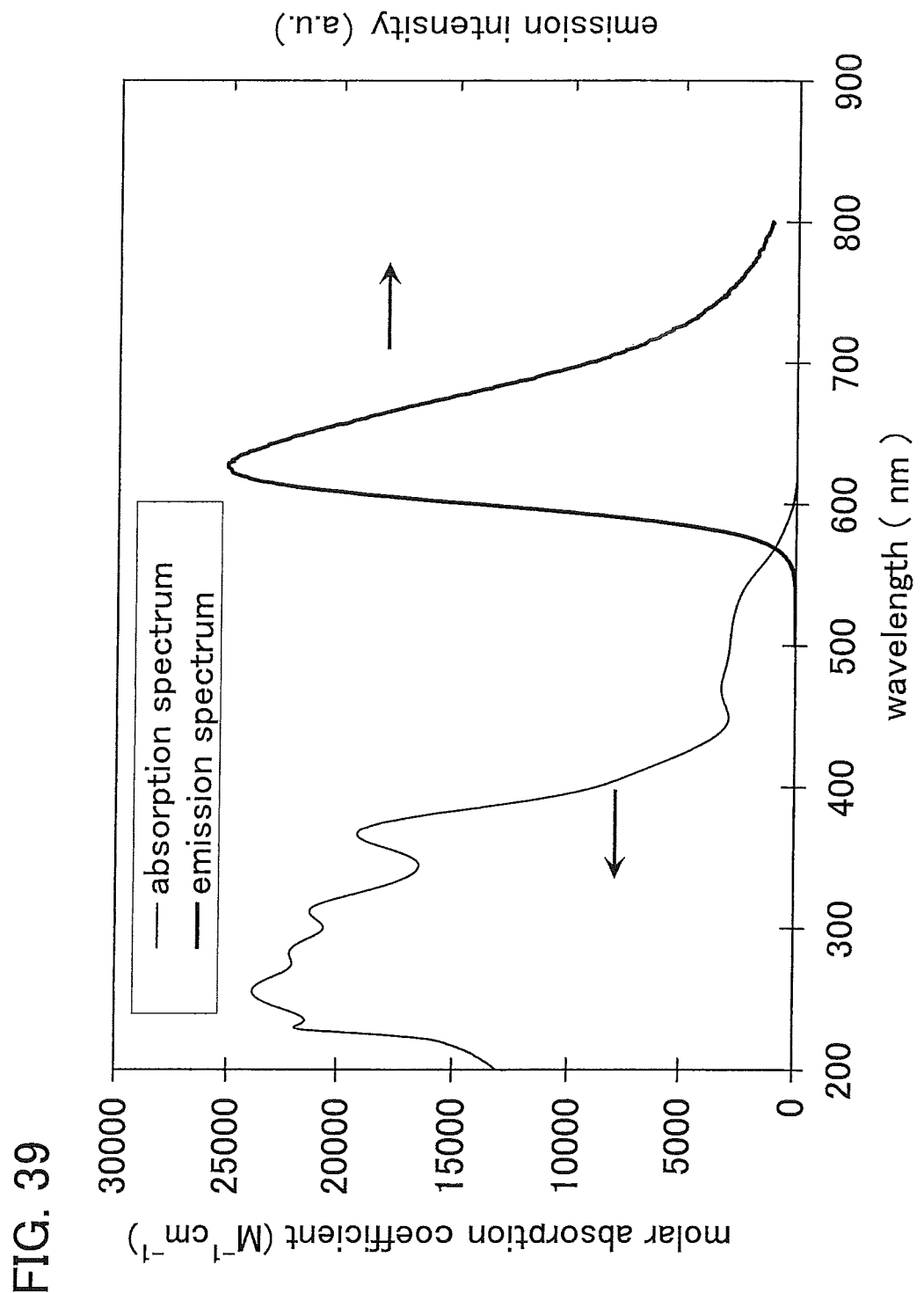
FIG. 39 shows an absorption spectrum and an emission spectrum of (acetylacetonato)bis[5-(3-fluorophenyl)2,3-di-p-tolylpyrazinato]iridium(III).

Next, an absorption spectrum of [I (Mdppr-3FP)₂(acac)] was measured with the use of an ultraviolet-visible light spectrophotometer (manufactured by Japan Spectroscopy Corporation, V550 type). The measurement was conducted by using a dichloromethane solution (0.010 mmol/L) at a room temperature. In addition, an emission spectrum of [Ir(Mdppr-3FP)₂(acac)] was measured with the use of a fluorescence spectrophotometer (manufactured by Hamamatsu Photonics Corporation, FS920). The measurement was conducted by using a degassed dichloromethane solution (0.35 mmol/L) at a room temperature. FIG. 39 shows the measurement results. The horizontal axis indicates a wavelength and the vertical axis indicates a molar absorption coefficient and emission intensity. Note that the excitation wavelength was set at 468 nm.

As shown in FIG. 39, the organometallic complex [Ir (Mdppr-3FP)₂(acac)] of the present invention has a peak of emission spectrum at 627 nm, and red light was observed from the solution.

This application is based on Japanese Patent Application serial No. 2006-077899 filed in Japan Patent Office on Mar. 21, 2006, the entire contents of which are hereby incorporated by references.

What is claimed is:

1. A compound comprising:
a structure represented by the following formula:

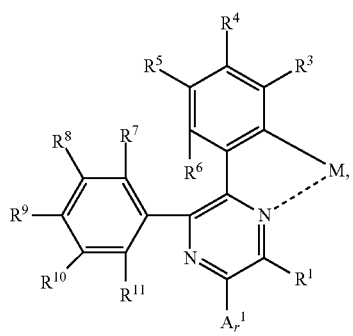

wherein:
$A_r^1$ represents an unsubstituted phenyl group or a phenyl group having an alkyl group having 1 to 4 carbon atoms;
$R^1$ is hydrogen;
$R^3$ to $R^{11}$ independently represent any one of hydrogen and an alkyl group having 1 to 4 carbon atoms; and
M is iridium.

2. A compound comprising:
a structure represented by the following formula:

$$\left( \begin{array}{c} R^5 \\ R^8 \\ R^9 \\ R^{10} \\ R^{11} \end{array} \begin{array}{c} R^4 \\ R^3 \\ R^6 \\ N \\ N \\ R^1 \\ A_r^1 \end{array} \right)_n M-L$$

wherein:
$A_r^1$ represents an unsubstituted phenyl group or a phenyl group having an alkyl group having 1 to 4 carbon atoms;
$R^1$ is hydrogen;
$R^3$ to $R^{11}$ independently represent any one of hydrogen and an alkyl group having 1 to 4 carbon atoms;
M is iridium;
n is 2; and
L is a monoanionic ligand.

3. A light-emitting device comprising:
a pair of electrodes; and
the compound according to claim 2, between the pair of electrodes.

4. The light-emitting device according to claim 3, further comprising:
a light-emitting layer between the pair of electrodes,
wherein the compound is included in the light-emitting layer.

5. The light-emitting device according to claim 4,
wherein the light-emitting layer comprises a host material, and
wherein the compound is dispersed in the host material.

6. The light-emitting device according to claim 3,
wherein one of the pair of electrodes transmits visible light.

7. The light-emitting device according to claim 4, further comprising:
a hole injection layer between one of the pair of electrodes and the light-emitting layer,
wherein the hole injection layer comprises an organic compound and an electron acceptor to the organic compound.

8. A lighting device comprising the light-emitting device according to claim 3.

9. An electronic apparatus comprising the light-emitting device according to claim 3.

10. A light-emitting device comprising:
a pair of electrodes; and
a first light-emitting layer and a second light-emitting layer which are located between the pair of electrodes,
wherein one of the first light-emitting layer and the second light-emitting layer comprises the compound according to claim 2.

11. The light-emitting device according to claim 10,
wherein the first light-emitting layer is spaced from the second light-emitting layer.

12. The light-emitting device according to claim 10,
wherein the other of the first light-emitting layer and the second light-emitting layer comprises a light-emitting material.

13. The light-emitting device according to claim 12,
wherein the first light-emitting layer and the second light-emitting layer are configured to give white emission.

14. The light-emitting device according to claim 10,
wherein the one of the first light-emitting layer and the second light-emitting layer comprises a host material, and
wherein the compound is dispersed in the host material.

15. The light-emitting device according to claim 10,
wherein one of the pair of electrodes transmits visible light.

16. The light-emitting device according to claim 10, further comprising:
a hole injection layer which is in contact with one of the pair of electrodes.

17. A lighting device comprising the light-emitting device according to claim 10.

18. An electronic apparatus comprising the light-emitting device according to claim 10.

19. The light-emitting device according to claim 3, wherein the compound is represented by any of the following formulae:

20. The light-emitting device according to claim 10, wherein the compound is represented by any of the following formulae:
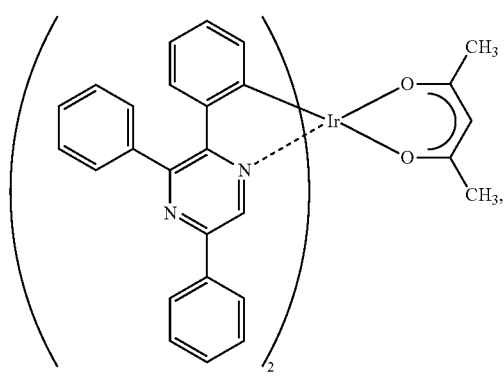
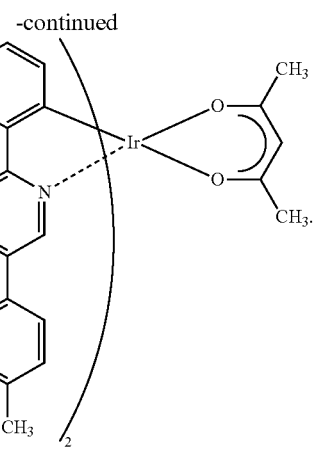
* * * * *